US006190189B1

(12) United States Patent
Li et al.

(10) Patent No.: US 6,190,189 B1
(45) Date of Patent: Feb. 20, 2001

(54) CELLULASES AND CODING SEQUENCES

(75) Inventors: Xin-Liang Li; Lars G. Ljungdahl, both of Athens; Huizhong Chen, Lawrenceville, all of GA (US)

(73) Assignee: University of Georgia Research Foundation, Inc., Athens, GA (US)

( * ) Notice: Under 35 U.S.C. 154(b), the term of this patent shall be extended for 0 days.

(21) Appl. No.: 09/286,691

(22) Filed: Apr. 5, 1999

Related U.S. Application Data

(63) Continuation-in-part of application No. PCT/US97/18008, filed on Oct. 3, 1997
(60) Provisional application No. 60/027,883, filed on Oct. 4, 1996.

(51) Int. Cl.⁷ .............................. C12N 9/42; C12N 15/56
(52) U.S. Cl. ................ 439/209; 435/252.3; 435/252.33; 435/252.5; 536/23.2
(58) Field of Search .......................... 435/252.33, 252.3, 435/252.5, 209; 536/23.2

(56) References Cited

U.S. PATENT DOCUMENTS 5,591,619  1/1997  Li et al. ............................... 435/201

OTHER PUBLICATIONS

Barichievich and Calza (1990) "Supernatant Protein and Cellulase Activities of the Anaerobic Ruminal Fungus *Neocallismastix frontalis* EB188" *Applied and Environmental Microbiology* 56:43–48.

Béguin, P. (1990) "Molecular Biology of Cellulose Degradation" *Annu. Rev. Microbiol.* 44:219–248.

Borneman et al. (1989) "Fermentation Products and Plant Cell Wall–Degrading Enzymes Produced by Monocentric and Polycentric Anaerobic Ruminal Fungi" *Applied and Environmental* Microbiology 55:1066–1073.

Borneman and Akin (1994) "The Nature of Anaerobic Fungi and Their Polysaccharide Degrading Enzymes" *Mycoscience* 35:199–211.

Chen et al. (1995) "A Cyclophilin from the Polycentric Anaerobic Rumen Fungus Orpinomyces sp. Strain PC–2 is Highly Homologous to Vertebrate Cyclophilin B" *Proc. Natl. Acad. Sci. USA* 92:2587–2591.

Chen et al. (1995) "Biomass Degrading Enzymes from Anaerobic Rumen Fungi" In: Southern Association of Agricultural Scientists Bulletin: Biochemistry and Biotechnology, Ballal, S.K. (Ed.). 8:1–6.

Chen et al. (1994) "Isolation and Properties of an Extracellular β–Glucosidase from the Polycentric Rumen Fungus Orpinomyces sp. Strain PC–2" *Applied and Environmental Microbiology* 60:64–70.

Choi and Ljungdahl (1996) "Dissociation of the Cellulosome of *Clostridium thermocellum* in the Presence of Ethylenediaminetetracetic Acid Occurs with the Formation of Truncated Polypeptides" *Biochemistry* 35:4897–4905.

Choi and Ljungdahl (1996) "Structural Role of Calcium for the Organization of the Cellulosome of *Clostridium thermocellum*" *Biochemistry* 35:4906–4910.

Chow et al. (1994) "The cel3 Gene *Agaricus bisporus* Codes for a Modular Cellulase and Is Transcriptionally Regulated by the Carbon Source" *Applied and Environmental Microbiology* 60:2779–2785.

Damude et al. (1993) "Endoglucanase CasA form Alkalophilic Streptomyces Strain KSM–9 Is a Typical Member of Family B of β–1,4–Glucanases" *Gene* 123:105–107.

Denman et al. (1996) "Characterization of a *Neocallimastix patriciarum* Cellulase cDNA (celA) Homologous to *Trichoderma reesei* Cellobiolhydrolase II" *Applied and Environmental Microbiology* 62:1889–1896.

Fanutti et al. (1995) "The Conserved Noncatalytic 40–Residue Sequence in Cellulases and Hemicellulases from Anaerobic Fungi Functions as a Protein Docking Domain" *The Journal of Biological Chemistry* 270:29314–29322.

Felix and Ljungdahl (1993) "The Cellulosome: The Exocellular Organelle of Clostridium" *Annu. Rev. Microbiol.* 47:791–819.

Gilbert et al. (1992) "Homologous Catalytic Domains in a Rumen Fungal Xylanase: Evidence for Gene Duplication and Prokaryotic Origin" *Molecular Microbiology* 6:2065–2072.

Henrissat et al. (1989) "Cellulase Families Revealed by Hydrophobic Cluster Analysis" *Gene* 81:83–95.

Knowles et al. (1987) "Cellulade Families and Their Genes" *Trends in Biotechnology* 5:255–261.

Kruus et al. (1995) "The Anchorage Function of CipA (CelL), a Scaffolding Protein of the *Clostridium thermocellum* Cellulosome" *Proc. Natl. Acad. Sci. USA* 92:9254–9258.

Lao et al. (1991) "DNA Sequences of Three β–1,4–Endoglucanase Genes from *Thermomonospora fusca*" *Journal of Bacteriology* 173:3397–3407.

Li et al. (1997) GenBank Accession No. U63837. Publication Date: Dec. 29, 1997.

Li et al. (1997) GenBank Accession No. U63838. Publication Date: Dec. 29, 1997.

Li et al. (1997) "Monocentric and Polycentric Anaerobic Fungi Produce Structurally Related Cellulases and Xylanases" *Applied and Environmental Microbiology* 63:628–635.

(List continued on next page.)

*Primary Examiner*—Charles L. Patterson, Jr.
(74) *Attorney, Agent, or Firm*—Greenlee, Winner and Sullivan, P.C.

(57) ABSTRACT

The present invention provides three fungal cellulases, their coding sequences, recombinant DNA molecules comprising the cellulase coding sequences, recombinant host cells and methods for producing same. The present cellulases are from Orpinomyces PC-2.

10 Claims, 22 Drawing Sheets

OTHER PUBLICATIONS

Li and Ljungdahl (1994) "Cloning, Sequencing, and Regulation of a Xylanase Gene from the Fungus *Aureobasidium pullulans* Y-2311-1" *Applied and Environmental Microbiology* 60:3160–3166.

Liu et al. (1996) "Cloning and Characterization of an Endoglucanase Gene from *Orpinomyces joyonii* for Expression in Plant and Microbial Delivery Systems" Abstract. 96th General Meeting of the American Society for Microbiology. 96:505. (1996).

Lowe et al. (1987) "Cellulases and Xylanase of an Anaerobic Rumen Fungus Grown on Wheat Straw, Wheat Straw Holocellulose, Cellulose, and Xylan" *Applied and Environmental Microbiology* 53:1216–1223.

Rouvinen et al. (1990) "Three–Dimensional Structure of Cellobiohydrolase II from *Trichoderma reesei*" *Science* 249:380–386.

Sheppard et al. (1994) "The Use of Conseved Cellulade Family–Specific Sequences to Clone Cellulase Homologue cDNA from *Fusarium oxysorum*" *Gene* 150:163–167.

Shoseyov and Doi (1990) "Essential 170–kDa Subunit for Degradation of Crystalline Cellulose by *Clostridium cellulovorans* Cellulase" *Proc. Natl. Acad. Sci. USA* 87:2192–2195.

Spezio et al. (1993) "Crystal Structure of the Catalytic Domain of a Thermophilic Endocellulase" *Biochemistry* 32:9906–9916.

Teeri et al. (1987) "Homologous Domains in *Trichoderma resei*Cellulolytic Enzymes: Gene Sequence and Expression of Cellobiohydrolase II" *Gene* 51:43–52.

Tempelaars et al. (1994) "Isolation, Characterization, and Analysis of the Expression of the cbhII Gene of *Phanerochaete chrysosporium*" *Applied and Environmental Microbiology* 60:4387–4393.

Tomme et al. (1988) "Studies of the Cellulolytic System of *Trichoderma reesei* QM 9414. Analysis of Domain Function in Two Cellobiohydrolases by Limited Proteolysis"*Eur. J. Biochem.* 170:575–581.

Wang et al. (1993) "Cloning and DNA Sequence of the Gene Coding for *Clostridium thermocellum* Cellulade $S_s$ (CelS), a Major Cellulosome Component" *Journal of Bacteriology* 175:1293–1302.

Wilson and Wood (1992) "Studies on the Cellulase of the Rumen Anaerobic Fungus *Neocallimastix frontalis*, with Special Reference to the Capacity of the Enzyme to Degrade Crystalline Cellulose" *Enzyme Microb. Technol.* 14:258–264.

Wong et al. (1986) "Characterization and Structure of an Endoglucanase Gene cenA of *Cellulomonas fimi*" *Gene* 44:315–324.

Wood et al. (1986) "A Highly Active Extracellular Cellulase from the Anaerobic Rumen Fungus *Neocallimastix frontalis*" *FEMS Microbiology Letters* 34:37–40.

Xue et al. (1992) "Cloning and Expression of Multiple Cellulase cDNAs from the Anaerobic Rumen Fungus *Neocallimastix patriciarum* in *Escherichia coli*" *Journal of General Microbiology* 138:1413–1420.

Xue et al. (1992) "A Novel Polysaccharide Hydrolase cDNA (celD) from *Neocallimastix patriciarum* Encoding Three Multi–Functional Catalytic Domains with High Endoglucanase, Cellobiohydrolase and Xylanase Activities"*Journal of General Microbiology* 138:2397–2403.

Zhou et al. (1994) "Intronless celB from the Anaerobic Fungus *Neocallimastix patriciarum* Encodes a Modular Family A Endoglucanase" *Biochem. J.* 297:359–364.

ATAAGCAATAATTATATATAGAACAATAAATAGAAAAGTTATTTGAATCAACTTTAAAAC
CTACCTATATATAAATAGAAATTTTTTTTTTAGTATTAGAAAAATGAAATTCTCTACTG
                                              M  K  F  S  T         5

TTTTAGCTACTTTATTCGCTACTGGAGCTCTTGCTTCTGAATGTCACTGGCAATACCCAT
 V  L  A  T  L  F  A  T  G  A  L  A  S  E  <u>C  H  W  Q  Y  P</u>    25

GTTGTAAAGATTGTACTGTTTACTACACTGATACTGAAGGTAAGTGGGGTGTTTTAAACA
<u>C  C  K  D  C  T  V  Y  Y  T  D  T  E  G  K  W  G  V  L  N</u>    45

ATGACTGGTGTATGATTGATAACAGACGTTGTAGCAGTAACAACAATAATTGTAGCAGCA
<u>N  D  W  C  M  I  D</u>  N  R  R  <u>C  S  S  N  N  N  C  S  S</u>    65

GTATTACCTCTCAAGGTTACCCATGCTGTAGCAACAATAATTGTAAGGTAGAATACACTG
<u>S  I  T  S  Q  G  Y  P  C  C  S  N  N  N  C  K  V  E  Y  T</u>    85

ATAATGATGGTAAGTGGGGTGTTGAAAACAACAACTGGTGTGGTATTTCCAACAGTTGTG
<u>D  N  D  G  K  W  G  V  E  N  N  N  W  C  G  I  S  N  S  C</u>
105
                    pOC2.1→
GTGGTGGTCAACAACAACAACCAACCCAACCAACTCAACCAACTCAACCACAACAACCAA
<u>G  G  G  Q  Q  Q  Q  P  T  Q  P  T  Q  P  T  Q  P  Q  Q  P</u>   125

CTCAACCAAGTAGTGATAACTTCTTTGAAAATGAAATTTACAGTAACTACAAGTTCCAAG
<u>T  Q  P  S  S</u>  D  N  F  F  E  N  E  I  Y  S  N  Y  K  F  Q    145

GAGAAGTTGATATTTCTATTAAGAAATTAAATGGTGACTTAAAGGCTAAGGCTGAAAAGG
 G  E  V  D  I  S  I  K  K  L  N  G  D  L  K  A  K  A  E  K    165

TCAAATATGTTCCAACGGCTGTTTGGTTAGCTTGGGATGGTGCTCCACAAGAAGTTCCAA
 V  K  Y  V  P  T  A  V  W  L  A  W  D  G  A  P  Q  E  V  P    185

GATACCTTCAAGAAGCTGGTAACAAGACTGTTGTTTTCGTCTTATATATGATTCCAACTC
 R  Y  L  Q  E  A  G  N  K  T  V  V  F  V  L  Y  M  I  P  T    205

GTGATTGTGGTGCTAACGCTTCTGCTGGTGGTTCTGCTACCATCGATAAATACAAGGGTT
  R  D  C  G  A  N  A  S  A  G  G  S  A  T  I  D  K  Y  K  G   225

ACATTAACAACATTTACAACACTTCCAACCAATACAAGAACTCTAAAATTGTTATGATTC
 Y  I  N  N  I  Y  N  T  S  N  Q  Y  K  N  S  K  I  V  M  I    245

TTGAACCAGATACTATTGGTAACCTTGTTACTAACAACAACGATAACTGTAGAAATGTCA
 L  E  P  D  T  I  G  N  L  V  T  N  N  D  N  C  R  N  V    265

GAAACATGCACAAACAAGCCCTTTCTTACGCTATTAGTAAGTTCGGTACTCAAAGTCACG
 R  N  M  H  K  Q  A  L  S  Y  A  I  S  K  F  G  T  Q  S  H    285

FIG. 2A

```
TCAAGGTTTACCTTGATGCTGCTCACGGTGCTTGGTTAAACCAATACGCTGATCAAACAG
 V  K  V  Y  L  D  A  A  H  G  A  W  L  N  Q  Y  A  D  Q  T     305

CTAATGTCATTAAGGAAATCTTAAATAACGCTGGTAGTGGTAAGCTTCGTGGTATTAGTA
 A  N  V  I  K  E  I  L  N  N  A  G  S  G  K  L  R  G  I  S     325

CTAATGTTTCTAACTACCAATCCATTGAAAGTGAATACAAATACCATCAAAACCTTAACA
 T  N  V  S  N  Y  Q  S  I  E  S  E  Y  K  Y  H  Q  N  L  N     345

GAGCCCTTGAAAGTAAAGGTGTCAGAGGTCTTAAGTTCATTGTCGATACTTCTCGTAACG
 R  A  L  E  S  K  G  V  R  G  L  K  F  I  V  D  T  S  R  N     365

GTGCTAACGTTGAAGGTGCTTTCAATGCCTCCGGTACCTGGTGTAACTTCAAGGGTGCTG
  G  A  N  V  E  G  A  F  N  A  S  G  T  W  C  N  F  K  G  A    385

GTTTAGGTCAACGTCCAAAGGGTAATCCAAACCCAGGTAGCATGCCATTACTTGATGCCT
 G  L  G  Q  R  P  K  G  N  P  N  P  G  S  M  P  L  L  D  A     405

ACATGTGGATTAAGACTCCAGGTGAAGCTGATGGTTCTTCCCAAGGTTCAAGAGCTGATC
 Y  M  W  I  K  T  P  G  E  A  D  G  S  S  Q  G  S  R  A  D     425

CAGTTTGTGCTCGTGGTGATTCTCTCCAAGGTGCTCCAGATGCTGGTTCATGGTTCCACG
 P  V  C  A  R  G  D  S  L  Q  G  A  P  D  A  G  S  W  F  H     445

AATACTTCACCATGTTAATCCAAAACGCTAACCCACCATTCTAAGTTAATCATAAATGAG
 E  Y  F  T  M  L  I  Q  N  A  N  P  P  F  *                    459

AAAAGAATAAAATTATACATGTAGAAGAAAATTTTTATTTTTATTTATTCTAAAAAA
```

FIG. 2B

```
ATTAAAATAGCTTAAATATTATATTCATATTCACTGGTTGAATTGTTATAATATTATATA
ATAAAACTGTGTATTTATATAAAAAAAAATTATTTATCATTTAATAATATAAATAAATTA
TTAAAAAAAAAAAAAAATAAATTTTTATAAAAAATGAAATTCTCTGCTTTAATTAGTACT
                                    M  K  F  S  A  L  I  S  T         9

TTATTTGCTGCTGGAGCTATGGCCTCCAGATGTCATCCAAGTTACCCATGTTGTAACGGT
 L  F  A  A  G  A  M  A  S  R  C  H  P  S  Y  P  C  C  N  G          29

TGTAACGTTGAATACACTGATACTGAAGGTAATTGGGGTGTAGAAAATTTTGATTGGTGT
 C  N  V  E  Y  T  D  T  E  G  N  W  G  V  E  N  F  D  W  C          49

TTCATTGATGAAAGCCGTTGTAATCCAGGATACTGTAAATTCGAAGCTCTTGGTTACAGT
 F  I  D  E  S  R  C  N  P  G  Y  C  K  F  E  A  L  G  Y  S          69

TGCTGTAAGGGATGTGAAGTTGTTTACTCTGATGAAGATGGTAATTGGGGTGTTGAAAAC
 C  C  K  G  C  E  V  V  Y  S  D  E  D  G  N  W  G  V  E  N          89

CAACAATGGTGTGGTATTAGAGATAACTGTACTCCAAATGTTCCAGCCACTAGTGCTAGA
 Q  Q  W  C  G  I  R  D  N  C  T  P  N  V  P  A  T  S  A  R         109

ACCACTACCAGAACTACTACTACTACTAGAACTACTACTGTTAACTCTCTTCCAACTAGC
 T  T  T  R  T  T  T  T  T  R  T  T  T  V  N  S  L  P  T  S         129

GACAACTTCTTTGAAAATGAACTTTACAGTAACTACAAATTCCAAGGTGAAGTTGACCAA
 D  N  F  F  E  N  E  L  Y  S  N  Y  K  F  Q  G  E  V  D  Q         149

TCTATTCAAAGATTAAGTGGTTCTTTACAAGAAAAGGCTAAGAAAGTTAAGTACGTTCCA
 S  I  Q  R  L  S  G  S  L  Q  E  K  A  K  K  V  K  Y  V  P         169

ACTGCTGCTTGGTTAGCTTGGAGTGGTGCTACAAATGAAGTTGCAAGATACCTTAATGAA
 T  A  A  W  L  A  W  S  G  A  T  N  E  V  A  R  Y  L  N  E         189

GCTGGTTCAAAGACTGTTGTCTTCGTTTTATATATGATTCCAACTCGTGATTGTAATGCT
 A  G  S  K  T  V  V  F  V  L  Y  M  I  P  T  R  D  C  N  A         209

GGTGGTTCTAATGGTGGTGCTGATAACCTTTCTACATACCAAGGATACGTTAACAGTATC
 G  G  S  N  G  G  A  D  N  L  S  T  Y  Q  G  Y  V  N  S  I         229

TACAACACTATTAACCAATATCCAAACTCTAGAATCGTTATGATTATTGAACCAGATACT
 Y  N  T  I  N  Q  Y  P  N  S  R  I  V  M  I  I  E  P  D  T         249

ATTGGTAATCTTGTTACTGCTAACAATGCTAACTGTAGAAATGTCCATGACATGCACAAA
 I  G  N  L  V  T  A  N  N  A  N  C  R  N  V  H  D  M  H  K         269

CAAGCTCTTTCCTATGCTATTAGTAAGTTCGGTACTCAAAAGAACGTTAGAGTTTACCTT
 Q  A  L  S  Y  A  I  S  K  F  G  T  Q  K  N  V  R  V  Y  L         289
```

FIG. 3A

```
GATGCTGCTCACGGTGGTTGGTTAAACAGCAGTGCTGACAGAACTGCTGAAGTTATTGCT
 D   A   A   H   G   G   W   L   N   S   S   A   D   R   T   A   E   V   I   A    309

GAAATTTTAAGAAATGCTGGTAATGGTAAGATTCGTGGTATTAGTACTAATGTTTCTAAC
 E   I   L   R   N   A   G   N   G   K   I   R   G   I   S   T   N   V   S   N    329

TACCAACCAGTTTACAGTGAATACCAATATCACCAAAACCTTAACAGAGCTCTTGAAAGT
 Y   Q   P   V   Y   S   E   Y   Q   Y   H   Q   N   L   N   R   A   L   E   S    349

AGAGGTGTTCGCGGTATGAAATTCATTGTTGATACTTCTCGTAACGGTAGAAACCCATCT
 R   G   V   R   G   M   K   F   I   V   D   T   S   R   N   G   R   N   P   S    369

TCTGCTACCTGGTGTAACCTTAAGGGTGCTGGTTTAGGTGCTCGTCCACAAGCTAACCCA
 S   A   T   W   C   N   L   K   G   A   G   L   G   A   R   P   Q   A   N   P    389

GATCCAAATATGCCATTACTTGATGCTTATGTTTGGATTAAAACTCCAGGTGAATCTGAC
 D   P   N   M   P   L   L   D   A   Y   V   W   I   K   T   P   G   E   S   D    409

AGTGCTTCCAGTGCTGATCCAGTTTGCCGTAACAGCGACTCTTTACAAGGTGCTCCAGCT
 S   A   S   S   A   D   P   V   C   R   N   S   D   S   L   Q   G   A   P   A    429

GCTGGTTCATGGTTCCACGATTACTTTGTTATGTTATTAGAAAATGCTAACCCACCATTC
 A   G   S   W   F   H   D   Y   F   V   M   L   L   E   N   A   N   P   P   F    449

TAAGCAATTAAAAATACCTTTATATTTTAAGATAATTAATATAAAATAGAAAGAAAATT
  *
TTATTTTTTCTATTTAATTTAGAAATGTATTATTAATAATTAAAATTTAGAAGGGAAAAA
GAAAAAAA
```

FIG. 3B

```
Cela_Orpin      20   CH.W...Q.YPCC.K.DCTVYYTDTEGKWGVLNNDWCMID
Celc_Orpin      20   CH.P....SYPCC.N.GCNVEYTDTEGNWGVENFDWCFID
Celb_Orpin     390   C..FSTRLGYSCC.N.GFDVLYTDNDGQWGVENGNWCGIK
Celb_Neopa     392   C..FSVNLGYSCC.N.GCEVEYTDSDGEWGVENGNWCGIK
Xyna_Orpin     279   CSAKITAQGYKCCSDPNCVVYYTDEDGTWGVENNQWCGCG
Xyla-Neopa     524   CSARITAQGYKCCSDPNCVVYYTDEDGTWGVENNDWCGCG
Xyla_Pirom     286   CPSTITSQGYKCCSS.NCDIIYRDQSGDWGVENDEWCGCG
Mana_Pirom     492   CWS..INLGYPCCIG.DY.VVTTDENGDWGVENNEWCGIV
Cela_Orpin-2    63   CSSSITSQGYPCCSNNNCKVEYTDNDGKWGVENNNWCGIS
Celc_Orpin-2    61   C..KFEALGYSCCK..GCEVVYSDEDGNWGVENQQWCGIR
Celb_Orpin-2   435   CWS..ERLGYPCCQY.TTNAEYTDNDGRWGVENGNWCGIY
Celb_Neopa-2   437   CWS..EKLGYPCCQN.TSSVVYTDNDGKWGVENGNWCGIY
Xyna_Orpin-2   322   CSGKITAQGYKCCSDPKCVVYYTDDDGKWGVENNEWCGCG
Xyla_Neopa-2   567   CSSKITSQGYKCCSDPNCVVFYTDDDGKWGVENNDWCGCG
Xyla_Pirom-2   333   CPSSIKNQGYKCCSD.SCEIVLTDSGDWGIENDEWCGCG
Mana_Pirom-2   531   CWS..EPLGYPCCVG.NT.VISADESGDWGVENNEWCGIV
Mana-Pirom-3   570   CWA..EFLGYPCCVG.NT.VISTDEFGDWGVENDDWCGIL
```

```
Cela_Orpin  370 KGAFNASGTWCNFKGAGLGQRPKGNPNPGSMPLLDAYMWIKTPGEADGSSQGSRA..DPVCARGDSLQGAPDAGSWFHEYFTMLIQNANPPF.
Celc_Orpin  369 .....SSATWCNLKGAGLGARPQANPDPN.MPLLDAYVWIKTPGESDS..ASSA..DPVCRNSDSLQGAPAAGSWFHDYFVMLLENANPPF.
Cela_Neopa  325 .....NSGTWCNLVGTGLGERPRGNPNAG.MPLLDAYMWLKTPGESDGSSSGSRA..DPNCSSNDSLRGAPDAGQWFHDYFAQLVRNARPSF
Cbhii_Trire 383 TGQ.QQWGDWCNVIGTGFGIRPSANTGDS...LLDSFVWVKPGGECDGTSDSSAPRFDSHGALPDALQPAPQAGAWFQAYFVQLLTNANPSFL
Cbhb_Fusox  374 TGQ.KAQGDWCNAKGTGFGLRPSTNTGDA...LADAFVWVKPGGESDGTSDTSAARYDYHCGLDDALKPAPEAGTWFQAYFEQLLDNANPSFL
Cbhii_Agabi 352 I.R.DQWGDWCNVKGAGFGQRPTTNTGSS...LIDAIVWVKPGGECDGTSDNSSPRFDSHCSLSDAHQPAPEAGTWFQAYFETLVANANPAL.
Cela_Celfi  386 NG......EWCNPRGRALGERPVAVNDG...SGLDALLWVKLPGESDGACN...........GGPAAGQWWQEIALEMARNARW...
Cela2_Thefu 258 AG......NKWCDPSGRAIGTPSTTNTGD...PMIDAFLWIKLPGEADGC...........IAGAGQFVPQAAYEMAIAAGGHQ.
Celi_Strsp  301 LG......SKWCDPPGRLVGNNPTVNPGV...PGVDAFLWIKLPGELDGC...........DGPVGSFSPAKAYELAGG......
consensus   280                             **     * *    ** * ** ***                     *
```

FIG. 5B

TAATCTTCTCTTATTTTTTTCTTTTCTATAATTAATAAAAAAATTAAAATATTAAAAATGAAATTCTTAAATAGTCTT    7
                                                      M  K  F  L  N  S  L

TCTTTACTTGGATTAGTTATTGCTGGATGTGAAGCTATGAGAAATATTAGTAGTTAAAGAATTAGTTAAAGAATTAACTATTGGTTGGAGT   37
 S  L  L  G  L  V  I  A  G  C  E  A  M  R  N  I  S  S  K  E  L  V  K  E  L  T  I  G  W  S

TTAGGTAATACCTTAGATGCATCCTGTGTGGAGACTTTAAATTATAGTAAAGATCAAACAGCTTCTGAAACTTGTTGGGGTAATGTTAAA   67
 L  G  N  T  L  D  A  S  C  V  E  T  L  N  Y  S  K  D  Q  T  A  S  E  T  C  W  G  N  V  K

ACTACTCAAGAGCTTTACTATAAACTTAGTGATCTTGGTTTCAACACTTTCCGTATTCCTACTACTTGGAGTGGTCATTTTGGTGATGCT   97
 T  T  Q  E  L  Y  Y  K  L  S  D  L  G  F  N  T  F  R  I  P  T  T  W  S  G  H  F  G  D  A

CCTGACTATAAAATTAGTGATGTTTGGATGAAAAGAGTTCATGAAGTTGTCGATTATGCTCTTAACACTGGTGGTTATGCCATCTTAAAC   127
 P  D  Y  K  I  S  D  V  W  M  K  R  V  H  E  V  V  D  Y  A  L  N  T  G  G  Y  A  I  L  N

ATTCACCATGAAACTTGGAATTATGCTTTCCAAAAGAATTTAGAGAGTGCCAAAAAGATCTTAGTTGCCATCTGGAAACAAATTGCTGCT   157
 I  H  H  E  T  W  N  Y  A  F  Q  K  N  L  E  S  A  K  K  I  L  V  A  I  W  K  Q  I  A  A

GAATTTGGTGATTATGATGAACATTAATTTCGAAGGAATGAATGAACCAAGAAAAGGTTGGGGATCCAGCTGAATGGACAGGTGGTGAT   187
 E  F  G  D  Y  D  E  H  L  I  F  E  G  M  N  E  P  R  K  V  G  D  P  A  E  W  T  G  G  D

CAAGAAGGTTGGAATTTCGTCAATGAAATGAATGCCCTTTTCGTTAAAACTATTCGTGCCACTGGAGGTAACAATGCCAATCGTCATCTT   217
 Q  E  G  W  N  F  V  N  E  M  N  A  L  F  V  K  T  I  R  A  T  G  G  N  N  A  N  R  H  L

ATGATTCCAACCTATGCTGCCTCTGTTAATGATGGTTCAATTAATTTCAAATATCCAAATGGGGATGATAAAGTCATTGTTTCCCTT   237
 M  I  P  T  Y  A  A  S  V  N  D  G  S  I  N  F  K  Y  P  N  G  D  D  K  V  I  V  S  L

CATTCCTACAGTCCATACAATTTGCCTTAAATAATGGTCCAGGTGCTATCAGTAATTTTATGATGGTAATGAAATTGATTGGGTCATG   267
 H  S  Y  S  P  Y  N  F  A  L  N  N  G  P  G  A  I  S  N  F  Y  D  G  N  E  I  D  W  V  M

FIG. 10A

```
AATACTATTAACTCCTCCTTCATCAGCAAGTATTCCTGTCATCATTGGTGAATTTGTTGCTATGAACCGTGACAATGAAGATGACCGT  297
 N  T  I  N  S  S  F  I  S  K  G  I  P  V  I  I  G  E  F  V  A  M  N  R  D  N  E  D  D  R
GACGAAAGATGGCAAGAATATTATATTAAGAAAGCCACTGCTCTTGGTATTCCATGTGTTATCTGGGATAATGGTTACTTTGAGGGTGAAGGT  327
 E  R  W  Q  E  Y  Y  I  K  K  A  T  A  L  G  I  P  C  V  I  W  D  N  G  Y  F  E  G  E  G
GAACGCTTTGGTATCATTGATCGTAAATCCTTAAATGTCATTTTCCCAAAACTTATCAATGGTTTAATGAAAGGTTTAGGTGATGAGAAG  367
 E  R  F  G  I  I  D  R  K  S  L  N  V  I  F  P  K  L  I  N  G  L  M  K  G  L  G  D  E  K
CCAAAGACTACAATAAGAAGAACTACCACTACTACTGTTCAAGTCCAACCAACTATTAATGAATGCTTCAGTACTAGACTTGGTTAC  397
 P  K  T  T  I  R  R  T  T  T  T  V  Q  V  Q  P  T  I  N  N  E  C  F  S  T  R  L  G  Y
AGCTGTTGTAATGGTTTTGATGTCTTGTACACTGATAATGATGGACAATGGGGTGTTGAAAACGGCAATTGGTGTGGTATTAAGTCATCT  427
 S  C  C  N  G  F  D  V  L  Y  T  D  N  D  G  Q  W  G  V  E  N  G  N  W  C  G  I  K  S  S
TGTGGTAACAATCAACGTCAATGCTGGTCTGAAAGACTTGGTTACCCATGTGTCAATATACCACCATGCTGAATACACCGATAATGAT  457
 C  G  N  N  Q  R  Q  C  W  S  E  R  L  G  Y  P  C  C  Q  Y  T  N  A  E  Y  T  D  N  D
GGTAGATGGGGTGTTGAAAATGGTAATTGGTGTGGTATTTATTAACTTACTAAATAATTTTTACAAACATAAATAATTATTAGTAAA
 G  R  W  G  V  E  N  G  N  W  C  G  I  Y  *
ATAAAAAAGAATAAATTTTAAAAAAATATATTTATATATTATGTTATAAAATAATAATAATAGAAATTACTATAGTATATAGA
AATATATACATAAACAAAAGTAAAAATTAAAAATTTTTAGTATTGTATAAATTTTATTAAAAGTTAATAAATGATAAAAAAATA
TTAAACATTTGGATGTATTTGCATATCAAAGAAATAAATACTTTAAAGCATAAATTGATAAATAATTCATAATTCATAAACACAT
ACTTTTAAACAATTTTAAAATAAAA
```

FIG. 10B

```
GGCACGAGGAAATTTTTTTACTGGTTAAAAAAAAATTATAAAACTAAATAAAAAAAAATATTTTTGAAATATATTAAAATAGGAA

AAAAAATGAGAACTATTAAATTTTTATTCGCATTAGCTATTACAACCGTGCTAAGGCCCAATGGGTGAAACGTGGTGCCTCTGCT                28
          M  R  T  I  K  F  L  F  A  L  A  I  T  T  V  A  K  A  Q  W  G  G  N  G  G  A  S  A

GGTCAAAGATTAAGCGTTGGTGGTGTCAAAACCAACATAAAGGTGTTTTTGATGGCTTCAGTTATGAAATCTGTTAGATAACACCGGT              58
 G  Q  R  L  S  V  G  G  G  Q  N  Q  H  K  G  V  F  D  G  F  S  Y  E  I  W  L  D  N  T  G

GGTAGTGGTTCCATGACCCTTGGTAAAGGTGCAACCTTCAAGGCTGAGTGCAGCGTGTAACCGTGTAACTTCCTTGCCCGTCGT                  88
 G  S  G  S  M  T  L  G  K  G  A  T  F  K  A  E  W  S  A  A  V  N  R  G  N  F  L  A  R  R

GGTCTTGATTTCGGTTCTACCAAAAAGGCAACCGCTTACGAATACATGGATTATGAAGCAAGTTACAGACAAACTGCCAGCGCA                118
 G  L  D  F  G  S  T  K  K  A  T  A  Y  E  Y  I  G  L  D  Y  E  A  S  Y  R  Q  T  A  S  A

AGTGGTAACTCCCGTCTCTTGTGTATACGGCTGGTTCCAAAACCGTGAGTTCAAGGCCGTACCTTTGGTAGAATACTACATCATTGAAGAT         148
 S  G  N  S  R  L  C  V  Y  G  W  F  Q  N  R  G  V  Q  G  V  P  L  V  E  Y  Y  I  I  E  D

TGGGTTGACTGGGTACCAGATGCCACAAGGAAAAATGGTAACCATGATGGTGCACAATATAAGATTTTCCAAATGGATCACACTGGTCCA          178
 W  V  D  W  V  P  D  A  Q  G  K  M  V  T  I  D  G  A  Q  Y  K  I  F  Q  M  D  H  T  G  P

ACTATCAATGGTGGTAATGAAACCTTTAAGCAATATTTCTCTGTCAATATTACTGTATCAGATCAC                                   208
 T  I  N  G  G  N  E  T  F  K  Q  Y  F  S  V  R  Q  Q  K  R  T  S  G  H  I  T  V  S  D  H

TTTAAGGCATGGTCCAATCAAGGTTGGGGTATTGGAAACCTCTATGAAGTTGCATTGAACGCAGAAGGTTGGCAAAGTAGTGGTGTCGCT          238
 F  K  A  W  S  N  Q  G  W  G  I  G  N  L  Y  E  V  A  L  N  A  E  G  W  Q  S  S  G  V  A gacgtccccaagttggatgtctacacaccaaacaaggttctgtcctcgtactactaccaccactaccccgtactactaccgtactact              268
 D  V  P  K  L  D  V  Y  T  T  K  Q  G  S  A  P  R  T  T  T  T  T  T  T  R  T  T
```

FIG. 11A

```
ACAAAAACACTTCCAACCACTAATAAAAAAATGTTCTGCCAAGATTACTGCCCAAGGTTACAAGTGTTGTAGTGATCCAAATTGTGTTGTT    298
 T  K  T  L  P  T  T  N  K  K  C  S  A  K  I  T  A  Q  G  Y  K  C  C  S  D  P  N  C  V  V

TACTACACTGATGAAGATGGTACCTGGGGTGTTGAAAACAATCAATGGTGTGGATGTGGTGTTGAAGCATGTTCTGGCAAGATTACTGCC    328
 Y  Y  T  D  E  D  G  T  W  G  V  E  N  N  Q  W  C  G  C  G  V  E  A  C  S  G  K  I  T  A

CAAGGTTACAAGTGTTGTAGTGATCCAAGTGTGTTGTTTACTACACTGATGACGATGGTAAATGGGGTGTTGAAAACAACGAATGGTGT    358
 Q  G  Y  K  C  C  S  D  P  K  C  V  V  Y  T  D  D  D  G  K  W  G  V  E  N  N  E  W  C

GGTTGTGGTTTATAAGCAGAAAAATACTAATTTAGTAAAAAAAAAAAA
 G  C  G  L  *
```

FIG. 11B

```
O-CelB  MKFLNSLSLLGLVIAGCEAMRNISSKELVKELTIGWSLGNTLDASCVETLNYSKDQTASETCWGNVKTTQELYYK  75
        ||||||| ||||| ||:| ||||||| ||||||:||||||||| ||| :|||||||:|||||||||||||||
N-CelB  MKFLNTFSLLSLAIIGSKAMKNISSKELVKDLTIGWSLGNTLDATCFETLDYNKNQIASETCWGNVKTTQELYYK  75

O-CelB  LSDLGFNTFRIPTTWSGHFGDAPDYKISDVVMKRVHEVVDYAILNIHHETWNYAFQKNLESAKKILVA  150
        || |||||||||||||||||| ||||| | ||||||||:|||||||||||||||||||||||||||
N-CelB  LSKLGFNTFRIPTTWSGHFGNAPDYKINDQWMKRVHEIVDYAINTGGYAILNIHHETWNHAFQKNLESAKKILVA  150

O-CelB  IWKQIAAEFGDYDEHLIFEGMNEPRKVGDPAEWTGGDQEGWNFVNEMNALFVKTIRATGGNNANRHLMIPTYAAS  225
        ||||||||| ||||||||||||||||||||||||| : |||||||||||:|||||||||||||| ||||||| :
N-CelB  IWKQIAAEFADYDEHLIFEGMNEPRKVGDPAEWNGGDESGWNFVNEMNDLFVKTIRATGGNNALRHLMIPTYAAC  225

O-CelB  VNDGSINNFKYPNGDDKVIVSLHSYSPYNFALNNGPGAISNFYDGNEIDWVMNTINSSFISKGIPVIIGEFVAMN  300
        :||| ||||||| |||||||||||||||||||||| |||||||| |||| |||||| ||| |||||||||| ||
N-CelB  INDGAINNFKFPSGDDKVIVSLHSYSPYNFALNNGAGAISNFYDGSEIDWAMNTINSKFISRGIPVIIGEFGAMN  300

O-CelB  RDNEDDRERWQEYYIKKATALGIPCVIWDNGYFEGEGERFGIIDRKSLNVIFPKLINGLMKGLGDE.KPKTTIRR  374
        |:|||||||| |||||||||:|||||||||||||||||||| ||:|||| |||| ||||::||||: |||||||
N-CelB  RNNEDDRERWAEYYIKKATSIGVPCVIWDNGYFEGEGERFGLINRSTLQVVYPKLVNGLIKGLGNSIKTRTTIRR  375

O-CelB  TTTTTV.QVQPTINNECFSTRLGYSCCNGFDVLYTDNDGQWGVENGNWCGIKSSCGNNQRQCWSERLGYPCCQYT  448
        ::|||| |||||||||:|| || || |||: :|:|||:|:|||||||||||||||||| | || |||||| |:
N-CelB  TTTTTTSQSQPTNNDSCFSVNLGYSCCNGCEVEYTDSDGEWGVENGNWCGIKSSCSNTSRICWSEKLGYPCCQNT  450

O-CelB  TNAEYTDNDGRWGVENGNWCGIY  471
        :: |||||||:||||||||||||
N-CelB  SSVVYTDNDGKWGVENGNWCGIY  473
```

FIG. 12

RP1
```
Orpinomyces CelB      CF..STRLGYSCC.NG.FDVLYTDNDGQWGVENGNWCGIK
Neocallimastix CelB   CF..SVNLGYSCC.NG.CEVEYTDSDGEWGVENGNWCGIK
Orpinomyces XynA      CSAKITAQGYKCCSDPNCVVYTDEDGTWGVENNQWCGCG
Neocallimastix XYLA   CSARITAQGYKCCSDPNCVVYYTDEDGTWGVENNDWCGCG
Piromyces XYLA        CPSTITSQGYKCCSS.NCDIIYRDQSGDWGVENDEWCGCG
Piromyces MANA        CWS.INL.GYPCCIG..DYVVTTDENGDWGVENNEWCGIV
```

RP2
```
Orpinomyces CelB      CW..SERLGYPCCQYTTNAE.YTDNDGRWGVENGNWCGIY
Neocallimastix CelB   CWS..EKLGYPCCQNTSSVV.YTDNDGKWGVENGNWCGIY
Orpinomyces XynA      CSGKITAQGYKCCSDPKCVVYTDDDGKWGVENNEWCGCG
Neocallimastix XYLA   CSSKITSQGYKCCSDPNCVVFYTDDDGKWGVENNDWCGCG
Piromyces XYLA        CPSSIKNQGYKCCSDSCEIVL.TDSDGDWGIENDEWCGCG
Piromyces MANA        CWSEPL..GYPCCVGNTVIS..ADESGDWGVENNEWCGIV
```

RP3
```
Piromyces MANA        CWAEFL..GYPCCVGNTVIS..TDEFGDWGVENDDWCGIL
```

CELLULASES AND CODING SEQUENCES

CROSS REFERENCE TO RELATED APPLICATIONS

This application is a continuation-in-part of International Patent Application PCT/US97/18008, filed Oct. 3, 1997, which claims priority from United States Provisional Application Ser. No. 60/027,883, filed Oct. 4, 1996.

ACKNOWLEDGMENT OF FEDERAL RESEARCH SUPPORT

This invention was made, at least in part, with funding from the United States Department of Energy. Accordingly, the United States Government has certain rights in this invention.

BACKGROUND OF THE INVENTION

The field of the present invention is the area of cellulolytic enzymes, nucleotide sequences encoding them and recombinant host cells and methods for producing them.

Cellulose, the most abundant structure of plant cell walls, exists mostly as insoluble microfibril which are formed by hydrogen bonds between individual cellulose chains. Conversion of cellulose to glucose provides readily available carbon sources for fuel and chemical production. Such conversion requires several types of enzymes including endoglucanases (E.C. 3.2.1.4), cellobiohydrolases (also called exoglucanase, E.C. 3.2.1.91), β-glucosidase (also called cellobiase, E.C. 3.2.1.21). Endoglucanases hydrolyze β-glycoside bonds internally and randomly along the cellulose chains whereas cellobiohydrolases remove cellobiose molecules from the reducing and non-reducing ends of the chains (Barr et al., 1996). β-Glucosidases hydrolyze the cellobiose to two molecules of glucose, and therefore eliminate the inhibition of cellobiose on cellobiohydrolases and endoglucanases.

Microorganisms have evolved diverse strategies for efficient break down of plant cell wall constitutes, particularly cellulose. Aerobic organisms tend to secrete individual enzymes whereas some anaerobic bacteria produce high molecular weight enzyme complexes on the cell surface. Examples of such enzyme producers are the fungus *Trichoderma reesei* and bacteria *Cellulomonas fimi* and *Thermomonospora fusca*. Cellulases of these organisms consist of cellulose binding domains (CBD) and catalytic domains joined by linker sequences. Anaerobic bacteria whose cellulolytic systems received extensive investigations include *Clostridium thermocellum* (Felix and Ljungdahl. 1993. Ann. Rev. Microbiol. 47:791–819; Aubert et al. 1993. In: M. Sebald (ed.) Genetics and Molecular Biology of Anaerobic Bacteria. p. 412–422. Springer-Verlag, NY) and *C. cellulovorans* (Doi et al. 1994. Crit. Rev. Microbiol. 20:87–93). The high molecular weight cellulase complex, more often called the cellulosome, of *C. thermocellum* contains about 26 polypeptides with a mass in a range of $2 \times 10^6$ to $6.5 \times 10^6$ Da (Lamed et al., 1983). These polypeptides include at least one scaffolding protein termed cellulosome integrating protein A (CipA) and a number of catalytically active proteins. The protein and protein interactions forming the cellulosome are effected by conserved duplicated regions (CDR) of the catalytically active proteins and nine internal repeated elements (IRE) of CipA.

Highly efficient cellulases of anaerobic fungi have been demonstrated (Wood et al. 1986 FEMS Microbiol Lett. 34:37–40; Lowe et al. 1987. Appl. Environ. Microbiol. 53:1216–1223; Borneman et al. 1989. Appl. Environ. Microbiol. 55:1066–1073). A high molecular weight cellulase/hemicellulase complex has been isolated from *Neocallimastix frontalis* (Wilson and Wood. 1992. Enzyme Microb. Technol. 14:258–264). No individual native cellulases have been purified from anaerobic fungi. On the basis of morphology of sporangia, mycelia and zoospores;, anaerobic fungi have been classified into two groups, monocentric and polycentric (Borneman et al., 1989, supra; Borneman and Akin. 1994. Mycoscience 35:199–211). Monocentric fungi have only one sporangium developed from one zoosporium, whereas polycentric isolates have multiple sporangia originating from one zoosporium. Most investigations on anaerobic fungi have focused on monocentric isolates, particularly isolates of the genera Neocallimastix and Piromyces. Gene cloning and sequencing of polysaccharidases from the monocentric anaerobic fungi have shown that multiple cellulases and hemicellulases of these fungi may form high molecular weight complexes (HMWC) similar to the cellulosomes of Clostridia (Gilbert et al. 1992. Mol. Microbiol. 6:2065–2072; Zhou et al. 1994. Biochem. J. 297:359–364, Fanutti et al. 1995. J. Biol. Chem. 270:29314–29322). Evidence provided by these studies is three fold: 1) Most of the hydrolases lack cellulose binding domains; 2) They have repeated peptide (RP) domains at the carboxyl termini or between two catalytic domains although they lack sequence homology with the CDRs of cellulosomal catalytic proteins. These regions are not required for catalysis; and 3) The RP domain of a Piromyces xylanase binds to other proteins in the Neocallimastix and Piromyces HMWCs. More recently, however, a cellulase (CelA) of Neocallimastix, which lacks the RP domain but contains a typical fungal CBD and a cellobiohydrase catalytic domain, has been reported (Denman et al., 1996).

By contrast, the polysaccharide hydrolyzing enzymes of aerobic fungi are generally secreted as individual enzymes, including endoglucanases, cellobiohydrolases and β-glucosidase which act synergistically on the substrate.

SUMMARY OF THE INVENTION

It is an object of the invention to provide a cellulase coding sequence for a cellulase selected from the group consisting of CelA, CelB and CelC. Besides the specifically exemplified coding sequences isolated from Orpinomyces PC2, the present invention also encompasses all synonymous coding sequences for each of the exemplified amino acid sequences disclosed herein and coding sequences for cellulase enzymes having at least about 90% amino acid sequence identity with an exemplified sequence.

Also provided by the present invention are recombinant host cells genetically engineered to contain and express the foregoing cellulase coding sequences. Such recombinant host cells can be fungal or bacterial. Preferred fungal host cells include, but are not limited to, *Saccharomyces cerevisiae, Aspergillus niger,* Aspergillus, Penicillium, *Pichia pastoris* and *Trichoderma reesei*. Bacterial host cells for cellulase expression can include *Bacillus subtilis, Bacillus stearothermophilus, Escherichia coli* and *Staphylococcus aureus* and Streptomyces, among others.

It is a further object of this invention to provide purified cellulase enzymes (CelA, CelB and CelC) as defined herein. As specifically exemplified, CelA, CelB and CelC have amino acid sequences as provided in SEQ ID NO:2, SEQ ID NO:12 and SEQ ID NO:4. Cellulases of equivalent biological activity and enzymatic specificity having at least about 75% amino acid sequence identity with the exemplified CelA and CelC sequences and at least about 85% amino acid sequence identity with the exemplified CelB are within the scope of the present invention.

BRIEF DESCRIPTION OF THE DRAWINGS

FIG. 2 gives the nucleotide sequence (SEQ ID NO:1) and deduced amino acid sequence (SEQ ID NO:2) of Orpinomyces celA cDNA (pLIC5). The RPs of the non-catalytic domain and linker sequences are underlined and double-underlined, respectively. The 5' end of pOC2.1 is shown. *, stop codon.

FIG. 3 gives the nucleotide sequence (SEQ ID NO:3) and deduced amino acid sequence (SEQ ID NO:4) of Orpinomyces celC cDNA (pLIC8). The RPs of the non-catalytic domain and linker sequences are underlined and double-underlined, respectively. *, stop codon.

FIG. 4 illustrates amino acid alignment of the RPs of the non-catalytic domains of polysaccharide hydrolases of anaerobic fungi. Cela_Orpin, Orpinomyces CelA (amino acids 20–59 and 63–102 of SEQ ID NO:2); Celc_Orpin, Orpinomyces CelC (amino acids 20–∇and 63–102 of SEQ ID NO:4); Celb_Orpin, Orpinomyces CelB (amino acids 390–429 and 435–447 of SEQ ID NO:12); Celb_Neopa, Neocallimastix patriciarum CelB (amino acids 392–421 and 437–476 of SEQ ID NO:15) (Zhou et al., 1994, supra); Xyna_Orpin, Orpinomyces XynA (amino acids 279–318 and 322–461 of SEQ ID NO:14); Xyla_Neopa, N. patriciarum XYLA (SEQ ID NO:16 and SEQ ID NO:17) (Gilbert et al., 1992, supra); Xyla_Pirom, Piromyces XYLA (SEQ ID NO:18 and NO:19) (Fanutti et al., 1995); Mana_Pirom, Piromyces MANA (SEQ ID NO:20, NO:21 and NO:22) (Fanutti et al., 1995).

FIG. 5 illustrates an alignment of the amino acid sequences of the catalytic domains of Orpinomyces CelA and CelC with other family B cellulases (amino acids 128–459 of SEQ ID NO:2 and amino acids 127–449 of SEQ ID NO:4, respectively). Sequences include CelA of N. patriciarum (SEQ ID NO:23) (Denman et al., 1996), CBHIIs of Trichoderma reesei (SEQ ID NO:24) (Teeri et al. 1987. Gene 51:43–52), Fusarium oxysporum (SEQ ID NO:25) (Sheppard et al. 1994. Gene 150:163–167), Agaricus bisporus (SEQ ID NO:26) (Chow et al. 1994. Appl. Environ. Microbiol. 60:2779–2785), and Phanerochaete chrysosporium (Tempelaars et al. 1994. Appl. Environ. Microbiol. 60:4387–4393), C. fimi CenA (SEQ ID NO:27) (CelA_Celfi, Wong et al. 1986. Gene 44:315–324), T. fusca E2 (SEQ ID NO:28) (Cele2_Thefu, Lao et al. 1991. J. Bacteriol. 173:3397–3407), Streptomyces Ksm-9 (SEQ ID NO:29) (CelA_Strep, Damude et al. 1993. Gene 123:105–107) Dots are spaces introduced to optimize alignment.

FIG. 10 provides the nucleotide and deduced amino acid sequences for the celB cDNA. The RP regions are underlined. See also SEQ ID NO:11 and SEQ ID NO:12.

FIG. 11 provides the nucleotide and deduced amino acid sequences of an Orpinomyces PC-2 xylanase cDNA (xynA). The RP regions are underlined. See also SEQ ID NO:13 and SEQ ID NO:14).

FIG. 12 provides a comparison of the deduced amino acid sequences for Orpinomyces celB (O-CelB) (SEQ ID NO:2) and Neocallimastix celB (N-CelB) (SEQ ID NO:15). Amino acids with identical match and to different degree of similarities (: or.) are indicated. Positions of amino acids in the enzymes are labeled on the right. The comparison was generated using the Bestfit program of the Genetic Computer Group, Version 8 (University of Wisconsin Biotechnology Center, Madison, Wis.) on the VAX/VMS system of the BioScience Computing Resource, University of Georgia, Athens, Ga.

FIG. 14 shows the amino acid alignment of the RP regions of polysaccharide hydrolases of anaerobic fungi. Residues identical between all RPs are blocked.

DETAILED DESCRIPTION OF THE INVENTION

Abbreviations used in the present specification include the following: aa, amino acid(s); bp, base pair(s); CD, catalytic domain(s); cDNA, DNA complementary to RNA; GCG, Genetics Computer Group, Madison, Wis.; CMC, carboxymethyl cellulose; HMWC, high-molecular weight complex(es); IPTG, isopropyl-,-D-thiogalactoside; OSX, oat spelt xylan; ORF, open reading frame; RBB, remazol brilliant blue; RP, repeated peptide(s); pfu, plaque forming units.

Our studies have demonstrated that despite distinct morphological differences between monocentric and polycentric fungi, they both form HMWCs comprising similar catalytic enzymes. We describe two similar but distinct cellulases (CelA and CelC) of Orpinomyces and a third cellulase (CelB) as well. These two enzymes have the catalytic domains homologous to those of Neocallimastix CelA and other family B cellulases but contain the RP domains instead of CBDs at their N-termini. Characterization of the three enzymes cloned from Orpinomyces PC-2 indicated that Orpinomyces CelB is an endoglucanase whereas CelA and CelC have both endoglucanase and cellobiohydrolase activities.

Figure 1:
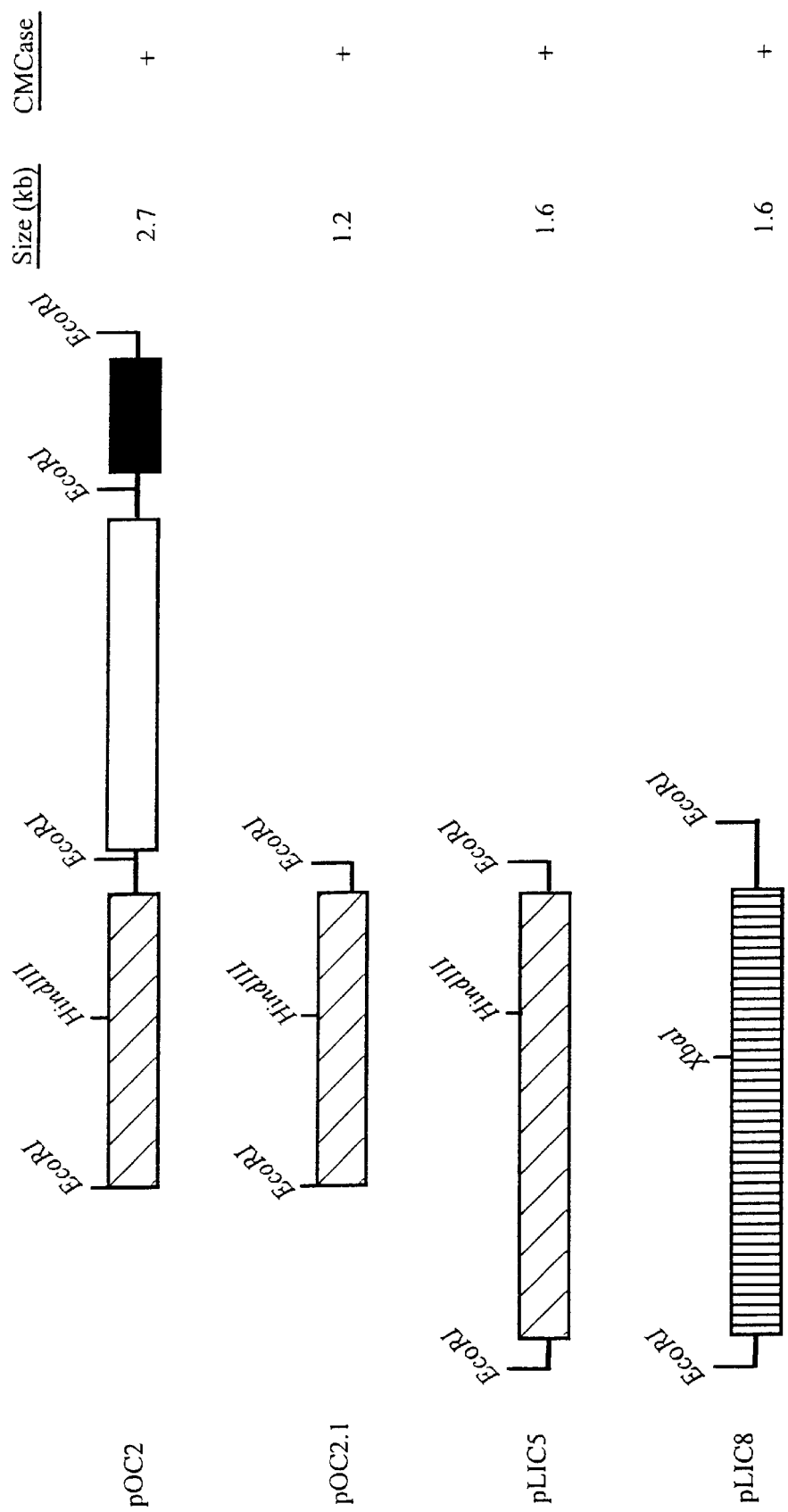
FIG. 1 provides restriction maps of some positive clones isolated using RBB-CMC or lichenan as indicator substrates. The position where the 5' ends of pOC2 and pOC2.1 start in pLIC5 is shown in FIG. 2. Bold boxes and horizontal lines represent open reading frames and untranslated regions, respectively.

A cDNA library constructed in λZAPII with mRNA extracted from Orpinomyces PC-2 (Chen et al. 1995. Proc. Natl. Acad. Sci. USA. 92:2587–2591) was screened for clones active on RBB-CMC (Sigma Chemical Co., St. Louis, Mo.). Two different clones with the insert size of 2.7 (pOC2) and 1.8 kb (pOC1) were obtained. Sequencing of both clones revealed that the inserted DNA in pOC2 possessed cDNAs of three unrelated genes, resulting from ligation of unrelated cDNA sequences at the EcoRI sites of the adapters. A 1.2 kb sequence at the 5' region consisted an incomplete open reading frame encoding a polypeptide homologous to fungal and bacterial cellulases (FIG. 2), followed by two sequences coding for a polypeptide homologous to a yeast amino peptidase and a H4 histone protein. The incomplete ORF encoding the cellulase in pOC2 was fused in frame to the lacZ gene. Thus, the cellulase was synthesized as a fusion protein. Subcloning of the 1.2 kb fragment into pBluescript with the same orientation yielded pOC2.1, which had the same level of activity on CMC as did pOC2 (FIG. 1). Clone pOC1 possessed a cDNA insert of 1825 bp containing a complete ORF (celB) which encoded a polypeptide (CelB) of 471 amino acids, as discussed hereinbelow.

The same library was screened for clones hydrolyzing lichenan, a glucan with alternating linkages of β-1,3 and β-1,4 bonds. Twenty positive clones were isolated when $2.5 \times 10^6$ pfu were plated. Restriction analysis revealed these clones represented cDNAs of 4 distinct genes. Sequencing of these clones revealed that pLIC5, among these clones, contained 1558 bp with a complete ORF (celA) encoding a polypeptide (CelA) of 459 amino acids (FIGS. 1, 2). See also SEQ ID NOS:1–2. The difference between pOC2.1 and pLIC5 was that pLIC5 contained a 5' non-coding region and a region encoding the N-terminal 115 amino acids that were missing in pOC2.1 (FIG. 2). The sequences of these two clones encoding the amino terminal 345 amino acids and 3' non-coding ends were identical (FIG. 2). These results suggest that the 115 amino acids at the carboxy region of CelA are not required for catalysis. Another lichenan hydrolyzing clone, pLIC8, had an insert of 1628 bp with a complete ORF (celC) coding for a polypeptide (CelC) of 449 amino acids. See also SEQ ID NOS:3–4. The assignment of translation start codons for celA and celC was based on: 1) Both ORFs had stop codons proceeding the ATG codons; 2) The amino terminal regions of these two polypeptides comprised a Lys as the second residue followed by hydrophobic amino acid residue rich peptides which are typical of secretion signal peptides for extracellular enzymes (Li and Ljungdahl. 1994. Appl. Environ. Microbiol. 60:3160–3166); and 3) Much higher A+T content regions preceded the putative ATG codons, as found for cDNAs encoding a cyclophilin (Chen et al., 1995, supra), an enolase (Durand et al. 1995. Microbiol. 141:1301–1308) and other hydrolases (Fanutti et al., 1995, supra) of anaerobic fungi. The upstream regions of mRNAs transcribed in E. coli for celA, celC and celB and xynA must possess nucleotide sequences similar to the E. coli ribosomal binding sites for translation initiation. The calculated masses for CelA and CelC precursors were 50,580 and 49,389 Da, respectively, which are slightly larger than the mass of CelA precursor (45,681 Da) of Neocallimastix (Denman et al., 1996) but smaller than those of CelB precursors of Neocallimastix (53,070 Da, Zhou et al., 1994, supra) and Orpinomyces (53,103 Da; see hereinbelow). It is obvious that for all the genes isolated from Orpinomyces so far, the wobble position was strongly biased to A or T, and G is rarely used (Table 1). Codons such as GGG, GCG, AGG, TCG, CGG, CGA, CAG, CTG, and CCG were never used. Translation stop codons containing G (TGA and TAG) were not used. High A+T content genes and extremely A+T rich non-coding regions of anaerobic fungi were reported (Zhou et al., 1994, supra; Durand et al., 1995, surpa; Fanutti et al., 1995; Denman et al., 1996) indicating that anaerobic fungi share similar nucleotide compositions.

The complete nucleotide sequence of the celB coding sequence was determined in both strands. The sequence data for celB is given in FIG. 10. See also SEQ ID NOS:11–12. The total length of the insert was 1,825 bp, including an ORF encoding a polypeptide of 471 amino acids, with a calculated molecular mass of 53,102 Da. The start codon was assigned because there were three stop codons proceeding the ORF, and the amino terminal peptide contained a hydrophobic region characteristic of secretion signal peptides of extracellular enzymes (Li and Ljungdahl, 1994, supra). The G+C content of the 5' and 3' non-coding regions was extremely low (13.8%). A long 3' non-coding end (339 bp) was observed, but no typical long poly(A) tail was found at the 3' end of the insert.

Nucleotide and deduced amino acid sequences of celA, celB and celC were compared to each other and to the homologous sequences in SWISS-PROT and GP data banks. The amino acid sequences between CelA and CelC were 67.6% identical with three deletions of one, three, and five amino acid residues found in the carboxyl region of CelC (FIG. 5). The identity on the nucleotide level between celA and celC was even higher (76.9%). CelA and CelC did not show significant levels of identity with CelB except that the regions (amino acids 20–100) of CelA and CelC were highly homologous to the C-terminal region of CelB. Further analysis revealed that these regions in CelA and CelC corresponded to the RP domain (FIGS. 2, 3, and 4) found in CelB and XynA, as well as in several polysaccharide hydrolases of monocentric anaerobic fungi Neocallimastix and Piromyces (Gilbert et al., 1992, supra; Zhou et al., 1994, supra; Fanutti et al., 1995). Thus, the sequence of CelA and CelC could be dissected into several regions. They comprised short N-terminal regions with basic residues at the second positions followed by hydrophobic residue rich peptides. These regions are present in extracellular proteins, and they function as trans-membrane signals. The RP domains were next to the signal peptides. The removal of the signal peptides during the secretion of the enzymes exposes the RP domains at the N-termini. The RP domains were separated from the catalytic domains by linker peptides (FIG. 2 and FIG. 3). The linker regions contained 25–30 amino acid residues. The linker peptide in CelA. consisted of predominantly Gln, Pro, and Thr while that in CelC, of predominantly Thr. The fact that pOC2.1 was devoid of the entire signal peptide and RP domain as well as part of the linker sequence but remained catalytically active demonstrates that these regions are not required for catalysis. The lengths of the RPs (33–40 amino acids) varied but some of the residues were highly conserved among the enzymes (FIG. 4).

In contrast to the RP domains of CelA and CelC that lacked homology to CelA of Neocallimastix, the catalytic domains of CelA and CelC were highly homologous to that of Neocallimastix CelA (Denman et al., 1996). The catalytic region of Neocallimastix celA shared 71.9% and 70.3% identity at the nucleotide level with those of Orpinomyces celA and celC, respectively, and these values were 65.0% and 60.5% at the amino acid level. Furthermore, besides highly homologous to the catalytic domain of Neocallimastix CelA, the catalytic domains of CelA and CelC displayed significant levels of homology with fungal cellobiohydrolases and bacterial endoglucanases (Table 2, FIG. 5), which belong to family B glycanases (Henrissat et al. 1989. Gene 81:83–95; Beguin, P. 1990. Ann. Rev. Microbiol. 44:219–248). Thus, CelA and CelC should be placed into this family. However, all other cellulases in the family contain CBDs separated from their catalytic domains.

The linker sequence of CelA comprised mainly Gln and Pro residues (FIG. 2). Thr and Ser residues were also present. In contrast, the CelC linker region contained predominantly Thr (FIG. 3). It has been documented that cellulase linker sequences contain high percentage of Ser and Thr residues which are modified by O-linked glycosylation. The linker regions of CelA and CelC may also be glycosylated in recombinant eukaryotic host cells or in Orpinomyces. The linker sequence of the Neocallimastix CelA is much longer and contains almost only Asn residues (Denman et al., 1996) despite the fact that its catalytic domain is so similar to those of CelA and CelC.

The deduced amino acid sequences of celB from Orpinomyces PC-2 were used to search for homologous sequences in the SWISS-PROT and GP data banks. A number of cellulases with significant sequence relatedness to CelB (Table 1) were found. To our surprise, CelB was highly homologous to the CelB (83.1%) of *N. patriciarum* (Zhou et al., 1994, supra). The Neocallimastix CelB had 473 amino acids with a molecular mass of 53,070 DA, and it displayed characteristics of endoglucanases. Based on sequence relatedness, it was assigned to glycosidase family A. The CelB had significant levels of homology to endoglucanases from anaerobic bacteria. However, a major difference between N. patriciarum and anaerobic bacterial cellulases, was that the former had a noncatalytic RP domain (two RPs of 40 each) attached to the catalytic domain through a region rich in Thr and Ser. Comparison between Orpinomyces CelB and Neocallimastix CelB (FIG. 12) revealed that these two enzymes shared related primary structures. Less homology was observed in the putative secretion signal peptide regions and the linker regions between the CD and the first RP of the noncatalytic domains. Two apparent deletion and/or insertion mutations between these two enzymes were found in the linker region.

Figure 13:
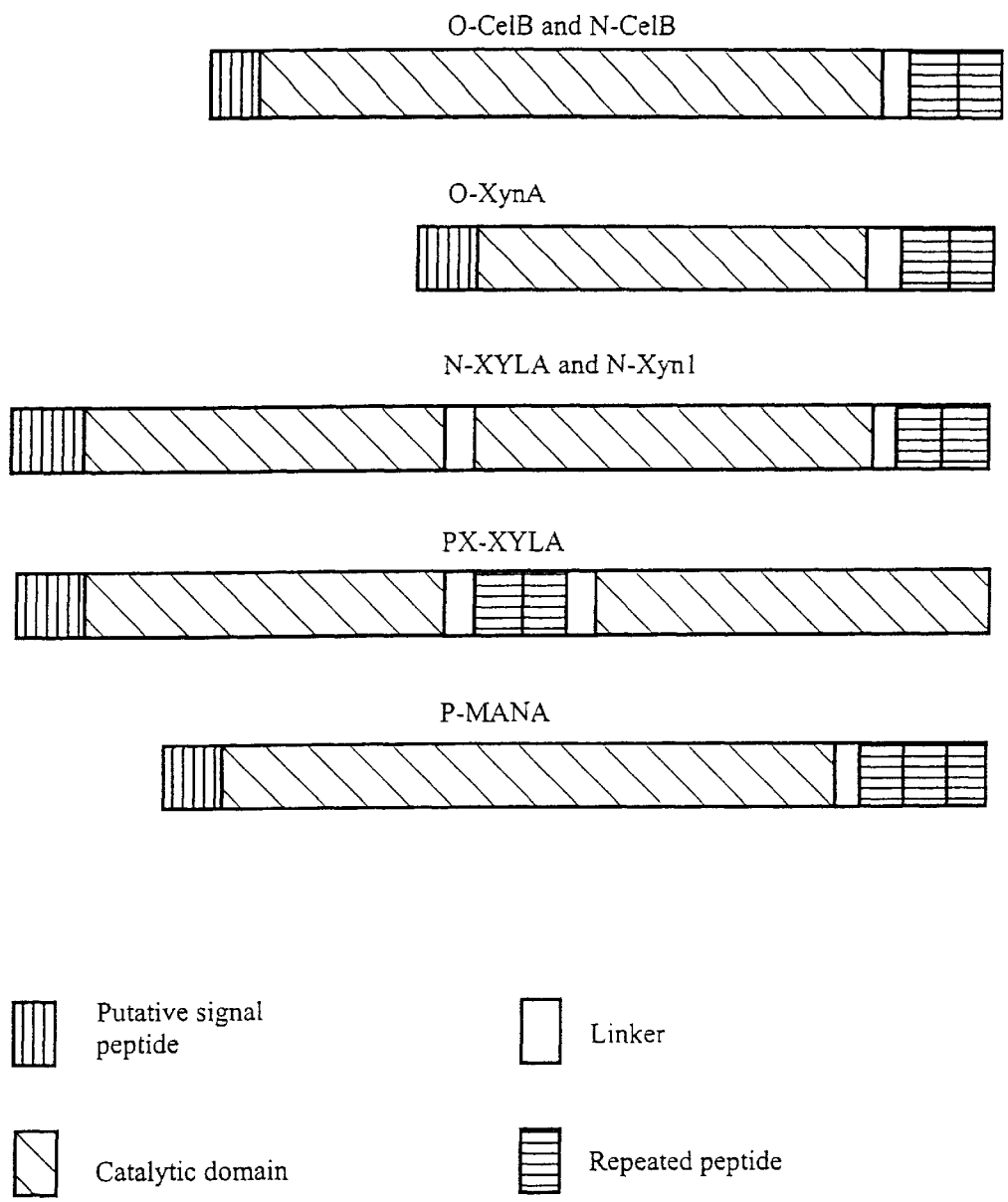
FIG. 13 illustrates the functional domains of anaerobic fungal polysaccharide hydrolases possessing RP domains. The sizes of the boxes were roughly scaled to the sizes of domains. Enzymes include CelB (O-CelB) and XynA (O-XynA) of Orpinomyces, CelB (N-CelB, Zhou et al., 1994, supra) and XylA (N-XylA, Gilbert et al., 1992, supra) of Neocallimastix, and XylA (P-XylA) and ManA (P-ManA) of Piromyces (Fanutti et al., 1995).

The domain organization of the RP containing polysaccharide hydrolases cloned from anaerobic fungi is illustrated in FIG. 13. Regardless of monocentric or polycentric fungal origin, the two RP sequences (36–40 amino acids each) are significantly homologous to each other and between different enzymes (FIG. 14). However, the number of the RPs and the location of these domains seem less critical as long as a linker sequence (15–30 amino acids) is placed between them and the CDs. Piromyces XylA had the RP domain between the two CDs while its ManA had a three RP domain. Neocallimastix and Orpinomyces cellulases and xylanases, however, have two RP domains at their C-termini. The RP domain of Piromyces XylA produced by *E. coli* bound to a 97 kDa protein of Piromyces and a 116 kDa protein of Neocallimastix, suggesting that these proteins function as scaffolding polypeptides in the formation of cellulase/ hemicellulase HMWCs (Fanutti et al., 1995, supra). It remains to be determined whether both RPs are required for the binding or whether just one of these RPs can effect the binding. The first reiterated peptide of CelS alone binds, in the presence of calcium ion, to CipA, the scaffolding protein in the *C. thermocellum* cellulosome (Choi and Ljungdahl, 1996). However, the two RP sequences of the fungal enzymes are more conserved than are the two reiterated sequences of *C. thermocellum* enzymes.

Figure 15:
FIG. 15 is a reproduction of a Western blot of extracellular proteins of anaerobic fungi grown on Avicel as Carbon source. Concentrated proteins of culture supernatants of Orpinomyces (lane 1 and 3) and Neocallimastix (lanes 2 and 4) were separated by SDS-10% PAGE and analyzed by Western blot using anti-sera against OPX1 (lanes 1 and 2) and OPX2 (lane 3 and 4).

To determine the number of polypeptides possessing the RPs from anaerobic fungi, antisera against synthetic peptides corresponding to the Orpinomyces XynA (FIG. 11, SEQ ID NO:13 and SEQ ID NO:14) were raised, and Western blots were carried out for the extracellular proteins of Orpinomyces and Neocallimastix grown on Avicel (FIG. 15). Antibody against OPXI, a region of the CD, gave one band of 36 kDa with Orpinomyces proteins (lane 1). The size was in agreement with that of XynA (39.5 kDa) after cleavage of signal peptide. One strong band (about 100 kDa) and several faint bands were detected on Neocallimastix proteins using anti-OPXI (lane 2). Some of the faint bands might be XylA (68 kDa for the precursor) and its degradation products since the OPXI region was relatively highly conserved between the Orpinomyces and Neocallimastix enzymes. In contrast, a number of bands of extracellular proteins of Orpinomyces (lane 3) and Neocallimastix (lane 4) reacted with the antibody against OPX2, the first RP region of the Orpinomyces XynA. These reactive bands ranged from 30 to 150 kDa (Orpinomyces) and 34 to 100 kDa (Neocallimastix). No bands were detected when preimmune sera were used for analyzing the fungal proteins. The heavy 35 kDa band (lane 3) matched the size of the band on lane 1, indicating that the band was the Orpinomyces XynA protein. Other positive bands of both Orpinomyces and Neocallimastix proteins were less intense and without wishing to be bound by theory, these are believed to reflect proteins with partial sequence identities. Western immunoblot analysis indicated that multiple polypeptides produced by Orpinomyces and Neocallimastix share regions with antigenic relatedness to OPX2. These regions are believed to be docking domains which mediate interactions between catalytic and noncatalytic structural polypeptides in HMWC. Catalytic polypeptides in the HMWC (cellulosome) of *C. thermocellum* and *C. cellulovorans* contain reiterated peptide domains that mediate interaction between the catalytic polypeptides and a scaffolding protein. The presence of the RP domains in multiple polypeptides shows that cellulase/hemicellulase complexes of anaerobic fungi and bacteria share similar features although differences in size, stability, number of subunits and types of enzyme activities were observed (Wood et al., 1992).

Figure 16:
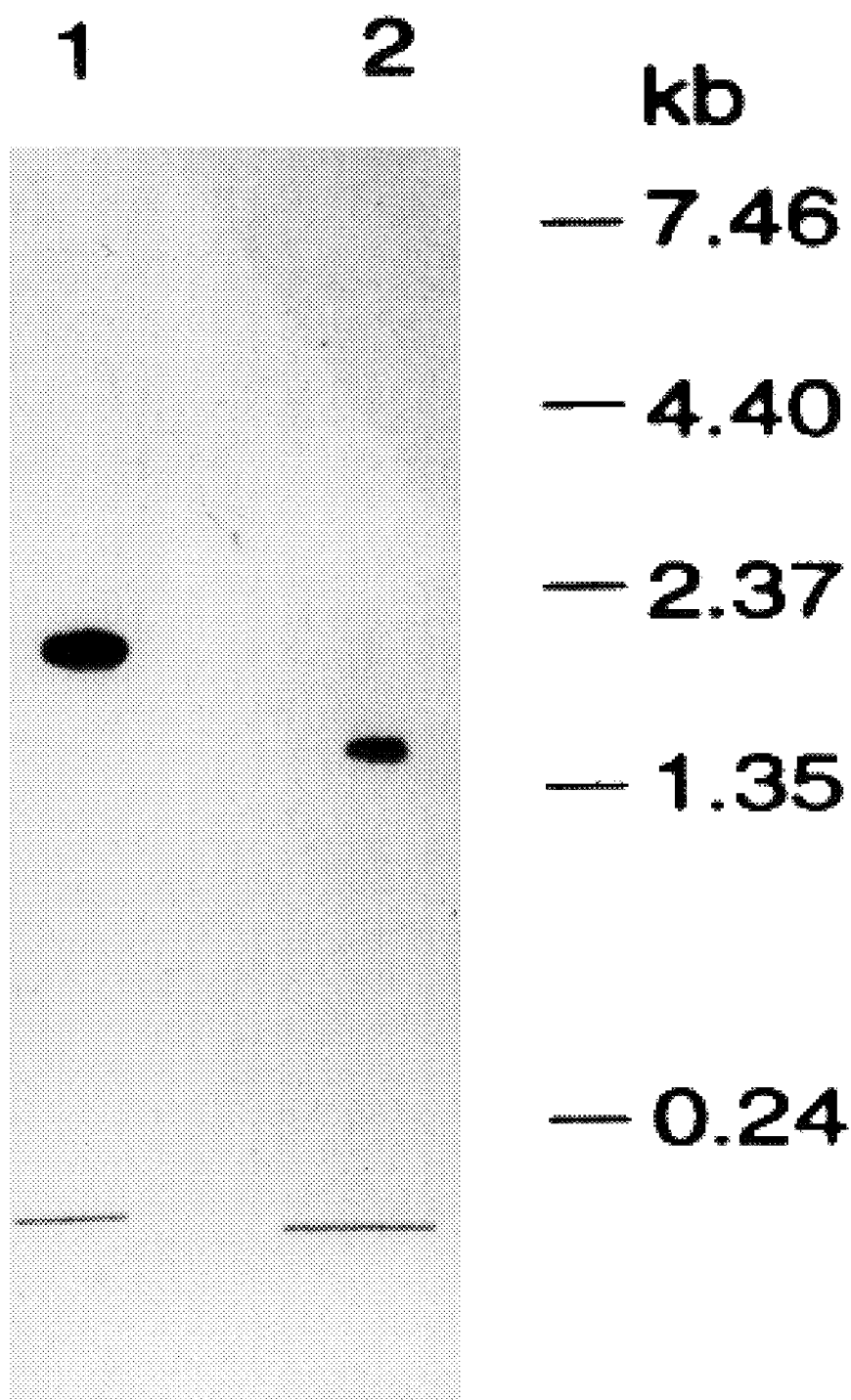
FIG. 16 represents Northern blots for Orpinomyces celB and xynA. In lane 1, total RNA from Orpinomyces PC-2 was size separated by agarose gel electrophoresis, transferred to a nylon membrane and hybridized with a labeled pOC1 (celB) probe. Lane 2 is RNA hybridized with labeled pOX8 (xynA) probe. The positions of molecular weight markers are shown at the right.

Northern blots revealed single transcripts of 1.9 kb for celB and 1.5 kb for xynA (FIG. 16) in Orpinomyces under the conditions where the polysaccharide hydrolase genes were induced. The sizes of these transcripts were slightly larger than the corresponding cDNA inserts. These results indicated that no additional highly homologous hydrolases to celB or xynA were produced under these conditions. The size of the celB transcript was the same as for the celB transcript of *N. patriciarum* (Xue et al. 1992. Cloning and expression of multiple cellulase cDNAs from the anaerobic rumen fungus *Neocallimastix patriciarum* in *Escherichia coli*. J. Gen. Microbiol. 138:1413–1420).

Figure 17:
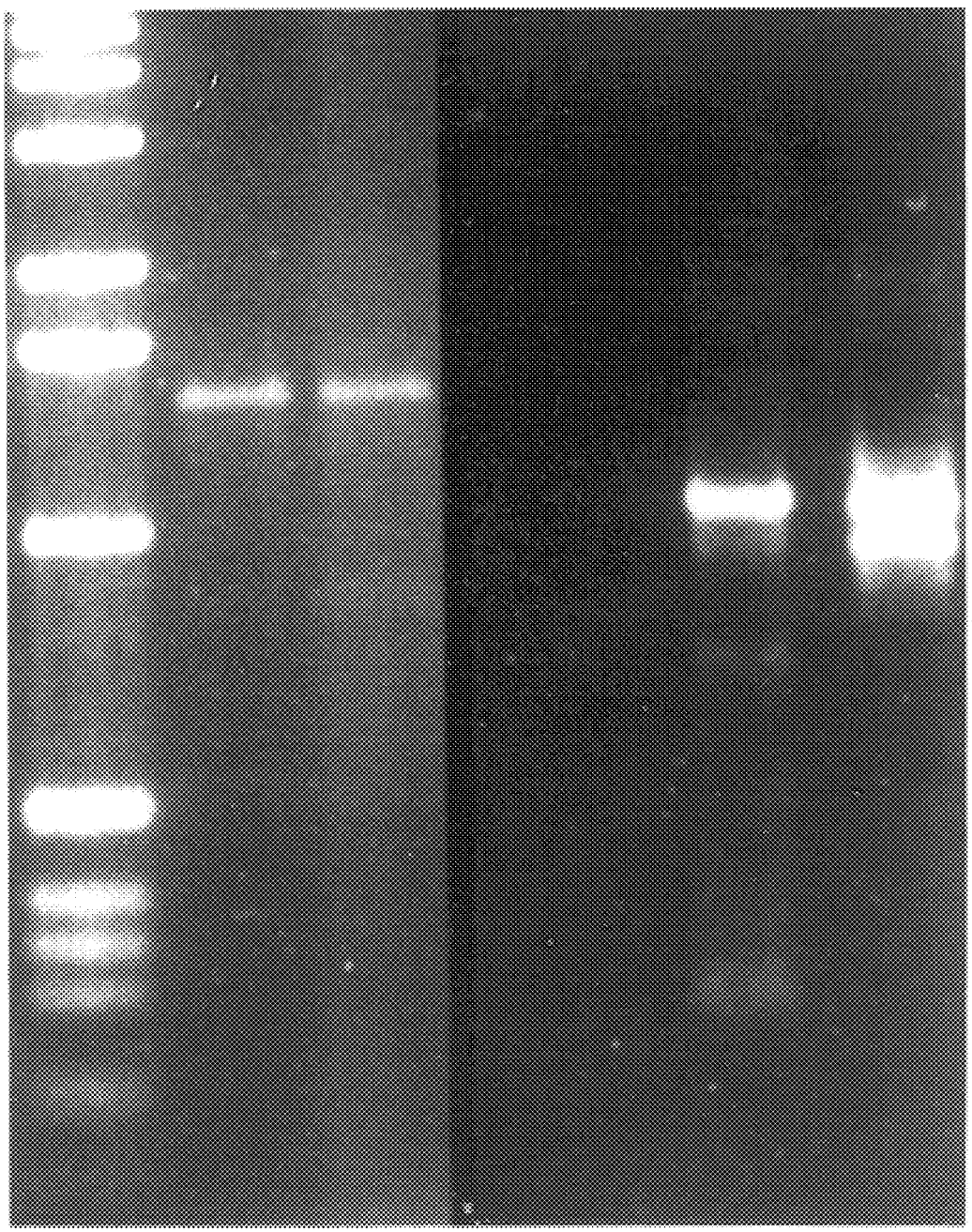
FIG. 17 shows the results of PCR amplification of genomic DNA corresponding to Orpinomyces celB and xynA. Lane 1 and 2 were loaded with samples amplified using primers to celB and by using the genomic DNA and the cDNA library, respectively, as templates. Lane 3, 4. and 5 were loaded with samples amplified by using the primers specific to xynA and by using no DNA, the genomic DNA, and the cDNA library, respectively as templates. Lane M was loaded with DNA size markers (Gibco BRL Life Technologies, Gaithersburg, Md.).

Coding regions of Orpinomyces cDNA and genomic DNA of celB and xynA were amplified by PCR (FIG. 17) and sequenced. The DNA fragment sizes and nucleotide sequences from both cDNAs and genomic DNAs for celB and xynA were the same, indicating there were no introns in the coding regions of these genes. A smaller band (1.0 kb) amplified from the cDNA library using the xynA specific primers (lane 5, FIG. 17) was found to be a λ DNA region by sequence analysis. No introns were found in the *N. patriciarum* celB gene (Zhou et al., 1994, supra). By contrast, introns have been demonstrated in a cyclophilin gene of Orpinomyces (Li et al., 1995) and an enolase gene of *N. frontalis* (Durand et al., 1995, supra). Polysaccharide hydrolase genes of the aerobic fungi are commonly interrupted by introns (Knowles et al., 1987 Cellulase families and their genes. Trends Biotechnol. 5:255–261; Li and Ljungdahl, 1994, supra).

The cellulases encoded by the three distinct genes, celA, celB, and celC of the polycentric anaerobic fungus Orpinomyces PC-2 share structural similarities between each other and with enzymes from other anaerobic fungi. The most striking similarity was that the three cellulases all have the RP domain. This domain is also present in a xylanase of the same fungus (described in U.S. Ser. No. 08/315,695, incorporated by reference herein) and several hydrolases of monocentric anaerobic fungi (Gilbert et al., 1992, supra; Zhou et al., 1994, supra; Fanutti et al., 1995). Western blot analysis using polyclonal antibody against the RP domain of an Orpinomyces xylanase demonstrated that numerous extracellular proteins of Orpinomyces and Neocallimastix contain this domain. Our work, together with others (Gilbert et al., 1992, supra; Fanutti et al., 1995) have shown that the RP domain is not involved in catalysis or cellulose binding. Recently, Fanutti et al. (1995) showed that the RP domain of a Piromyces xylanase binds to other polypeptides of the Neocallimastix and Piromyces high molecular weight complexes. All these observations support the idea that plant cell wall degrading enzymes of anaerobic fungi form multi-enzyme complexes similar to the cellulosomes of anaerobic bacteria Clostridium species (Beguin, 1990, supra; Felix and Ljungdahl, 1993, supra; Doi et al., 1994, supra). The cellulosome of C. thermocellum comprises 14 to 26 polypeptides, divided into a number of catalytically active components and a non-catalytic cellulosome integrating polypeptide A (CipA). The interaction between the catalytic components and CipA is mediated by the non-catalytic reiterated peptide domains of the catalytic components and nine internal repeated elements of CipA (Felix and Ljungdahl, 1993, Kruus et al. 1995. The anchorage function of CipA (CelL), a scaffolding protein of the Clostridium thermocellum cellulosome. Proc. Natl. Acad. Sci. USA 92:9254–9258, Choi and Ljungdahl, 1996). The fact that multiple hydrolases of anaerobic fungi contain the RP domain that binds to other polypeptides rather than cellulose suggests that the RP domain functions like the conserved duplication regions (CDR) of the catalytically active subunits of the bacterial cellulosomes. All catalytic polypeptides of the cellulosomes have CDRs at the C-terminal or internal regions. The hydrolases cloned and sequenced so far from three anaerobic fungal species contain the RP domain either at C-termini or between two catalytic domains. The presence of the RP domain at the N-termini of the mature CelA and CelC indicates that the position of this domain in fungal enzymes is not critical. Assuming that the RP domains of various hydrolases bind to a scaffolding protein with the same orientation, varying the RP domain locations provides more conformational variation for the catalytic subunits in the complexes.

Orpinomyces CelA and CelC are highly identical to each other and related in sequence to CelA of the monocentric fungus *Neocallimastix patriciarum* (Denman et al., 1996). However, the most striking distinction between the Orpinomyces and Neocallimastix enzymes is that the noncatalytic domains in Orpinomyces CelA and CelC were replaced by a cellulose binding domain in CelA of Neocallimastix. Thus, this indicates: 1). Orpinomyces CelA and CelC are complex-bound enzymes while Neocallimastix CelA is a free enzyme; 2). The non-catalytic domains and catalytic domains of hydrolases of anaerobic fungi probably evolved from different origins; and 3). Genes encoding CelA and CelC of Orpinomyces and CelA of Neocallimastix may have resulted from horizontal gene transfer between the fungi with subsequent duplication in Orpinomyces. Cellulases and xylanases with homologous tandem catalytic domains in single polypeptides have been found from Neocallimastix (Gilbert et al., 1992, supra) and Piromyces (Fanutti et al., 1995). The presence of CelA and CelC encoded by separated genes with highly similar catalytic domains represents another type of gene duplication.

Cell free extracts of *E. coli* expressing Orpinomyces cellulases were prepared and activities of these samples on various substrates were determined (Table 3). CelA, CelB and CelC hydrolyzed CMC, acid swollen cellulose (ASC), lichenan, barley β-glucan at similar rates. Low but detectable hydrolysis of Avicel by CelA and CelC was observed while CelB hardly hydrolyzed this substrate. CelC also had detectable levels of activity on other polymeric substrates containing β-1,4-, β-1,3, or β-1,6 glucoside bonds.

CelA and CelA with the RP domain truncated (ΔCelA, pOC2.1) had almost identical substrate specificities (Table 3), suggesting that the RP domain is involved in neither catalysis nor substrate binding.

The four different cellulase preparations of *E. coli* cell lysates were tested for the capability to absorb microcrystalline cellulose (Avicel) (Table 4). More than 90% of activity of recombinant Orpinomyces CelA, ΔCelA, and CelB were recovered after the Avicel treatment, indicating that they do not possess strong cellulose binding affinity. Less than 50% activity of CelC was recovered after Avicel absorption treatment and addition of BSA up to 4 times of the *E. coli* proteins failed to increase the recovery.

Figure 6:
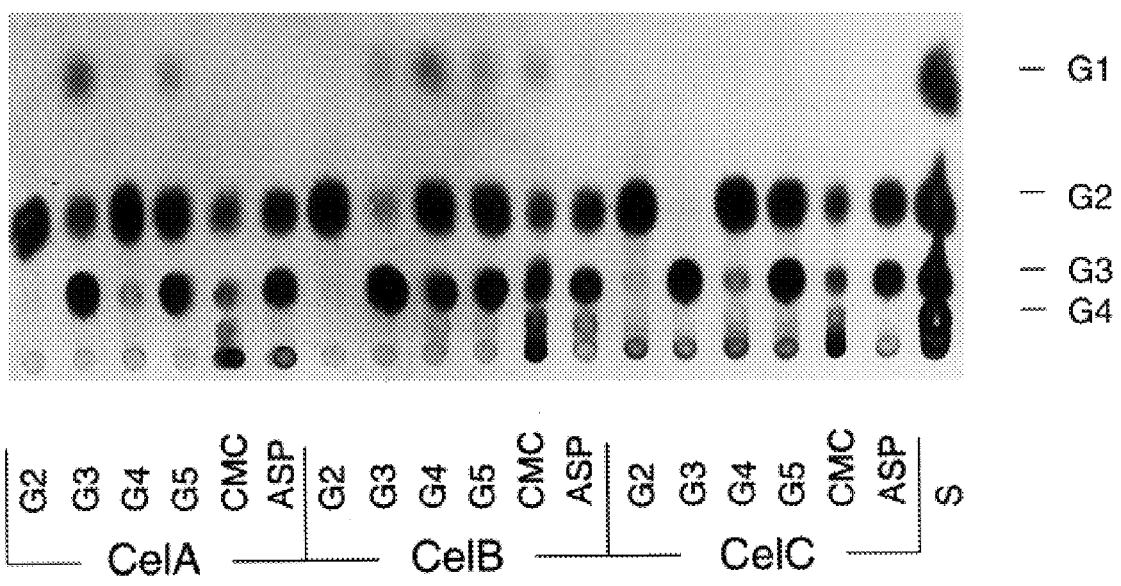
FIG. 6 shows the results of TLC analysis of products of CMC, ASC and cellodextrins hydrolyzed by CelA, CelB, and CelC. The procedures for enzyme and substrate preparations, hydrolysis, TLC, and visualization are described in the Examples. Glucose (G1) and cellodextrins including cellobiose (G2), cellotriose (G3), cellotetraose (G4), and cellopentaose (G5) were used as standards (S) in equal molarity or separately as substrates.

CMC, ASC, and cellodextrins were used as substrates for the three Orpinomyces cellulases, and the hydrolysis products were separated and detected with TLC (FIG. 6). The hydrolysis products of CMC and ASC by the three enzymes contained cellobiose and cellotriose. The hydrolysis of CMC and ASC by CelB also generated detectable amount of glucose and cellotetraose. Oligosaccharides larger than cellotriose were also detected during the hydrolysis of CMC by CelA and CelC but were not detected with ASC as substrate. No glucose was liberated from these two polymeric substrates by CelA or CelC.

None of the three enzymes hydrolyzed cellobiose. Different product profiles between the three enzymes were obtained when cellotriose, cellotetraose, and cellopentaose were the substrates. CelA and CelB hydrolyzed part of cellotriose to cellobiose and glucose, but CelC was not able to cleave this substrate. Cellotetraose was cleaved predominantly into two molecules of cellobiose by CelA or CelC, with trace amounts of glucose and cellotriose in the case of CelA but no production of glucose in the case of CelC. The trace amount of cellotriose and possibly some higher molecular oligosaccharides during the hydrolysis of cellotetraose by CelC suggests that CelC may have transglycosylation activity. The proportion of glucose to cellotriose from the hydrolysis of cellotetraose by CelB were much higher than that by CelA, indicating that CelA and CelB have different rates of hydrolysis on the three glycosidic bonds in cellotetraose. CelA and CelB hydrolyzed cellopentaose to cellotriose, cellobiose and glucose, while CelC cleaved this substrate into one molecule each of cellotriose and cellobiose with no production of glucose resulting from further hydrolysis of cellotriose.

Figure 7:
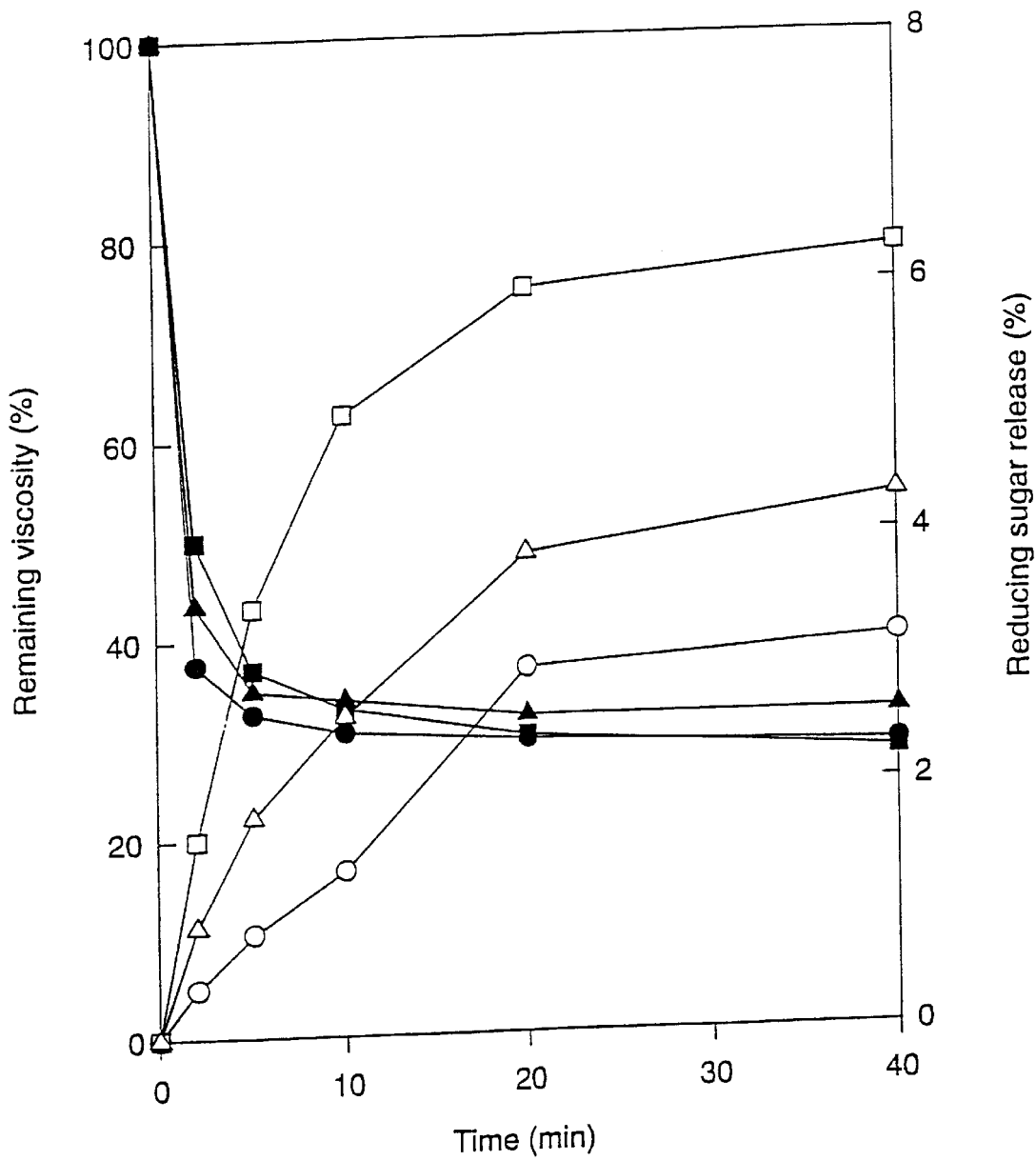
FIG. 7 illustrates viscosity reduction and reducing sugar production during the hydrolysis of high viscosity CMC by CelA, CelB, and CelC. Remaining viscosity is the percent of viscosity over the viscosity obtained with heat-inactivated enzymes whereas the reducing sugar production is expressed as the percent of reducing ends generated over the total theoretical ends.

The viscosity change and accumulation of reducing sugars during the hydrolysis of CMC by the three Orpinomyces enzymes were determined (FIG. 7). All three cellulases reduced the viscosity of CMC rapidly during the first 5 min of hydrolysis. The reduction during the first 2 min was particularly fast with CelC, followed by CelA and CelB. Between 5 to 40 min the viscosity change was much slower in comparison to the initial hydrolysis. The viscosity values did not get lower than 30%. The levels of reducing sugars increased the fastest during the incubation of CMC with CelB, intermediate with CelA, and the slowest with CelC (FIG. 7). The generation of reducing ends by the three enzymes for the first 20 min was much faster than the next 20 min. After 40 min, only small percentages of reducing ends (4.4% by CelA, 6.4% by CelB, and 2.6% by CelC) in the substrate were generated. The percentages of reducing ends were very small after 2 min of hydrolysis but most of viscosity reduction was achieved by all the three enzymes.

Figure 8:
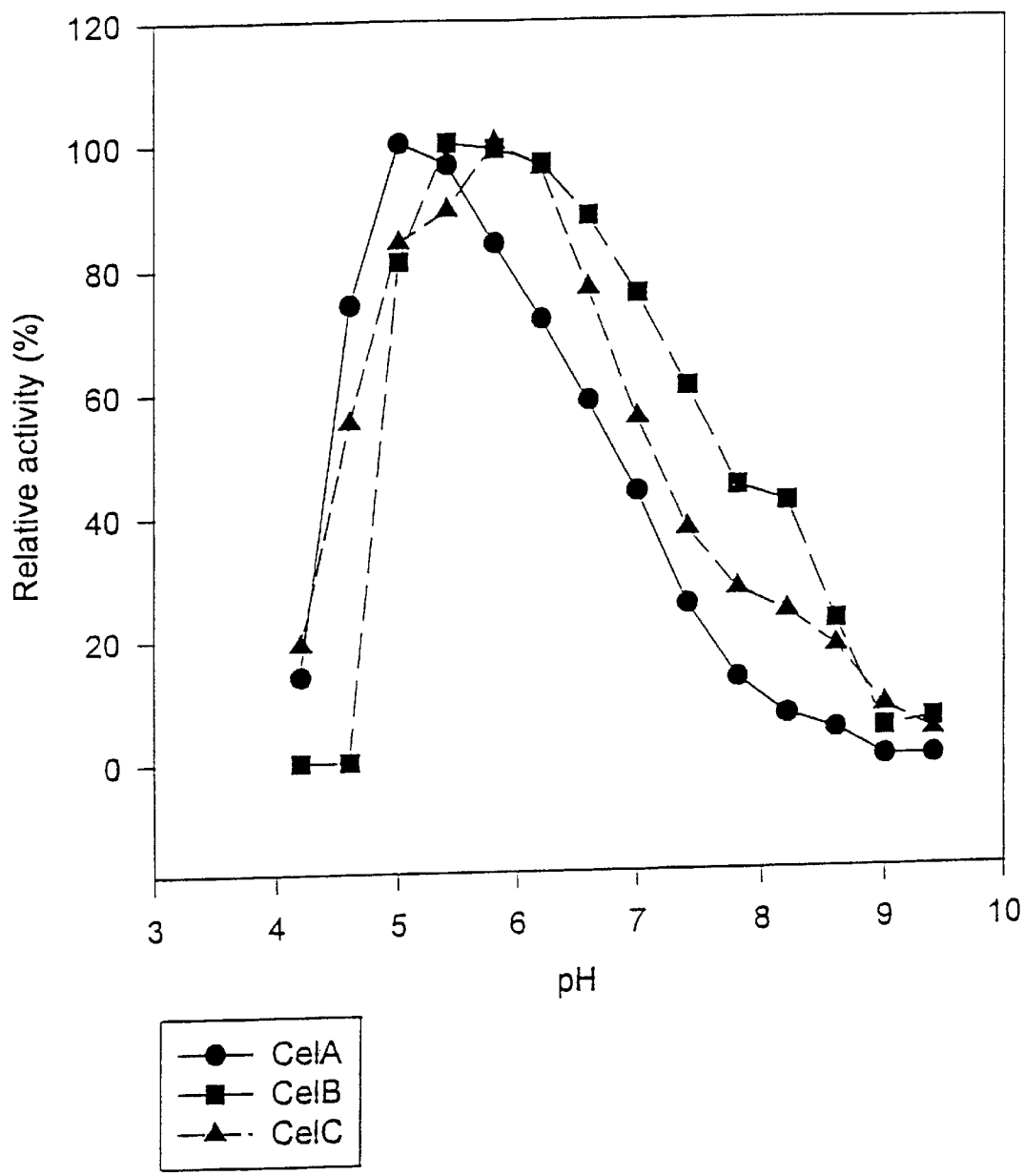
FIG. 8 illustrates the effect of pH on the activities during the hydrolysis of CMC by CelA (●), CelB (■), and CelC (▲).

Activities of the three Orpinomyces enzymes towards CMC were determined over broad ranges of pH and temperature. CelA, CelB, and CelC had the highest activity at pH 4.8, 5.2–6.2, and 5.6–6.2, respectively (FIG. 8). The three enzymes displayed more than 50% of the highest activity in pH ranges of 4.3–6.8 for CelA, 4.8–7.6 for CelB, and 4.6–7.0 for CelC (FIG. 8). All three enzymes after preincubation at pH from 3.5–9.6 for 1 hr retained 80% or more of their maximal activities. Neocallimastix CelA has the highest activity at pH 5.0, with more than 40% of maximal activity between 4.5–6.5 (Denman et al., 1996), which is similar to the profile of CelA but in a more acidic range than those of CelB or CelC (FIG. 8).

Figure 9:
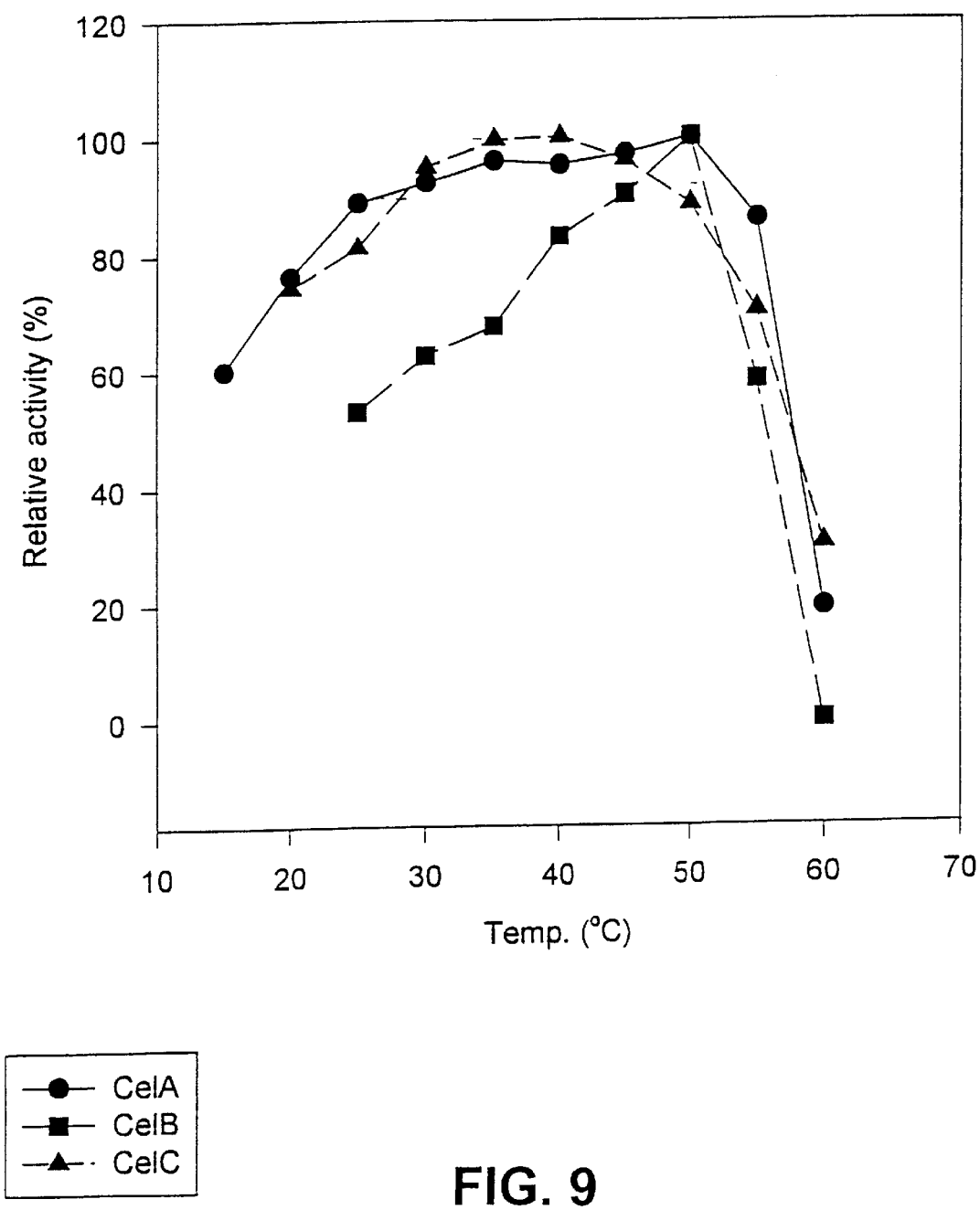
FIG. 9 illustrates the effect of temperature on the activities during the hydrolysis of CMC by CelA (●), CelB (■), and CelC (▲).

Orpinomyces CelA, CelB, and CelC all displayed high activities over broad ranges of temperature with the highest activity at 50° C. for CelA and CelB and 40° C. for CelC (FIG. 9). The three enzymes had more than 50% of maximal activity at 55° C., but the activity rapidly diminished at 60° C. (FIG. 9). CelA and CelC retained more activity in the lower temperature range (20–40° C.) than CelB did (FIG. 9). All three enzymes retained more than 90% of the activity after preincubation at 45° C. for 24 h in the absence of substrate. CelA, CelB, and CelC retained 92%, 20%, and 83%, respectively, of the activity after 5 h of preincubation at 50° C. Activity of each of the three enzymes was irreversibly inactivated at 60° C. or higher temperatures.

The pH and temperature profiles indicate that all the three enzymes of Orpinomyces are active under the rumen physiological conditions (pH, 6–7 and temperature, 38–42° C.) (Yokoyama and Johnson. 1988. Microbiology of the rumen and intestine. In: D.C. Church (ed.) The Ruminant Animal: Digestive Physiology and Nutrition. p. 125–144. Reston Book, Prentice Hall, Englewood Cliffs, N.J.).

Despite highly similar catalytic domains, the ratios of activities on Avicel to activities CMC of Orpinomyces CelA (0.06, Table 3) and CelC (0.10, Table 3) were lower than that of Neocallimastix CelA (0.54, Denman et al. 1996). The low levels of activity on Avicel are correlated with the low levels of affinity for Avicel of the Orpinomyces enzymes in comparison to the Neocallimastix enzyme. These differences may be caused by the lack of CBDs in the Orpinomyces enzymes. Removal of the CBDs in Neocallimastix CelA (Denman et al., 1996) or in *T. reesei* cellobiohydrolases (Tomme et al. 1988. Studies of the cellulolytic system of *Trichoderma reesei* QM9414. Analysis of domain function in two cellobiohydrolases by limited proteolysis. Eur. J. Biochem. 170:575–581) retained or even boosted the activities on soluble substrates but drastically reduced the hydrolysis of crystalline cellulose. These results indicate that Orpinomyces CelA and CelC are anchored to cellulose by a way different from the CBD-containing enzymes. Anchorage can be mediated by polypeptides similar to the CipA of the *C. thermocellum* cellulosome. Clostridial cellulases, when associated with noncatalytic CBD containing polypeptides, significantly increase the hydrolysis of crystalline cellulose (Wu et al. 1988. Two components of an extracellular protein aggregate of *Clostridium thermocellum* together degrade crystalline cellulose. Biochemistry 27:1703–1709; Shoseyov and Doi. 1990. Essential 170-kDa subunit for degradation of crystalline cellulose by *Clostridium cellulovorans* cellulase. Pro. Natl. Acad. Sci. USA 87:2192–2195).

Cellulases, particularly cellulases of aerobic fungi, have been classified as endoglucanases or cellobiohydrolases (exoglucanases) based on the mode of activity on various substrates. Endoglucanases hydrolyze CMC randomly and internally, thus causing the reduction of viscosity of the substrate. The hydrolysis end products are mainly glucose, cellobiose, and cellotriose. Endoglucanases lack activity on Avicel. In contrast, cellobiohydrolases remove cellobiose units from the non-reducing ends of a cellulose chain or cellodextrins. Therefore, the main hydrolysis end product is cellobiose and the reduction of CMC viscosity is minimal. The Orpinomyces CelB hydrolyzed CMC and caused rapid viscosity reduction of CMC. These data, together with the product profiles of CMC and cellodextrin hydrolysis, indicate that CelB is a typical endoglucanase. This enzyme has 84% sequence identity with Neocallimastix CelB which is a member of the glycosyl hydrolase family A (Henrissat et al., 1989, supra; Zhou et al., 1994, supra). The classification of CelA and CelC with endoglucanases or cellobiohydrolases, however, seems impossible. CelA and CelC have activities on CMC, ASC, and Avicel. The main products of CMC and ASC hydrolysis were cellobiose and cellotriose. No glucose was detected. Cellotriose was slowly hydrolyzed by CelA but not hydrolyzed by CelC. The lack of CelC activity on cellotriose indicates that CelC is more like a cellobiohydrolase than CelA, although they share very similar primary structures.

The three dimensional structures of the catalytic domains of two family B enzymes, CBHII, a cellobiohydrolase from *T. reesei* (Rouvinen et al. 1990. Three-dimensional structure of cellobiohydrolase II from *Trichoderma reesei*. Science 249:380–386) and E2, an endoglucanase from *T. fusca* (Spezio et al. 1993. Crystal structure of the catalytic domain of a thermophilic endocellulase. Biochemistry 32:9906–9916) have been determined. The overall topologies of these two enzymes overlap to a high degree despite sharing only 26% sequence identity and the classification of one as a cellobiohydrase and the other as an endoglucanase.

Four aspartic acid residues (Asp$^{199}$, Asp$^{245}$, Asp$^{287}$, and Asp$^{425}$ of *T. reesei* CBHII) are conserved between the two types of the enzymes in this family (FIG. 5) and found to form the active site for cellulose chain cleavage (Rouvinen et al., 1990). The distinction between the catalytic modes of these two types, of enzymes is that the active site tunnel of CBHII is enclosed by two surface loops that block the access by long cellulose chains (Rouvinen et al., 1990). One of the loops in E2 is absent while the other is present but pulled away due to a deletion adjacent to this loop (Spezio et al., 1993, supra). As a consequence of these changes, the tunnel in E2 is easily accessed by cellulose chains. The loop absent in E2 corresponds Ser$^{418}$ to Gly$^{436}$ of CelA of Orpinomyces (FIG. 4). Deletions of two amino acids for Orpinomyces and Neocallimastix CelAs and five amino acids for Orpinomyces CelC suggest that this loop in the cellulases of anaerobic fungi might only partially enclose the tunnel of the active side. The other loop which covers the other end of the tunnel of CBHII but is pulled away in E2 is related to the region corresponding to Pro$^{204}$ to Ser$^{217}$ of CelA from Orpinomyces (FIG. 4). The three cellulases from anaerobic fungi all have apparent deletions of four amino acids, which may form a loop distinct from those of either the aerobic fungal cellobiohydrolases or the bacterial endoglucanases. Nevertheless, the regions of the three cellulases of anaerobic fungi involved in the loop formation are distinct from those of cellobiohydrolases and endoglucanases and may allow access to both long cellulose chains and their ends. As a result, these changes may allow the three enzymes of anaerobic fungi to display both endo- and exo-type activities. It should be also pointed out that deletion and insertions of regions other than the loop regions of the three cellulases in comparison with the cellobiohydrolases and endoglucanases also contributes to the structural changes with the result that these enzymes display both activities.

Percentage of sequence identity for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using either BlastN or BlastX with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that polynucleotide sequences are substantially identical is if two molecules selectively hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at 65° C. with 0.2× SSC.

Monoclonal or polyclonal antibodies, preferably monoclonal, specifically reacting with a particular cellulase enzyme of the present invention may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, New York; Maniatis et al. (1982) *Molecular Cloning*, Cold Spring Harbor Laboratory, Plainview, New York; Wu (ed.) (1993) *Meth. Enzymol* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, New York; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

Each reference cited in the present application is incorporated by reference herein.

The following examples are provided for illustrative purposes, and is not intended to limit the scope of the invention as claimed herein. Any variations in the exemplified articles which occur to the skilled artisan are intended to fall within the scope of the present invention.

EXAMPLES

Example 1
Cultures and vectors.

The polycentric anaerobic fungus Orpinomyces sp. strain PC-2 was originally isolated from bovine rumen (Borneman et al., 1989, supra) and cultivated as described by Barichievich and Calza. 1990. Appl. Environ. Microbiol. 56:43–48). *Escherichia coli* XL-Blue, λZAPII, and pBluescript SK(-) were products of Stratagene Cloning Systems (La Jolla, Calif.).

Example 2
Cloning and sequencing of celA and celC cDNAs.

The extraction of total RNA from Orpinomyces mycelia grown in liquid media containing; 0.2% (wt/vol) Avicel PH-101 (microcrystalline cellulose; Fluka Chemie AG, Buchs, Switzerland), purification of mRNA, and construction of a cDNA library in λZAPII were described previously (Chen et al., 1995, supra). To isolate cellulase clones, λ plaques were developed after infecting *E. coli* cells in standard NZY medium (Stratagene) plus 5 mM isopropyl-β-D-thiogalactopyranoside (IPTG) and 0.2% ramozol brilliant blue (RBB)-carboxymethylcellulose (CMC) or lichenan. Positive clones were recognized as clear haloes on blue background in the case of RBB-CMC and as light yellow zones on a red background after staining with 1 mg/ml Congo red and destaining with 1 M NaCl (Beguin, 1984, supra) in the case of lichenan. Pure λ clones were obtained after a secondary screening with a lower density of plaques and converted into pBluescripts by in vivo excision (Stratagene, La Jolla, Calif.). *E coli* XL-Blue cells harboring the pBluescript-derived plasmids were grown overnight at 37° C. in Luria-Bertani (LB) medium containing 100 µg/ml ampicillin. Plasmids were purified using the spin column miniprep kit (Qiagen, Chatsworth, Calif.) or the Maxiprep kit (Promega, Madison, Wis.). Plasmids from different primary clones were subjected to restriction endonuclease digestion with various enzymes and DNA fragments were separated on agarose gels (Sambrook et al., 1989, supra). DNA samples were purified by rinsing in Centricon tubes (Amicon, Beverly, Mass.) before they were subjected to sequencing on an automatic DNA sequencer (Applied Biosystems, Foster City, Calif.). Both strands of the cDNA inserts were sequenced by walking down from the ends of the inserts using the plasmid sequence specific primers. Sequence data analyses, data bank searches, and multiple sequence alignments were performed by using the Genetic Computing Group package (University of Wisconsin Biotechnology Center, Madison, Wis.) on the VAX/VMS system of the BioScience Computing Resource of the University of Georgia (Athens, Ga.).

The celA and celC sequences of Orpinomyces PC-2 have been deposited in GenBank with accession numbers of U63837 and U63838, respectively.

Example 3
Enzyme preparation.

Single colonies grown on solid LB medium plus 100 µg/ml ampicillin were inoculated into flasks containing 50 ml complex liquid medium plus ampicillin. The cultures were aerated (280 rpm) at 37° C. to a cell density of 0.5 at 600 nm. IPTG (1 mM) was added and the cultures were aerated for 4 more hours. Cells were harvested by centrifugation (7,000 g, 30 min) and resuspended in buffer (20 ml) containing 50 mM sodium phosphate, pH 6.5, and 2 mM EDTA. Cells were centrifuged down using the same procedure and resuspended in the same buffer (10 ml). The cells were then disrupted by sonication. The release of cytoplasmic and periplasmic proteins was monitored by increased supernatant protein concentration. Cell debris was removed by centrifugation (15,000 g, 30 min).

Example 4
Enzyme and protein assays.

Unless otherwise stated, activities of enzymes towards various substrates were determined in a volume of 0.4 ml of 50 mM sodium phosphate buffer (SPB), pH 6.5, containing appropriate amounts of protein at 39° C. Soluble and insoluble substrates (0.2%, wt/vol) were used the same way except that insoluble substrates were stirred during pipetting and incubation. Phosphoric-acid-swollen cellulose (ASC) was prepared as described by Wood, T. M. 1988. Methods Enzymol. 60:19–25. Reducing sugars were quantified by the dinitrosalicylic acid (DNS) procedure (Miller, G. L. 1959. Anal. Chem. 31:426–428) using glucose as a standard. Before the absorption values were read using a spectrophotometer (Hewlett Packard), residual insoluble substrates were removed by centrifugation.

Activities of enzyme preparations towards p-nitrophenyl (PNP) linked substrates were performed by incubating a volume of 0.2 ml SPB containing 2 mM substrates at 39° C. for 15 min. Reactions were terminated by the addition of 1 ml of 1 M $Na_2CO_3$. The release of PNP was measured by measuring absorbance at 405 nm on a spectrophotometer; PNP was used as a standard. One unit (U) of activity is defined as the amount of enzymes required to release one 9.6 mol of glucose equivalent or of pNP per min. Buffers used to generate the pH range from 2.8 to 9.6 include 0.1 M sodium acetate (pH 2.8–5.4), sodium phosphate (pH 5.8–7.8), and sodium borate (pH 8.2–9.6).

Protein concentrations were measured by the MicroBCA reagent (Pierce Chemical Co., Rockford, Ill.) with bovine serum albumin as the standard.

Example 5
Thin Layer Chromatography.

Reaction solutions containing 200 µg *E. coli* cell lysate proteins and 1 mM cellodextrins, 0.2% (wt/vol) CMC, or ASC in 50 mM SPB, pH 6.5, were incubated at 39° C. for 5 h. The reactions were terminated by boiling the tubes for 5 min. Hydrolysis products were separated by thin layer chromatography (TLC) on silica gel plates (Analtech, Inc., Newark, Del.) using a solvent of chloroform:glacial acetic acid:water, 6:7:1 (vol/vol) (Lake and Goodwin. 1976. In: I. Smith and J. M. T. Seakins (ed.), Lipids, 4th ed., Vol. 1, pp. 345–366. Pitman Press, Bath, England). A mixture of glucose, cellobiose, cellotriose, and cellotetraose (Sigma Chemical Co., St. Louis, Mo.) was chromatographed under identical conditions, and the separated sugars were used as standards for the identification of hydrolysis products. After partition, the plates were sprayed with a reagent containing aniline (2 ml), diphenylamine (2 g), acetone (100 ml), and 85% $H_3PO_4$ (15 ml) and then sugars were visualized by heating the plates in an 105° C. oven for 15 min (Hansen, S. A. 1975. J. Chromatogr. 105:388–390).

Example 6
Viscosity determination.

A solution of 0.5% (wt/vol) high viscosity CMC (Sigma Chemical Co., St. Louis, Mo.) ill 5 ml SPB was incubated in a viscometer (10 ml) placed in a 40° C. water bath for 5 min. The viscosity was measured before and at different time points after the addition of 100 μl (0.5 mg) recombinant *E. coli* cell lysate proteins. Viscosity measurements using heat-inactivated (60° C., 1 h) *E. coli* cell lysate proteins under identical conditions were used as background. Reducing sugars in samples from the viscosity measurements were also determined using the DNS method described hereinabove.

Example 7

Cellulose binding.

Cell lysate proteins (200 μg) in 0.4 ml of 50 mM sodium phosphate buffer, pH 6.5 and various amounts of bovine serum albumin (B SA) were incubated with 100 mg Avicel PH 101 (Fluka Chemical Corp., Ronkonloma, N.Y.) which was washed twice with 5 volumes deionized $H_2O$ and dried before use. The Avicel/protein mixture was shaken at 4° C. for 30 min, followed by centrifugation (5,000 g, 20 min) at 4° C. to remove the Avicel. Activities of the samples towards barley β-1,3-1,4-glucan were measured under standard assay conditions. Barley β-1,3-1,4-glucan was used because the cellulases have much higher activity on it than on CMC.

Example 8

Isolation of celB and xynA clones.

For the isolation of cellulase celB cDNA clones, Orpinomcyes PC-2 mycelia were grown for 4 days in 20 liter carboys each containing 10 liters of basal medium (Barichievich and Calza. 1990, et al.) using 0.4% Avicel as carbon source. Mycelia were harvested by passing the culture through 4 layers of cheesecloth, and then the mycelial tissue was immediately frozen in liquid nitrogen. Frozen samples were ground in a mortar that was chilled using liquid nitrogen. Extraction of total RNA, purification of mRNA and construction of a cDNA library in lambda ZAPII were performed as previously described (Chen et al., 1995, supra) except that mRNA samples purified from Avicel and OSX-grown cultures were combined before they were used as templates for cDNA synthesis. Preparation of media and solutions, growth of *E. coli* host cells and amplification of the library were according to the instructions of the supplier (Stratagene, La, Jolla, Calif.) or as described in Sambrook et al. (1989) supra.

To isolate cellulase-producing plaques, top agar containing 5 mM IPTG and 0.2% RBB-CMC (InterSpex Products, Inc., Foster City, Calif.) was used. The lambda ZAPII library was screened for cellulase- and xylanase-producing clones. Cellulase-producing clones were identified as having clear haloes on a blue background due to diffusion of RBB after hydrolysis from the remazol brilliant blue-carboxymethylcellulose (RBB-CMC) as an indicator substrate. 21 initial positive clones were obtained when $2 \times 10^4$ pfu were plated. Ten of the initial clones were purified after a secondary screening, and they were converted to pBluescript plasmids by in vivo excision (Stratagene, La Jolla, Calif.). The other eleven initially positive clones were not studied further. Plasmid DNA from each of the ten randomly chosen clones was purified using the Qiagen plasmid purification system (Chatsworth, Calif.) after growth of the cultures in LB containing 50 μg/ml ampicillin. and digested with various restriction endonucleases. The restriction and Southern hybridization analysis indicated that these ten clones represented two distinct cDNA species. The longest insert of one species was 2.7 kb (celA) while the longest insert for the other species was 1.8 kb (celB).

Nucleotide sequences of the celB insert DNAs were determined using an automatic PCR sequencer (Applied Biosystems, Foster City, Calif.). Both universal and specific oligonucleotide primers were used in the sequencing of both strands of the inserts. The XynA amino acid sequence and the coding sequence are published (WP 96/36701).

Example 9

Northern hybridization analysis of celB and xynA.

Orpinomyces PC-2 mycelium was cultured for 3 days in media containing 1% Avicel or 1% OSX as carbon source. Extraction of RNA was as described above. Total RNA was fractionated on an 1.2% agarose gel containing formaldehyde (Sambrook et al., 1989, supra) and then transferred to a nylon membrane using a Turboblotter (Schleicher and Schuell, Keene, N.H.). Antisense RNA of pOC1 (celB) and pOX8 (xynA) in pBluescripts were transcribed by T7 polymerase, labeled with digoxigenin using an RNA labelling kit (Boehringer Mannheim, Indianapolis, Ind.) and used as hybridization probes. RNA-DNA hybridization, stringency washing and detection of digoxigenin on the membrane were performed using the Genius 7 kit (trademark of Boehringer Mannheim, Indianapolis, Ind.).

Example 10

PCR Analysis of celB and xynA.

Oligonucleotides priming opposite strands and corresponding to the 5' and 3' ends of the ORFs for celB (forward primer, AATGAAATTCTTAAATAGTCTTTG (SEQ ID NO:5); reverse primer, TTAGTAAGTTAATAAATACCA-CACC (SEQ ID NO:6; see FIG. 10 and SEQ ID NO:11) and xynA (forward primer, AATGAGAACTATTAAATTTT-TATTC (SEQ ID NO:7 and see SEQ ID NO:13); reverse primer, GTATTTTTCTGCTTATAAACCACA (SEQ ID NO:8); see FIG. 11) were synthesized. Genomic DNA of Orpinomyces PC-2 grown on glucose as the sole carbon source was isolated using the Easy DNA kit according to the manufacturer's instructions (Invitrogen, San Diego, Calif.). Both the genomic and cDNA regions were amplified by PCR using the Taq polymerase (Boehringer Mannheim) on a thermocycler (Perkin-Elmer Corporation, Norwalk, Conn.). PCR products were separated on 1.5% agarose gels and visualized by ethidium bromide staining and UV transillumination.

Example 11

Western Blotting.

Peptides OPX1 (ARRGLDFGSTKKATAYEYIG, SEQ ID NO:9), corresponding to amino acids 86–106 of XynA and OPX2 (GYKCCSDPKCVVYYIDDDGKWGVENNEWCG, SEQ ID NO:10) corresponding to amino acids 330–360 of XynA were synthesized and conjugated to a tetramerically branched lysine backbone (Posnett et al. 1988. J. Biol. Chem. 263:1719–1725). The homogeneity of each peptide was confirmed by HPLC and SDS-14% PAGE (Laemmli, 1970). The peptides (separately, 0.2 μg in 0.5 ml sterile distilled water) were each mixed with 0.5 ml Freund's complete adjuvant (Sigma Chemical Co., St. Louis, Mo.), emulsified in 4 ml syringes and injected into separate adult New Zealand rabbits. Two booster injections per rabbit were administered 3 and 6 weeks after the initial injection as described except that incomplete Freund's adjuvant was used for the boosters. Two weeks after the second boost, 50 ml blood was drawn from each rabbit and serum samples were prepared and frozen at −20° C. Antibody titer was determined using enzyme-linked immunosorbant assays before the antibody samples were diluted for Western blot analysis. *Neocallimastix frontalis* EB 188 (Li, X. -L. and R. E. Calza. 1991. Appl. Environ. Microbiol. 57:3331–3336) and Orpinomyces PC-2 were grown in 500 ml flasks each containing 250 ml medium for 4 days. Avicel was used as carbon source. Culture supernatants were obtained by passing the culture through 50 mesh nylon and concentrated 100 fold using a 200 ml tangential flow cell installed with a PM10 membrane (molecular weight cutoff 10 kDa, Amicon, Beverly, Mass.).

These results demonstrated that active polysaccharide hydrolases from an anaerobic rumen fungus were directly expressible in E. coli. By contrast, expression of polysaccharide hydrolase cDNA sequences from aerobic fungi has never been demonstrated in E. coli (Xue et al. (1992b). The differences between the polysaccharide hydrolytic enzymes of anaerobic and aerobic fungi represent fundamental differences in their structures and evolutionary history.

ADDITIONAL REFERENCES

Ali et al. 1995. FEMS Microbiol. Lett. 125:15–22.
Bayer et al. 1994. TIBTECH 12:379–386.
Black et al. 1994. Biochem. J. 299:381–387.
Brownlee, A. G. 1989. Nucl. Acids Res. 17:1327–1335.
Chen et al. 1995. In: Ballal, S. K. (ed.), Southern Association of Agricultural Scientists Bulkletin: Biochemistry and Biotechnology. 8:1–6.
Choi, S. K. and L. G. Ljungdahl. 1996. Biochemistry 35:4906–4910.
Choi, S. K. and L. G. Ljungdahl. 1996. Biochemistry 35:4897–4905.
Gerngross et al. 1993. Mol. Microbiol. 8:325–334.
Gomez de Segura, B. and Fevre, M. 1993. Appl. Environ. Microbiol. 5:3654–3660.
Orpin, C. G. 1975. J. Gen. Microbiol. 91:249–262.
Tamblyn Lee et al. 1993. J. Bacteriol. 175:1293–1302.
Wood, T. M. 1970. Biochem. J. 121:353–362
Wubah, D. A. and Kim, S. K. 1994. Studies of a novel obligate zoosporic fungus isolated from a pond. Abstracts of the 94th General Meeting of the American Society for Microbiology.
Wubah et al. 1991. Can. J. Bot. 69:1232–1236.
Xue et al. 1992. J. Gen. Microbiol. 138:2397–2403.
Yarlett et al. 1986. Biochem. J. 236:729–739.

TABLE 1

Codon usage of genes encoding cellulases (CelA, CelB, and CelC), a xylanase (XynA), and a cyclophilin (Cycb, Chen et al., 1995) of the anaerobic fungus Orpinomyces PC-2

| AA | Codon | CelA | CelB | CelC | XynA | CycB |
|---|---|---|---|---|---|---|
| Gly | GGG | 0 | 0 | 0 | 0 | 0 |
| Gly | GGA | 2 | 5 | 4 | 6 | 1 |
| Gly | GGT | 37 | 37 | 31 | 36 | 22 |
| Gly | GGC | 0 | 1 | 0 | 4 | 0 |
| Glu | GAG | 0 | 5 | 0 | 0 | 0 |
| Glu | GAA | 17 | 25 | 21 | 14 | 9 |
| Asp | GAT | 20 | 24 | 15 | 16 | 10 |
| Asp | GAC | 2 | 3 | 6 | 3 | 3 |
| Val | GTG | 0 | 1 | 0 | 0 | 0 |
| Val | GTA | 1 | 0 | 1 | 6 | 2 |
| Val | GTT | 16 | 16 | 25 | 14 | 15 |
| Val | GTC | 7 | 8 | 2 | 4 | 1 |
| Ala | GCG | 0 | 0 | 0 | 0 | 0 |
| Ala | GCA | 0 | 1 | 1 | 12 | 0 |
| Ala | GCT | 29 | 14 | 36 | 8 | 14 |
| Ala | GCC | 4 | 9 | 2 | 7 | 0 |
| Arg | AGG | 0 | 0 | 0 | 0 | 0 |
| Arg | AGA | 7 | 9 | 15 | 4 | 4 |
| Ser | AGT | 12 | 10 | 15 | 10 | 1 |
| Ser | AGC | 5 | 2 | 4 | 2 | 0 |
| Lys | AAG | 19 | 7 | 9 | 13 | 8 |
| Lys | AAA | 9 | 18 | 7 | 10 | 7 |
| Asn | AAT | 14 | 37 | 18 | 6 | 4 |
| Asn | AAC | 33 | 8 | 25 | 12 | 7 |
| Met | ATG | 7 | 9 | 8 | 4 | 4 |
| Ile | ATA | 0 | 1 | 0 | 0 | 0 |
| Ile | ATT | 18 | 23 | 16 | 8 | 13 |
| Ile | ATC | 2 | 9 | 2 | 5 | 1 |
| Thr | ACG | 1 | 0 | 0 | 0 | 0 |
| Thr | ACA | 1 | 3 | 2 | 3 | 0 |
| Thr | ACT | 19 | 22 | 26 | 17 | 14 |
| Thr | ACC | 4 | 6 | 3 | 17 | 4 |
| Trp | TGG | 10 | 16 | 10 | 13 | 1 |
| End | TGA | 0 | 0 | 0 | 0 | 0 |
| Cys | TGT | 15 | 11 | 14 | 13 | 1 |
| Cys | TGC | 1 | 2 | 2 | 0 | 0 |
| End | TAG | 0 | 0 | 0 | 0 | 0 |
| End | TAA | 1 | 1 | 1 | 1 | 1 |
| Tyr | TAT | 2 | 14 | 5 | 4 | 2 |
| Tyr | TAC | 19 | 8 | 17 | 14 | 3 |
| Leu | TTG | 0 | 1 | 0 | 4 | 0 |
| Leu | TTA | 11 | 16 | 13 | 5 | 8 |
| Phe | TTT | 1 | 8 | 4 | 4 | 5 |
| Phe | TTC | 9 | 11 | 10 | 8 | 7 |
| Ser | TCG | 0 | 0 | 0 | 0 | 0 |
| Ser | TCA | 1 | 3 | 2 | 1 | 2 |
| Ser | TCT | 12 | 5 | 14 | 6 | 5 |
| Ser | TCC | 5 | 7 | 3 | 3 | 2 |
| Arg | CGG | 0 | 0 | 0 | 0 | 0 |
| Arg | CGA | 0 | 0 | 0 | 0 | 0 |
| Arg | CGT | 6 | 7 | 6 | 9 | 4 |
| Arg | CGC | 0 | 1 | 1 | 0 | 0 |
| Gln | CAG | 0 | 0 | 0 | 0 | 0 |
| Gln | CAA | 25 | 12 | 5 | 19 | 3 |
| His | CAT | 1 | 6 | 2 | 2 | 1 |
| His | CAC | 4 | 1 | 4 | 2 | 2 |
| Leu | CTG | 0 | 0 | 0 | 0 | 0 |
| Leu | CTA | 0 | 1 | 0 | 0 | 0 |
| Leu | CTT | 11 | 12 | 12 | 5 | 4 |
| Leu | CTC | 1 | 0 | 0 | 1 | 1 |
| Pro | CCG | 0 | 0 | 0 | 0 | 0 |
| Pro | CCA | 20 | 11 | 21 | 5 | 7 |
| Pro | CCT | 0 | 3 | 0 | 2 | 0 |
| Pro | CCC | 0 | 0 | 0 | 1 | 0 |

TABLE 2

Relation of the catalytic domains of Orpinomyces CelA and CelC with other family B glycanases

| | | CelA | | CelC | |
|---|---|---|---|---|---|
| Enzyme | Size (aa) | Overlap (aa) | Identity (%) | Overlap (aa) | Identity (%) |
| N. patriciuram CelA | 428 | 332 | 65.0 | 325 | 60.5 |
| T. reesei CBHII | 471 | 431 | 29.0 | 128 | 41.4 |
| F. oxysporum CBHII | 462 | 366 | 31.7 | 242 | 31.8 |
| A. bisporus CBHII | 438 | 382 | 32.2 | 241 | 34.4 |
| P. chrysosporium CBHII | 460 | 400 | 30.8 | 131 | 37.4 |
| C. fimi CenA | 450 | 49 | 46.9 | 74 | 30.8 |
| T. fusca CelC | 426 | 50 | 54.0 | — | |
| Streptomyces CasA | 389 | 115 | 36.5 | 221 | 32.1 |
| M. cellulolyticum CelA | 458 | 271 | 31.7 | 253 | 30.8 |
| M. xanthus Eg1 | 387 | 261 | 29.9 | 252 | 34.1 |
| S. halstedii EG1 | 331 | 302 | 27.2 | 269 | 32.3 |

TABLE 3

Substrate specificities of the Orpinomyces cellulases expressed in E. coli.

| Substrate | CelA | ΔCelA | CelB | CelC |
|---|---|---|---|---|
| CMC | 100 | 100 | 100 | 100 |
| Avicel | 5.6 | 6.6 | 1.9 | 10.3 |
| ASC | 54.4 | 63.2 | 15.6 | 63.7 |
| Laminarin | ND | ND | ND | 19.6 |
| Lichenan | 139 | 142 | 116 | 171 |
| Barley β-glucan | 696 | 710 | 460 | 812 |
| Arabinogalactan | ND | ND | ND | 10.7 |
| Araban | ND | ND | ND | 28.4 |
| Galactan | ND | ND | ND | 16.7 |
| Pullulan | 11.0 | 8.2 | 10.2 | 20.3 |
| Gum, arabic | ND | ND | 5.3 | 17.6 |
| Pachyman | ND | ND | ND | 21.1 |
| Pustulan | ND | ND | ND | 17.2 |

[a]The rates of hydrolysis on substrates including mannan, starch, oat spelt xylan (0.7%, wt/vol), pNP-β-D-glucopyranoside, pNP-β-D-xylopyranoside, and pNP-β-D-cellobiose (1 mM) were less than 1.0% of those on CMC.
[b]ND means that the hydrolysis rate was less than 1.0% of that on CMC.

TABLE 4

Percentage of activity recovery of the E. coli expressed Orpinomyces cellulases treated with Avicel.

| BSA concentration | Recovery (%) | | | |
|---|---|---|---|---|
| (mg/ml) | Cel A | CelA | CelB | CelC |
| 0 | 92.3 | 91.0 | 96.6 | 43.7 |
| 5.0 | NT[a] | NT | NT | 42.5 |
| 20.0 | NT | NT | NT | 43.2 |

[a]NT means not tested

TABLE 5

Sequence relatedness of Orpinomyces PC-2 CelB and cellulases from other sources.

| Organism | Enzyme | Overlap (bp) | Identity (%) | Accession Number |
|---|---|---|---|---|
| N. patriciarum | CelB | 473 | 83.1 | Z31364 |
| Clostridium thermocellum | CelX | 374 | 39.0 | M22759 |
| C. cellulovorans | EngB | 375 | 40.0 | M75706 |
|  | EngD | 428 | 39.0 | M37434 |
| Ruminococcus albus | CelA | 345 | 44.6 | X54931 |
|  | CelB | 346 | 42.5 | X54932 |
| C. longisporum | CelA | 363 | 43.0 | LO2868 |
| R. flavefaciens | CelA | 323 | 38.4 | S55178 |
| Butyrivibrio fibrisolvens | End1 | 409 | 36.9 | X17538 |

What is claimed is:

1. A non-naturally occurring recombinant DNA molecule comprising a nucleotide sequence encoding an Orpinomyces cellulase protein having an amino acid sequence selected from the group consisting of an amino acid sequence set forth in SEQ ID NO:2, or an amino acid sequence having at least about 75% amino acid identity thereto to and substantially equivalent biological activity and SEQ ID NO:4 or an amino acid sequence having at least about 75% amino acid identity thereto and substantially equivalent biological activity.

2. The non-naturally occurring recombinant DNA molecule of claim 1 comprising the nucleotide sequence as set forth in SEQ ID NO:1 from nucleotide 105 to nucleotide 1484 or a sequence having at least about 75% nucleotide sequence homology thereto.

3. The non-naturally occurring recombinant DNA molecule of claim 1 comprising the nucleotide sequence as set forth in SEQ ID NO:3 from nucleotide 154 to 1503 or a nucleotide sequence having at least about 75% nucleotide sequence homology thereto.

4. A recombinant cell comprising a recombinant DNA molecule of claim 2.

5. A recombinant cell comprising a recombinant DNA molecule of claim 3.

6. The recombinant cell of claim 4 wherein said cell is *Saccharomyces cerevisiae, Escherichia coli,* Aspergillus, *Trichoderma reesei,* Pichia, Penicillium, Streptomyces or Bacillus.

7. The recombinant cell of claim 5 wherein said cell is *Saccharomyces cerevisiae, Escherichia coli,* Aspergillus, *Trichoderma reesei,* Pichia, Penicillium, Streptomyces or Bacillus.

8. A method for producing a recombinant cellulase derived from Orpinomyces in a host cell other than Orpinomyces, said method comprising the steps of:

(a) infecting or transforming said host cell with a recombinant DNA molecule of claim 1, wherein said recombinant DNA molecule comprises a promoter active in said host cell operably linked to the cellulase coding sequence;

(b) culturing the infected or transformed cell under conditions suitable for gene expression, whereby the recombinant cellulase is produced.

9. The method of claim 8, wherein said recombinant DNA molecule comprises the nucleotide sequence as set forth in SEQ ID NO:1 from nucleotide 105 to nucleotide 1484 or a sequence having at least about 75% nucleotide sequence homology thereto.

10. The method of claim 8, wherein said recombinant DNA molecule comprises the nucleotide sequence as set forth in SEQ ID NO:3 from nucleotide 154 to 1503 or a nucleotide sequence having at least about 75% nucleotide sequence homology thereto.

\* \* \* \* \*

SEQUENCE LISTING

<160> NUMBER OF SEQ ID NOS: 29

<210> SEQ ID NO 1
<211> LENGTH: 1558
<212> TYPE: DNA
<213> ORGANISM: Orpinomyces sp. PC-2
<220> FEATURE:
<221> NAME/KEY: CDS
<222> LOCATION: (105)..(1481)

<400> SEQUENCE: 1

```
ataagcaata attatatata gaacaataaa tagaaaagtt atttgaatca actttaaaac        60
ctacctatat ataaatagaa attttttttt ttagtattag aaaa atg aaa ttc tct       116
                                              Met Lys Phe Ser
                                                1 act gtt tta gct act tta ttc gct act gga gct ctt gct tct gaa tgt       164
Thr Val Leu Ala Thr Leu Phe Ala Thr Gly Ala Leu Ala Ser Glu Cys
  5                  10                  15                  20 cac tgg caa tac cca tgt tgt aaa gat tgt act gtt tac tac act gat       212
His Trp Gln Tyr Pro Cys Cys Lys Asp Cys Thr Val Tyr Tyr Thr Asp
                 25                  30                  35 act gaa ggt aag tgg ggt gtt tta aac aat gac tgg tgt atg att gat       260
Thr Glu Gly Lys Trp Gly Val Leu Asn Asn Asp Trp Cys Met Ile Asp
             40                  45                  50 aac aga cgt tgt agc agt aac aac aat aat tgt agc agc agt att acc       308
Asn Arg Arg Cys Ser Ser Asn Asn Asn Asn Cys Ser Ser Ser Ile Thr
         55                  60                  65 tct caa ggt tac cca tgc tgt agc aac aat aat tgt aag gta gaa tac       356
Ser Gln Gly Tyr Pro Cys Cys Ser Asn Asn Asn Cys Lys Val Glu Tyr
```

-continued

```
                70                      75                      80
act gat aat gat ggt aag tgg ggt gtt gaa aac aac aac tgg tgt ggt      404
Thr Asp Asn Asp Gly Lys Trp Gly Val Glu Asn Asn Asn Trp Cys Gly
 85                      90                      95                     100 att tcc aac agt tgt ggt ggt ggt caa caa caa caa cca acc caa cca      452
Ile Ser Asn Ser Cys Gly Gly Gly Gln Gln Gln Gln Pro Thr Gln Pro
                        105                     110                     115 act caa cca act caa cca caa caa cca act caa cca agt agt gat aac      500
Thr Gln Pro Thr Gln Pro Gln Gln Pro Thr Gln Pro Ser Ser Asp Asn
                120                     125                     130 ttc ttt gaa aat gaa att tac agt aac tac aag ttc caa gga gaa gtt      548
Phe Phe Glu Asn Glu Ile Tyr Ser Asn Tyr Lys Phe Gln Gly Glu Val
            135                     140                     145 gat att tct att aag aaa tta aat ggt gac tta aag gct aag gct gaa      596
Asp Ile Ser Ile Lys Lys Leu Asn Gly Asp Leu Lys Ala Lys Ala Glu
    150                     155                     160 aag gtc aaa tat gtt cca acg gct gtt tgg tta gct tgg gat ggt gct      644
Lys Val Lys Tyr Val Pro Thr Ala Val Trp Leu Ala Trp Asp Gly Ala
165                     170                     175                     180 cca caa gaa gtt cca aga tac ctt caa gaa gct ggt aac aag act gtt      692
Pro Gln Glu Val Pro Arg Tyr Leu Gln Glu Ala Gly Asn Lys Thr Val
                        185                     190                     195 gtt ttc gtc tta tat atg att cca act cgt gat tgt ggt gct aac gct      740
Val Phe Val Leu Tyr Met Ile Pro Thr Arg Asp Cys Gly Ala Asn Ala
                200                     205                     210 tct gct ggt ggt tct gct acc atc gat aaa tac aag ggt tac att aac      788
Ser Ala Gly Gly Ser Ala Thr Ile Asp Lys Tyr Lys Gly Tyr Ile Asn
        215                     220                     225 aac att tac aac act tcc aac caa tac aag aac tct aaa att gtt atg      836
Asn Ile Tyr Asn Thr Ser Asn Gln Tyr Lys Asn Ser Lys Ile Val Met
230                     235                     240 att ctt gaa cca gat act att ggt aac ctt gtt act aac aac aac gat      884
Ile Leu Glu Pro Asp Thr Ile Gly Asn Leu Val Thr Asn Asn Asn Asp
245                     250                     255                     260 aac tgt aga aat gtc aga aac atg cac aaa caa gcc ctt tct tac gct      932
Asn Cys Arg Asn Val Arg Asn Met His Lys Gln Ala Leu Ser Tyr Ala
                265                     270                     275 att agt aag ttc ggt act caa agt cac gtc aag gtt tac ctt gat gct      980
Ile Ser Lys Phe Gly Thr Gln Ser His Val Lys Val Tyr Leu Asp Ala
                280                     285                     290 gct cac ggt gct tgg tta aac caa tac gct gat caa aca gct aat gtc     1028
Ala His Gly Ala Trp Leu Asn Gln Tyr Ala Asp Gln Thr Ala Asn Val
        295                     300                     305 att aag gaa atc tta aat aac gct ggt agt ggt aag ctt cgt ggt att     1076
Ile Lys Glu Ile Leu Asn Asn Ala Gly Ser Gly Lys Leu Arg Gly Ile
310                     315                     320 agt act aat gtt tct aac tac caa tcc att gaa agt gaa tac aaa tac     1124
Ser Thr Asn Val Ser Asn Tyr Gln Ser Ile Glu Ser Glu Tyr Lys Tyr
325                     330                     335                     340 cat caa aac ctt aac aga gcc ctt gaa agt aaa ggt gtc aga ggt ctt     1172
His Gln Asn Leu Asn Arg Ala Leu Glu Ser Lys Gly Val Arg Gly Leu
                345                     350                     355 aag ttc att gtc gat act tct cgt aac ggt gct aac gtt gaa ggt gct     1220
Lys Phe Ile Val Asp Thr Ser Arg Asn Gly Ala Asn Val Glu Gly Ala
                360                     365                     370 ttc aat gcc tcc ggt acc tgg tgt aac ttc aag ggt gct ggt tta ggt     1268
Phe Asn Ala Ser Gly Thr Trp Cys Asn Phe Lys Gly Ala Gly Leu Gly
        375                     380                     385 caa cgt cca aag ggt aat cca aac cca ggt agc atg cca tta ctt gat     1316
```

```
Gln Arg Pro Lys Gly Asn Pro Asn Pro Gly Ser Met Pro Leu Leu Asp
            390                 395                 400 gcc tac atg tgg att aag act cca ggt gaa gct gat ggt tct tcc caa        1364
Ala Tyr Met Trp Ile Lys Thr Pro Gly Glu Ala Asp Gly Ser Ser Gln
405                 410                 415                 420 ggt tca aga gct gat cca gtt tgt gct cgt ggt gat tct ctc caa ggt        1412
Gly Ser Arg Ala Asp Pro Val Cys Ala Arg Gly Asp Ser Leu Gln Gly
                425                 430                 435 gct cca gat gct ggt tca tgg ttc cac gaa tac ttc acc atg tta atc        1460
Ala Pro Asp Ala Gly Ser Trp Phe His Glu Tyr Phe Thr Met Leu Ile
                440                 445                 450 caa aac gct aac cca cca ttc taagttaatc ataaatgaga aagaataaa            1511
Gln Asn Ala Asn Pro Pro Phe
            455 attatacatg tagaagaaaa tttttatttt ttatttattc taaaaaa                    1558
```

<210> SEQ ID NO 2
<211> LENGTH: 459
<212> TYPE: PRT
<213> ORGANISM: Orpinomyces sp. PC-2

<400> SEQUENCE: 2

```
Met Lys Phe Ser Thr Val Leu Ala Thr Leu Phe Ala Thr Gly Ala Leu
1               5                   10                  15

Ala Ser Glu Cys His Trp Gln Tyr Pro Cys Cys Lys Asp Cys Thr Val
            20                  25                  30

Tyr Tyr Thr Asp Thr Glu Gly Lys Trp Gly Val Leu Asn Asn Asp Trp
        35                  40                  45

Cys Met Ile Asp Asn Arg Arg Cys Ser Ser Asn Asn Asn Cys Ser
    50                  55                  60

Ser Ser Ile Thr Ser Gln Gly Tyr Pro Cys Cys Ser Asn Asn Asn Cys
65                  70                  75                  80

Lys Val Glu Tyr Thr Asp Asn Asp Gly Lys Trp Gly Val Glu Asn Asn
                85                  90                  95

Asn Trp Cys Gly Ile Ser Asn Ser Cys Gly Gly Gly Gln Gln Gln Gln
            100                 105                 110

Pro Thr Gln Pro Thr Gln Pro Thr Gln Pro Gln Gln Pro Thr Gln Pro
        115                 120                 125

Ser Ser Asp Asn Phe Phe Glu Asn Glu Ile Tyr Ser Asn Tyr Lys Phe
130                 135                 140

Gln Gly Glu Val Asp Ile Ser Ile Lys Lys Leu Asn Gly Asp Leu Lys
145                 150                 155                 160

Ala Lys Ala Glu Lys Val Lys Tyr Val Pro Thr Ala Val Trp Leu Ala
                165                 170                 175

Trp Asp Gly Ala Pro Gln Glu Val Pro Arg Tyr Leu Gln Glu Ala Gly
            180                 185                 190

Asn Lys Thr Val Val Phe Val Leu Tyr Met Ile Pro Thr Arg Asp Cys
        195                 200                 205

Gly Ala Asn Ala Ser Ala Gly Gly Ser Ala Thr Ile Asp Lys Tyr Lys
    210                 215                 220

Gly Tyr Ile Asn Asn Ile Tyr Asn Thr Ser Asn Gln Tyr Lys Asn Ser
225                 230                 235                 240

Lys Ile Val Met Ile Leu Glu Pro Asp Thr Ile Gly Asn Leu Val Thr
                245                 250                 255

Asn Asn Asn Asp Asn Cys Arg Asn Val Arg Asn Met His Lys Gln Ala
            260                 265                 270
```

-continued

```
Leu Ser Tyr Ala Ile Ser Lys Phe Gly Thr Gln Ser His Val Lys Val
        275                 280                 285
Tyr Leu Asp Ala Ala His Gly Ala Trp Leu Asn Gln Tyr Ala Asp Gln
    290                 295                 300
Thr Ala Asn Val Ile Lys Glu Ile Leu Asn Asn Ala Gly Ser Gly Lys
305                 310                 315                 320
Leu Arg Gly Ile Ser Thr Asn Val Ser Asn Tyr Gln Ser Ile Glu Ser
                325                 330                 335
Glu Tyr Lys Tyr His Gln Asn Leu Asn Arg Ala Leu Glu Ser Lys Gly
            340                 345                 350
Val Arg Gly Leu Lys Phe Ile Val Asp Thr Ser Arg Asn Gly Ala Asn
        355                 360                 365
Val Glu Gly Ala Phe Asn Ala Ser Gly Thr Trp Cys Asn Phe Lys Gly
    370                 375                 380
Ala Gly Leu Gly Gln Arg Pro Lys Gly Asn Pro Asn Pro Gly Ser Met
385                 390                 395                 400
Pro Leu Leu Asp Ala Tyr Met Trp Ile Lys Thr Pro Gly Glu Ala Asp
                405                 410                 415
Gly Ser Ser Gln Gly Ser Arg Ala Asp Pro Val Cys Ala Arg Gly Asp
            420                 425                 430
Ser Leu Gln Gly Ala Pro Asp Ala Gly Ser Trp Phe His Glu Tyr Phe
        435                 440                 445
Thr Met Leu Ile Gln Asn Ala Asn Pro Pro Phe
    450                 455

<210> SEQ ID NO 3
<211> LENGTH: 1628
<212> TYPE: DNA
<213> ORGANISM: Orpinomyces sp. PC-2
<220> FEATURE:
<221> NAME/KEY: CDS
<222> LOCATION: (154)..(1500)

<400> SEQUENCE: 3
```

| | | |
|---|---|---|
| attaaaatag cttaaatatt atattcatat tcactggttg aattgttata atattatata | 60 |
| ataaactgt gtatttatat aaaaaaaaat tatttatcat ttaataatat aaataaatta | 120 |
| ttaaaaaaaa aaaaaaataa attttataaa aaa atg aaa ttc tct gct tta att | 174 |

```
                                    Met Lys Phe Ser Ala Leu Ile
                                      1               5 agt act tta ttt gct gct gga gct atg gcc tcc aga tgt cat cca agt    222
Ser Thr Leu Phe Ala Ala Gly Ala Met Ala Ser Arg Cys His Pro Ser
         10                  15                  20 tac cca tgt tgt aac ggt tgt aac gtt gaa tac act gat act gaa ggt    270
Tyr Pro Cys Cys Asn Gly Cys Asn Val Glu Tyr Thr Asp Thr Glu Gly
     25                  30                  35 aat tgg ggt gta gaa aat ttt gat tgg tgt ttc att gat gaa agc cgt    318
Asn Trp Gly Val Glu Asn Phe Asp Trp Cys Phe Ile Asp Glu Ser Arg
 40                  45                  50                  55 tgt aat cca gga tac tgt aaa ttc gaa gct ctt ggt tac agt tgc tgt    366
Cys Asn Pro Gly Tyr Cys Lys Phe Glu Ala Leu Gly Tyr Ser Cys Cys
                 60                  65                  70 aag gga tgt gaa gtt gtt tac tct gat gaa gat ggt aat tgg ggt gtt    414
Lys Gly Cys Glu Val Val Tyr Ser Asp Glu Asp Gly Asn Trp Gly Val
             75                  80                  85 gaa aac caa caa tgg tgt ggt att aga gat aac tgt act cca aat gtt    462
Glu Asn Gln Gln Trp Cys Gly Ile Arg Asp Asn Cys Thr Pro Asn Val
         90                  95                 100
```

```
cca gcc act agt gct aga acc act acc aga act act act act act aga      510
Pro Ala Thr Ser Ala Arg Thr Thr Thr Arg Thr Thr Thr Thr Thr Arg
        105                 110                 115 act act act gtt aac tct ctt cca act agc gac aac ttc ttt gaa aat      558
Thr Thr Thr Val Asn Ser Leu Pro Thr Ser Asp Asn Phe Phe Glu Asn
120                 125                 130                 135 gaa ctt tac agt aac tac aaa ttc caa ggt gaa gtt gac caa tct att      606
Glu Leu Tyr Ser Asn Tyr Lys Phe Gln Gly Glu Val Asp Gln Ser Ile
                140                 145                 150 caa aga tta agt ggt tct tta caa gaa aag gct aag aaa gtt aag tac      654
Gln Arg Leu Ser Gly Ser Leu Gln Glu Lys Ala Lys Lys Val Lys Tyr
        155                 160                 165 gtt cca act gct gct tgg tta gct tgg agt ggt gct aca aat gaa gtt      702
Val Pro Thr Ala Ala Trp Leu Ala Trp Ser Gly Ala Thr Asn Glu Val
        170                 175                 180 gca aga tac ctt aat gaa gct ggt tca aag act gtt gtc ttc gtt tta      750
Ala Arg Tyr Leu Asn Glu Ala Gly Ser Lys Thr Val Val Phe Val Leu
        185                 190                 195 tat atg att cca act cgt gat tgt aat gct ggt ggt tct aat ggt ggt      798
Tyr Met Ile Pro Thr Arg Asp Cys Asn Ala Gly Gly Ser Asn Gly Gly
200                 205                 210                 215 gct gat aac ctt tct aca tac caa gga tac gtt aac agt atc tac aac      846
Ala Asp Asn Leu Ser Thr Tyr Gln Gly Tyr Val Asn Ser Ile Tyr Asn
                220                 225                 230 act att aac caa tat cca aac tct aga atc gtt atg att att gaa cca      894
Thr Ile Asn Gln Tyr Pro Asn Ser Arg Ile Val Met Ile Ile Glu Pro
        235                 240                 245 gat act att ggt aat ctt gtt act gct aac aat gct aac tgt aga aat      942
Asp Thr Ile Gly Asn Leu Val Thr Ala Asn Asn Ala Asn Cys Arg Asn
        250                 255                 260 gtc cat gac atg cac aaa caa gct ctt tcc tat gct att agt aag ttc      990
Val His Asp Met His Lys Gln Ala Leu Ser Tyr Ala Ile Ser Lys Phe
        265                 270                 275 ggt act caa aag aac gtt aga gtt tac ctt gat gct gct cac ggt ggt     1038
Gly Thr Gln Lys Asn Val Arg Val Tyr Leu Asp Ala Ala His Gly Gly
280                 285                 290                 295 tgg tta aac agc agt gct gac aga act gct gaa gtt att gct gaa att     1086
Trp Leu Asn Ser Ser Ala Asp Arg Thr Ala Glu Val Ile Ala Glu Ile
                300                 305                 310 tta aga aat gct ggt aat ggt aag att cgt ggt att agt act aat gtt     1134
Leu Arg Asn Ala Gly Asn Gly Lys Ile Arg Gly Ile Ser Thr Asn Val
        315                 320                 325 tct aac tac caa cca gtt tac agt gaa tac caa tat cac caa aac ctt     1182
Ser Asn Tyr Gln Pro Val Tyr Ser Glu Tyr Gln Tyr His Gln Asn Leu
        330                 335                 340 aac aga gct ctt gaa agt aga ggt gtt cgc ggt atg aaa ttc att gtt     1230
Asn Arg Ala Leu Glu Ser Arg Gly Val Arg Gly Met Lys Phe Ile Val
        345                 350                 355 gat act tct cgt aac ggt aga aac cca tct tct gct acc tgg tgt aac     1278
Asp Thr Ser Arg Asn Gly Arg Asn Pro Ser Ser Ala Thr Trp Cys Asn
360                 365                 370                 375 ctt aag ggt gct ggt tta ggt gct cgt cca caa gct aac cca gat cca     1326
Leu Lys Gly Ala Gly Leu Gly Ala Arg Pro Gln Ala Asn Pro Asp Pro
                380                 385                 390 aat atg cca tta ctt gat gct tat gtt tgg att aaa act cca ggt gaa     1374
Asn Met Pro Leu Leu Asp Ala Tyr Val Trp Ile Lys Thr Pro Gly Glu
        395                 400                 405 tct gac agt gct tcc agt gct gat cca gtt tgc cgt aac agc gac tct     1422
Ser Asp Ser Ala Ser Ser Ala Asp Pro Val Cys Arg Asn Ser Asp Ser
```

-continued

```
           410                 415                 420
tta caa ggt gct cca gct gct ggt tca tgg ttc cac gat tac ttt gtt    1470
Leu Gln Gly Ala Pro Ala Ala Gly Ser Trp Phe His Asp Tyr Phe Val
        425                 430                 435 atg tta tta gaa aat gct aac cca cca ttc taagcaatta aaaatacctt      1520
Met Leu Leu Glu Asn Ala Asn Pro Pro Phe
440                 445 tatattttaa gataattaat ataaaataga aagaaaatt ttattttttc tatttaattt    1580
agaaatgtat tattaataat taaaatttag aagggaaaaa gaaaaaaa              1628
```

<210> SEQ ID NO 4
<211> LENGTH: 449
<212> TYPE: PRT
<213> ORGANISM: Orpinomyces sp. PC-2

<400> SEQUENCE: 4

```
Met Lys Phe Ser Ala Leu Ile Ser Thr Leu Phe Ala Ala Gly Ala Met
  1               5                  10                  15

Ala Ser Arg Cys His Pro Ser Tyr Pro Cys Cys Asn Gly Cys Asn Val
             20                  25                  30

Glu Tyr Thr Asp Thr Glu Gly Asn Trp Gly Val Glu Asn Phe Asp Trp
         35                  40                  45

Cys Phe Ile Asp Glu Ser Arg Cys Asn Pro Gly Tyr Cys Lys Phe Glu
     50                  55                  60

Ala Leu Gly Tyr Ser Cys Cys Lys Gly Cys Glu Val Val Tyr Ser Asp
 65                  70                  75                  80

Glu Asp Gly Asn Trp Gly Val Glu Asn Gln Gln Trp Cys Gly Ile Arg
                 85                  90                  95

Asp Asn Cys Thr Pro Asn Val Pro Ala Thr Ser Ala Arg Thr Thr Thr
            100                 105                 110

Arg Thr Thr Thr Thr Arg Thr Thr Val Asn Ser Leu Pro Thr
        115                 120                 125

Ser Asp Asn Phe Phe Glu Asn Glu Leu Tyr Ser Asn Tyr Lys Phe Gln
    130                 135                 140

Gly Glu Val Asp Gln Ser Ile Gln Arg Leu Ser Gly Ser Leu Gln Glu
145                 150                 155                 160

Lys Ala Lys Lys Val Lys Tyr Val Pro Thr Ala Ala Trp Leu Ala Trp
                165                 170                 175

Ser Gly Ala Thr Asn Glu Val Ala Arg Tyr Leu Asn Glu Ala Gly Ser
            180                 185                 190

Lys Thr Val Val Phe Val Leu Tyr Met Ile Pro Thr Arg Asp Cys Asn
        195                 200                 205

Ala Gly Gly Ser Asn Gly Gly Ala Asp Asn Leu Ser Thr Tyr Gln Gly
    210                 215                 220

Tyr Val Asn Ser Ile Tyr Asn Thr Ile Asn Gln Tyr Pro Asn Ser Arg
225                 230                 235                 240

Ile Val Met Ile Ile Glu Pro Asp Thr Ile Gly Asn Leu Val Thr Ala
                245                 250                 255

Asn Asn Ala Asn Cys Arg Asn Val His Asp Met His Lys Gln Ala Leu
            260                 265                 270

Ser Tyr Ala Ile Ser Lys Phe Gly Thr Gln Lys Asn Val Arg Val Tyr
        275                 280                 285

Leu Asp Ala Ala His Gly Gly Trp Leu Asn Ser Ser Ala Asp Arg Thr
    290                 295                 300
```

```
Ala Glu Val Ile Ala Glu Ile Leu Arg Asn Ala Gly Asn Gly Lys Ile
305                 310                 315                 320

Arg Gly Ile Ser Thr Asn Val Ser Asn Tyr Gln Pro Val Tyr Ser Glu
            325                 330                 335

Tyr Gln Tyr His Gln Asn Leu Asn Arg Ala Leu Glu Ser Arg Gly Val
            340                 345                 350

Arg Gly Met Lys Phe Ile Val Asp Thr Ser Arg Asn Gly Arg Asn Pro
        355                 360                 365

Ser Ser Ala Thr Trp Cys Asn Leu Lys Gly Ala Gly Leu Gly Ala Arg
        370                 375                 380

Pro Gln Ala Asn Pro Asp Pro Asn Met Pro Leu Leu Asp Ala Tyr Val
385                 390                 395                 400

Trp Ile Lys Thr Pro Gly Glu Ser Asp Ser Ala Ser Ser Ala Asp Pro
            405                 410                 415

Val Cys Arg Asn Ser Asp Ser Leu Gln Gly Ala Pro Ala Ala Gly Ser
            420                 425                 430

Trp Phe His Asp Tyr Phe Val Met Leu Leu Glu Asn Ala Asn Pro Pro
        435                 440                 445

Phe

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
aatgaaattc ttaaatagtc tttg                                      24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ttagtaagtt aataaatacc acacc                                     25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
aatgagaact tattaaattt ttattc                                    26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
```

```
gtatttttct gcttataaac caca                                              24
```

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence:
      oligopeptide

<400> SEQUENCE: 9

Ala Arg Arg Gly Leu Asp Phe Gly Ser Thr Lys Lys Ala Thr Ala Tyr
 1               5                  10                  15

Glu Tyr Ile Gly
            20

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence:oligopeptide

<400> SEQUENCE: 10

Gly Tyr Lys Cys Cys Ser Asp Pro Lys Cys Val Val Tyr Tyr Ile Asp
 1               5                  10                  15

Asp Asp Gly Lys Trp Gly Val Glu Asn Asn Glu Trp Cys Gly
            20                  25                  30

<210> SEQ ID NO 11
<211> LENGTH: 1826
<212> TYPE: DNA
<213> ORGANISM: Orpinomyces sp. PC-2
<220> FEATURE:
<221> NAME/KEY: CDS
<222> LOCATION: (69)..(1481)

<400> SEQUENCE: 11

```
taatcttctc ttatttttt  ttcttttcta taattaatat taaaaaaaat taaaataaat       60 atttaaaa atg aaa ttc tta aat agt ctt tct tta ctt gga tta gtt att      110
         Met Lys Phe Leu Asn Ser Leu Ser Leu Leu Gly Leu Val Ile
          1               5                  10 gct gga tgt gaa gct atg aga aat att tca tcc aaa gaa tta gtt aaa      158
Ala Gly Cys Glu Ala Met Arg Asn Ile Ser Ser Lys Glu Leu Val Lys
 15                  20                  25                  30 gaa tta act att ggt tgg agt tta ggt aat acc tta gat gca tcc tgt      206
Glu Leu Thr Ile Gly Trp Ser Leu Gly Asn Thr Leu Asp Ala Ser Cys
             35                  40                  45 gtg gag act tta aat tat agt aaa gat caa aca gct tct gaa act tgt      254
Val Glu Thr Leu Asn Tyr Ser Lys Asp Gln Thr Ala Ser Glu Thr Cys
         50                  55                  60 tgg ggt aat gtt aaa act act caa gag ctt tac tat aaa cta agt gat      302
Trp Gly Asn Val Lys Thr Thr Gln Glu Leu Tyr Tyr Lys Leu Ser Asp
     65                  70                  75 ctt ggt ttc aac act ttc cgt att cct act act tgg agt ggt cat ttt      350
Leu Gly Phe Asn Thr Phe Arg Ile Pro Thr Thr Trp Ser Gly His Phe
 80                  85                  90 ggt gat gct cct gac tat aaa att agt gat gtt tgg atg aaa aga gtt      398
Gly Asp Ala Pro Asp Tyr Lys Ile Ser Asp Val Trp Met Lys Arg Val
 95                  100                 105                 110 cat gaa gtt gtc gat tat gct ctt aac act ggt ggt tat gcc atc tta      446
His Glu Val Val Asp Tyr Ala Leu Asn Thr Gly Gly Tyr Ala Ile Leu
                 115                 120                 125
```

```
aac att cac cat gaa act tgg aat tat gct ttc caa aag aat tta gag      494
Asn Ile His His Glu Thr Trp Asn Tyr Ala Phe Gln Lys Asn Leu Glu
        130                 135                 140 agt gcc aaa aag atc tta gtt gcc atc tgg aaa caa att gct gct gaa      542
Ser Ala Lys Lys Ile Leu Val Ala Ile Trp Lys Gln Ile Ala Ala Glu
                145                 150                 155 ttt ggt gat tat gat gaa cat tta att ttc gaa gga atg aat gaa cca      590
Phe Gly Asp Tyr Asp Glu His Leu Ile Phe Glu Gly Met Asn Glu Pro
    160                 165                 170 aga aag gtt ggg gat cca gct gaa tgg aca ggt ggt gat caa gaa ggt      638
Arg Lys Val Gly Asp Pro Ala Glu Trp Thr Gly Gly Asp Gln Glu Gly
175                 180                 185                 190 tgg aat ttc gtc aat gaa atg aat gcc ctt ttc gtt aaa act att cgt      686
Trp Asn Phe Val Asn Glu Met Asn Ala Leu Phe Val Lys Thr Ile Arg
                195                 200                 205 gcc act gga ggt aac aat gcc aat cgt cat ctt atg att cca acc tat      734
Ala Thr Gly Gly Asn Asn Ala Asn Arg His Leu Met Ile Pro Thr Tyr
        210                 215                 220 gct gcc tct gtt aat gat ggt tca att aat aat ttc aaa tat cca aat      782
Ala Ala Ser Val Asn Asp Gly Ser Ile Asn Asn Phe Lys Tyr Pro Asn
                225                 230                 235 ggg gat gat aaa gtc att gtt tcc ctt cat tcc tac agt cca tac aat      830
Gly Asp Asp Lys Val Ile Val Ser Leu His Ser Tyr Ser Pro Tyr Asn
    240                 245                 250 ttt gcc tta aat aat ggt cca ggt gct atc agt aat ttt tat gat ggt      878
Phe Ala Leu Asn Asn Gly Pro Gly Ala Ile Ser Asn Phe Tyr Asp Gly
255                 260                 265                 270 aat gaa att gat tgg gtc atg aat act att aac tcc tcc ttc atc agc      926
Asn Glu Ile Asp Trp Val Met Asn Thr Ile Asn Ser Ser Phe Ile Ser
                275                 280                 285 aaa ggt att cct gtc atc att ggt gaa ttt gtt gct atg aac cgt gac      974
Lys Gly Ile Pro Val Ile Ile Gly Glu Phe Val Ala Met Asn Arg Asp
        290                 295                 300 aat gaa gat gac cgt gaa aga tgg caa gaa tat tat att aag aaa gcc     1022
Asn Glu Asp Asp Arg Glu Arg Trp Gln Glu Tyr Tyr Ile Lys Lys Ala
                305                 310                 315 act gct ctt ggt att cca tgt gtt atc tgg gat aat ggt tac ttt gag     1070
Thr Ala Leu Gly Ile Pro Cys Val Ile Trp Asp Asn Gly Tyr Phe Glu
    320                 325                 330 ggt gaa ggt gaa cgc ttt ggt atc att gat cgt aaa tcc tta aat gtc     1118
Gly Glu Gly Glu Arg Phe Gly Ile Ile Asp Arg Lys Ser Leu Asn Val
335                 340                 345                 350 att ttc cca aaa ctt atc aat ggt tta atg aaa ggt tta ggt gat gag     1166
Ile Phe Pro Lys Leu Ile Asn Gly Leu Met Lys Gly Leu Gly Asp Glu
                355                 360                 365 aag cca aag act aca ata aga aga act acc act act gtt caa gtc         1214
Lys Pro Lys Thr Thr Ile Arg Arg Thr Thr Thr Thr Val Gln Val
        370                 375                 380 caa cca act att aat aat gaa tgc ttc agt act aga ctt ggt tac agc     1262
Gln Pro Thr Ile Asn Asn Glu Cys Phe Ser Thr Arg Leu Gly Tyr Ser
                385                 390                 395 tgt tgt aat ggt ttt gat gtc ttg tac act gat aat gat gga caa tgg     1310
Cys Cys Asn Gly Phe Asp Val Leu Tyr Thr Asp Asn Asp Gly Gln Trp
    400                 405                 410 ggt gtt gaa aac ggc aat tgg tgt ggt att aag tca tct tgt ggt aac     1358
Gly Val Glu Asn Gly Asn Trp Cys Gly Ile Lys Ser Ser Cys Gly Asn
415                 420                 425                 430 aat caa cgt caa tgc tgg tct gaa aga ctt ggt tac cca tgt tgt caa     1406
Asn Gln Arg Gln Cys Trp Ser Glu Arg Leu Gly Tyr Pro Cys Cys Gln
                435                 440                 445
```

-continued

```
tat acc acc aat gct gaa tac acc gat aat gat ggt aga tgg ggt gtt    1454
Tyr Thr Thr Asn Ala Glu Tyr Thr Asp Asn Asp Gly Arg Trp Gly Val
            450                 455                 460 gaa aat ggt aat tgg tgt ggt att tat taacttacta aataattttt           1501
Glu Asn Gly Asn Trp Cys Gly Ile Tyr
            465             470 tacaaacata aataaattat ttagtaaaat aaaaaagaaa taaattttta aaaaaatata   1561
tttatatatt atgttataaa taataataaa taaatataga aattactata gtatatagaa   1621
aatatataca taaacaaaag taaaaaatta aaaattttta gtattgtata aattttatta   1681
aaaagtttaa taaatgataa aaaaaaatat taaacattt ggatgtattt gcatatcaaa    1741
gaaataataa taaatacttt aaaagcataa aattgataaa taattcataa ttaaacacat   1801
acttttaaac aattttaaaa taaaa                                         1826
```

<210> SEQ ID NO 12
<211> LENGTH: 471
<212> TYPE: PRT
<213> ORGANISM: Orpinomyces sp. PC-2

<400> SEQUENCE: 12

```
Met Lys Phe Leu Asn Ser Leu Ser Leu Leu Gly Leu Val Ile Ala Gly
  1               5                  10                  15

Cys Glu Ala Met Arg Asn Ile Ser Ser Lys Glu Leu Val Lys Glu Leu
                 20                  25                  30

Thr Ile Gly Trp Ser Leu Gly Asn Thr Leu Asp Ala Ser Cys Val Glu
             35                  40                  45

Thr Leu Asn Tyr Ser Lys Asp Gln Thr Ala Ser Glu Thr Cys Trp Gly
         50                  55                  60

Asn Val Lys Thr Thr Gln Glu Leu Tyr Tyr Lys Leu Ser Asp Leu Gly
 65                  70                  75                  80

Phe Asn Thr Phe Arg Ile Pro Thr Thr Trp Ser Gly His Phe Gly Asp
                 85                  90                  95

Ala Pro Asp Tyr Lys Ile Ser Asp Val Trp Met Lys Arg Val His Glu
                100                 105                 110

Val Val Asp Tyr Ala Leu Asn Thr Gly Gly Tyr Ala Ile Leu Asn Ile
            115                 120                 125

His His Glu Thr Trp Asn Tyr Ala Phe Gln Lys Asn Leu Glu Ser Ala
        130                 135                 140

Lys Lys Ile Leu Val Ala Ile Trp Lys Gln Ile Ala Ala Glu Phe Gly
145                 150                 155                 160

Asp Tyr Asp Glu His Leu Ile Phe Glu Gly Met Asn Glu Pro Arg Lys
                165                 170                 175

Val Gly Asp Pro Ala Glu Trp Thr Gly Gly Asp Gln Glu Gly Trp Asn
            180                 185                 190

Phe Val Asn Glu Met Asn Ala Leu Phe Val Lys Thr Ile Arg Ala Thr
        195                 200                 205

Gly Gly Asn Asn Ala Asn Arg His Leu Met Ile Pro Thr Tyr Ala Ala
    210                 215                 220

Ser Val Asn Asp Gly Ser Ile Asn Asn Phe Lys Tyr Pro Asn Gly Asp
225                 230                 235                 240

Asp Lys Val Ile Val Ser Leu His Ser Tyr Ser Pro Tyr Asn Phe Ala
                245                 250                 255

Leu Asn Asn Gly Pro Gly Ala Ile Ser Asn Phe Tyr Asp Gly Asn Glu
            260                 265                 270
```

```
Ile Asp Trp Val Met Asn Thr Ile Asn Ser Ser Phe Ile Ser Lys Gly
        275                 280                 285

Ile Pro Val Ile Ile Gly Glu Phe Val Ala Met Asn Arg Asp Asn Glu
    290                 295                 300

Asp Asp Arg Glu Arg Trp Gln Glu Tyr Tyr Ile Lys Lys Ala Thr Ala
305                 310                 315                 320

Leu Gly Ile Pro Cys Val Ile Trp Asp Asn Gly Tyr Phe Glu Gly Glu
                325                 330                 335

Gly Glu Arg Phe Gly Ile Ile Asp Arg Lys Ser Leu Asn Val Ile Phe
            340                 345                 350

Pro Lys Leu Ile Asn Gly Leu Met Lys Gly Leu Gly Asp Glu Lys Pro
        355                 360                 365

Lys Thr Thr Ile Arg Arg Thr Thr Thr Thr Val Gln Val Gln Pro
370                 375                 380

Thr Ile Asn Asn Glu Cys Phe Ser Thr Arg Leu Gly Tyr Ser Cys Cys
385                 390                 395                 400

Asn Gly Phe Asp Val Leu Tyr Thr Asp Asn Asp Gly Gln Trp Gly Val
                405                 410                 415

Glu Asn Gly Asn Trp Cys Gly Ile Lys Ser Ser Cys Gly Asn Asn Gln
            420                 425                 430

Arg Gln Cys Trp Ser Glu Arg Leu Gly Tyr Pro Cys Cys Gln Tyr Thr
        435                 440                 445

Thr Asn Ala Glu Tyr Thr Asp Asn Asp Gly Arg Trp Gly Val Glu Asn
    450                 455                 460

Gly Asn Trp Cys Gly Ile Tyr
465                 470

<210> SEQ ID NO 13
<211> LENGTH: 1221
<212> TYPE: DNA
<213> ORGANISM: Orpinomyces sp. PC-2
<220> FEATURE:
<221> NAME/KEY: CDS
<222> LOCATION: (97)..(1182)

<400> SEQUENCE: 13
ggcacgagga aatttttttt actggttaaa aaaaattat aaaactaaat aaataaaaaa      60
aatatttttt gaaatatatt aaaataggaa aaaaaa atg aga act att aaa ttt     114
                                        Met Arg Thr Ile Lys Phe
                                          1               5 tta ttc gca tta gct att aca acc gtt gct aag gcc caa tgg ggt gga    162
Leu Phe Ala Leu Ala Ile Thr Thr Val Ala Lys Ala Gln Trp Gly Gly
            10                  15                  20 aac ggt ggt gcc tct gct ggt caa aga tta agc gtt ggt ggt ggt caa    210
Asn Gly Gly Ala Ser Ala Gly Gln Arg Leu Ser Val Gly Gly Gly Gln
        25                  30                  35 aac caa cat aaa ggt gtt ttt gat ggc ttc agt tat gaa atc tgg tta    258
Asn Gln His Lys Gly Val Phe Asp Gly Phe Ser Tyr Glu Ile Trp Leu
    40                  45                  50 gat aac acc ggt ggt agt ggt tcc atg acc ctt ggt aaa ggt gca acc    306
Asp Asn Thr Gly Gly Ser Gly Ser Met Thr Leu Gly Lys Gly Ala Thr
55                  60                  65                  70 ttc aag gct gaa tgg agt gca gct gtt aac cgt ggt aac ttc ctt gcc    354
Phe Lys Ala Glu Trp Ser Ala Ala Val Asn Arg Gly Asn Phe Leu Ala
                75                  80                  85 cgt cgt ggt ctt gat ttc ggt tct acc aaa aag gca acc gct tac gaa    402
Arg Arg Gly Leu Asp Phe Gly Ser Thr Lys Lys Ala Thr Ala Tyr Glu
```

```
tac atc gga ttg gat tat gaa gca agt tac aga caa act gcc agc gca    450
Tyr Ile Gly Leu Asp Tyr Glu Ala Ser Tyr Arg Gln Thr Ala Ser Ala
        105                 110                 115 agt ggt aac tcc cgt ctt tgt gta tac ggc tgg ttc caa aac cgt gga    498
Ser Gly Asn Ser Arg Leu Cys Val Tyr Gly Trp Phe Gln Asn Arg Gly
    120                 125                 130 gtt caa ggc gta cct ttg gta gaa tac tac atc att gaa gat tgg gtt    546
Val Gln Gly Val Pro Leu Val Glu Tyr Tyr Ile Ile Glu Asp Trp Val
135                 140                 145                 150 gac tgg gta cca gat gca caa gga aaa atg gta acc atc gat ggt gca    594
Asp Trp Val Pro Asp Ala Gln Gly Lys Met Val Thr Ile Asp Gly Ala
            155                 160                 165 caa tat aag att ttc caa atg gat cac act ggt cca act atc aat ggt    642
Gln Tyr Lys Ile Phe Gln Met Asp His Thr Gly Pro Thr Ile Asn Gly
                170                 175                 180 ggt aat gaa acc ttt aag caa tac ttc agt gtc cgt caa caa aag aga    690
Gly Asn Glu Thr Phe Lys Gln Tyr Phe Ser Val Arg Gln Gln Lys Arg
            185                 190                 195 act tct ggt cat att act gta tca gat cac ttt aag gca tgg tcc aat    738
Thr Ser Gly His Ile Thr Val Ser Asp His Phe Lys Ala Trp Ser Asn
        200                 205                 210 caa ggt tgg ggt att gga aac ctc tat gaa gtt gca ttg aac gca gaa    786
Gln Gly Trp Gly Ile Gly Asn Leu Tyr Glu Val Ala Leu Asn Ala Glu
215                 220                 225                 230 ggt tgg caa agt agt ggt gtc gct gac gtc ccc aag ttg gat gtc tac    834
Gly Trp Gln Ser Ser Gly Val Ala Asp Val Pro Lys Leu Asp Val Tyr
                235                 240                 245 acc acc aaa caa ggt tct gct cct cgt act acc acc act acc cgt        882
Thr Thr Lys Gln Gly Ser Ala Pro Arg Thr Thr Thr Thr Thr Arg
            250                 255                 260 act act acc cgt act act aca aaa aca ctt cca acc act aat aaa aaa    930
Thr Thr Thr Arg Thr Thr Thr Lys Thr Leu Pro Thr Thr Asn Lys Lys
        265                 270                 275 tgt tct gcc aag att act gcc caa ggt tac aag tgt tgt agt gat cca    978
Cys Ser Ala Lys Ile Thr Ala Gln Gly Tyr Lys Cys Cys Ser Asp Pro
    280                 285                 290 aat tgt gtt gtt tac tac act gat gaa gat ggt acc tgg ggt gtt gaa    1026
Asn Cys Val Val Tyr Tyr Thr Asp Glu Asp Gly Thr Trp Gly Val Glu
295                 300                 305                 310 aac aat caa tgg tgt gga tgt ggt gtt gaa gca tgt tct ggc aag att    1074
Asn Asn Gln Trp Cys Gly Cys Gly Val Glu Ala Cys Ser Gly Lys Ile
                315                 320                 325 act gcc caa ggt tac aag tgt tgt agt gat cca aag tgt gtt gtt tac    1122
Thr Ala Gln Gly Tyr Lys Cys Cys Ser Asp Pro Lys Cys Val Val Tyr
            330                 335                 340 tac act gat gac gat ggt aaa tgg ggt gtt gaa aac aac gaa tgg tgt    1170
Tyr Thr Asp Asp Asp Gly Lys Trp Gly Val Glu Asn Asn Glu Trp Cys
        345                 350                 355 ggt tgt ggt tta taagcagaaa aatactaatt tagtaaaaaa aaaaaaaa         1221
Gly Cys Gly Leu
        360
```

<210> SEQ ID NO 14
<211> LENGTH: 362
<212> TYPE: PRT
<213> ORGANISM: Orpinomyces sp. PC-2

<400> SEQUENCE: 14

Met Arg Thr Ile Lys Phe Leu Phe Ala Leu Ala Ile Thr Thr Val Ala

```
              1               5              10              15
            Lys Ala Gln Trp Gly Gly Asn Gly Ala Ser Ala Gly Gln Arg Leu
                            20              25              30

Ser Val Gly Gly Gly Gln Asn Gln His Lys Gly Val Phe Asp Gly Phe
                        35              40              45

Ser Tyr Glu Ile Trp Leu Asp Asn Thr Gly Ser Gly Ser Met Thr
                    50              55              60

Leu Gly Lys Gly Ala Thr Phe Lys Ala Glu Trp Ser Ala Val Asn
            65                  70              75              80

Arg Gly Asn Phe Leu Ala Arg Arg Gly Leu Asp Phe Gly Ser Thr Lys
                            85              90              95

Lys Ala Thr Ala Tyr Glu Tyr Ile Gly Leu Asp Tyr Glu Ala Ser Tyr
                        100             105             110

Arg Gln Thr Ala Ser Ala Ser Gly Asn Ser Arg Leu Cys Val Tyr Gly
                        115             120             125

Trp Phe Gln Asn Arg Gly Val Gln Gly Val Pro Leu Val Glu Tyr Tyr
                    130             135             140

Ile Ile Glu Asp Trp Val Asp Trp Val Pro Asp Ala Gln Gly Lys Met
            145                 150             155             160

Val Thr Ile Asp Gly Ala Gln Tyr Lys Ile Phe Gln Met Asp His Thr
                            165             170             175

Gly Pro Thr Ile Asn Gly Gly Asn Glu Thr Phe Lys Gln Tyr Phe Ser
                        180             185             190

Val Arg Gln Gln Lys Arg Thr Ser Gly His Ile Thr Val Ser Asp His
                        195             200             205

Phe Lys Ala Trp Ser Asn Gln Gly Trp Gly Ile Gly Asn Leu Tyr Glu
                    210             215             220

Val Ala Leu Asn Ala Glu Gly Trp Gln Ser Ser Gly Val Ala Asp Val
            225                 230             235             240

Pro Lys Leu Asp Val Tyr Thr Thr Lys Gln Gly Ser Ala Pro Arg Thr
                            245             250             255

Thr Thr Thr Thr Thr Arg Thr Thr Thr Arg Thr Thr Thr Lys Thr Leu
                        260             265             270

Pro Thr Thr Asn Lys Lys Cys Ser Ala Lys Ile Thr Ala Gln Gly Tyr
                        275             280             285

Lys Cys Cys Ser Asp Pro Asn Cys Val Val Tyr Tyr Thr Asp Glu Asp
                    290             295             300

Gly Thr Trp Gly Val Glu Asn Asn Gln Trp Cys Gly Cys Gly Val Glu
            305                 310             315             320

Ala Cys Ser Gly Lys Ile Thr Ala Gln Gly Tyr Lys Cys Cys Ser Asp
                            325             330             335

Pro Lys Cys Val Val Tyr Tyr Thr Asp Asp Asp Gly Lys Trp Gly Val
                        340             345             350

Glu Asn Asn Glu Trp Cys Gly Cys Gly Leu
                        355             360

<210> SEQ ID NO 15
<211> LENGTH: 473
<212> TYPE: PRT
<213> ORGANISM: Neocallimastix patriciarum

<400> SEQUENCE: 15

Met Lys Phe Leu Asn Thr Phe Ser Leu Leu Ser Leu Ala Ile Ile Gly
            1               5              10              15
```

-continued

```
Ser Lys Ala Met Lys Asn Ile Ser Ser Lys Glu Leu Val Lys Asp Leu
             20                  25                  30
Thr Ile Gly Trp Ser Leu Gly Asn Thr Leu Asp Ala Thr Cys Phe Glu
             35                  40                  45
Thr Leu Asp Tyr Asn Lys Asn Gln Ile Ala Ser Glu Thr Cys Trp Gly
         50                  55                  60
Asn Val Lys Thr Thr Gln Glu Leu Tyr Lys Leu Ser Asp Leu Gly
 65                  70                  75                  80
Phe Asn Thr Phe Arg Ile Pro Thr Thr Trp Ser Gly His Phe Gly Asn
                 85                  90                  95
Ala Pro Asp Tyr Lys Ile Asn Asp Gln Trp Met Lys Arg Val His Glu
             100                 105                 110
Ile Val Asp Tyr Ala Ile Asn Thr Gly Gly Tyr Ala Ile Leu Asn Ile
         115                 120                 125
His His Glu Thr Trp Asn His Ala Phe Gln Lys Asn Leu Glu Ser Ala
     130                 135                 140
Lys Lys Ile Leu Val Ala Ile Trp Lys Gln Ile Ala Ala Glu Phe Ala
145                 150                 155                 160
Asp Tyr Asp Glu His Leu Ile Phe Glu Gly Met Asn Glu Pro Arg Lys
                 165                 170                 175
Val Gly Asp Pro Ala Glu Trp Asn Gly Gly Asp Tyr Glu Gly Trp Asn
             180                 185                 190
Phe Val Asn Glu Met Asn Asp Leu Phe Val Lys Thr Ile Arg Ala Thr
         195                 200                 205
Gly Gly Asn Asn Ala Leu Arg His Leu Met Ile Pro Thr Tyr Ala Ala
     210                 215                 220
Cys Ile Asn Asp Gly Ala Ile Asn Asn Phe Lys Phe Pro Ser Gly Asp
225                 230                 235                 240
Asp Lys Val Ile Val Ser Leu His Ser Tyr Ser Pro Tyr Asn Phe Ala
                 245                 250                 255
Leu Asn Asn Gly Ala Gly Ala Ile Ser Asn Phe Tyr Asp Gly Ser Glu
             260                 265                 270
Ile Asp Trp Ala Met Asn Thr Ile Asn Ser Lys Phe Ile Ser Arg Gly
         275                 280                 285
Ile Pro Val Ile Ile Gly Glu Phe Gly Ala Met Asn Arg Asn Asn Glu
     290                 295                 300
Asp Asp Arg Glu Arg Trp Ala Glu Tyr Tyr Ile Lys Lys Ala Thr Ser
305                 310                 315                 320
Ile Gly Val Pro Cys Val Ile Trp Asp Asn Gly Tyr Phe Glu Gly Glu
                 325                 330                 335
Gly Glu Arg Phe Gly Leu Ile Asn Arg Ser Thr Leu Gln Val Val Tyr
             340                 345                 350
Pro Lys Leu Val Asn Gly Leu Ile Lys Gly Leu Gly Asn Ser Ile Lys
         355                 360                 365
Thr Arg Thr Thr Ile Arg Arg Thr Thr Thr Thr Thr Ser Gln Ser
     370                 375                 380
Gln Pro Thr Asn Asn Asp Ser Cys Phe Ser Val Asn Leu Gly Tyr Ser
385                 390                 395                 400
Cys Cys Asn Gly Cys Glu Val Glu Tyr Thr Asp Ser Asp Gly Glu Trp
                 405                 410                 415
Gly Val Glu Asn Gly Asn Trp Cys Gly Ile Lys Ser Ser Cys Ser Asn
             420                 425                 430
Thr Ser Arg Ile Cys Trp Ser Glu Lys Leu Gly Tyr Pro Cys Cys Gln
```

```
                    435                 440                 445
Asn Thr Ser Ser Val Val Tyr Thr Asp Asn Asp Gly Lys Trp Gly Val
            450                 455                 460
Glu Asn Gly Asn Trp Cys Gly Ile Tyr
465                 470

<210> SEQ ID NO 16
<211> LENGTH: 40
<212> TYPE: PRT
<213> ORGANISM: Artificial Sequence
<220> FEATURE:
<223> OTHER INFORMATION: Description of Artificial Sequence:part of
      Neocallimastix patriciarum  xylanase

<400> SEQUENCE: 16

Cys Ser Ala Arg Ile Thr Ala Gln Gly Tyr Lys Cys Cys Ser Asp Pro
  1               5                  10                  15
Asn Cys Val Val Tyr Tyr Thr Asp Glu Asp Gly Thr Trp Gly Val Glu
             20                  25                  30
Asn Asn Asp Trp Cys Gly Cys Gly
         35                  40

<210> SEQ ID NO 17
<211> LENGTH: 40
<212> TYPE: PRT
<213> ORGANISM: Artificial Sequence
<220> FEATURE:
<223> OTHER INFORMATION: Description of Artificial Sequence:part of
      Neocallimastix patriciarum xylanase

<400> SEQUENCE: 17

Cys Ser Ser Lys Ile Thr Ser Gln Gly Tyr Lys Cys Cys Ser Asp Pro
  1               5                  10                  15
Asn Cys Val Val Phe Tyr Thr Asp Asp Asp Gly Lys Trp Gly Val Glu
             20                  25                  30
Asn Asn Asp Trp Cys Gly Cys Gly
         35                  40

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence:part of
      Piromyces xylanase

<400> SEQUENCE: 18

Cys Pro Ser Thr Ile Thr Ser Gln Gly Tyr Lys Cys Cys Ser Ser Asn
  1               5                  10                  15
Cys Asp Ile Ile Tyr Arg Asp Gln Ser Gly Asp Trp Gly Val Glu Asn
             20                  25                  30
Asp Glu Trp Cys Gly Cys Gly
         35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence:part of
      Piromyces xylanase

<400> SEQUENCE: 19
```

```
Cys Pro Ser Ser Ile Lys Asn Gln Gly Tyr Lys Cys Cys Ser Asp Ser
 1               5                  10                  15

Cys Glu Ile Val Leu Thr Asp Ser Asp Gly Asp Trp Gly Ile Glu Asn
                20                  25                  30

Asp Glu Trp Cys Gly Cys Gly
            35
```

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence:part of
      Piromyces mannosidase

<400> SEQUENCE: 20

```
Cys Trp Ser Ile Asn Leu Gly Tyr Pro Cys Cys Ile Gly Asp Tyr Val
 1               5                  10                  15

Val Thr Thr Asp Glu Asn Gly Asp Trp Gly Val Glu Asn Asn Glu Trp
                20                  25                  30

Cys Gly Ile Val
        35
```

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence:part of
      Piromyces mannosidase

<400> SEQUENCE: 21

```
Cys Trp Ser Glu Pro Leu Gly Tyr Pro Cys Cys Val Gly Asn Thr Val
 1               5                  10                  15

Ile Ser Ala Asp Glu Ser Gly Asp Trp Gly Val Glu Asn Asn Glu Trp
                20                  25                  30

Cys Gly Ile Val
        35
```

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence:part of
      Piromyces mannosidase

<400> SEQUENCE: 22

```
Cys Trp Ala Glu Phe Leu Gly Tyr Pro Cys Cys Val Gly Asn Thr Val
 1               5                  10                  15

Ile Ser Thr Asp Glu Phe Gly Asp Trp Gly Val Glu Asn Asp Asp Trp
                20                  25                  30

Cys Gly Ile Leu
        35
```

<210> SEQ ID NO 23
<211> LENGTH: 326
<212> TYPE: PRT
<213> ORGANISM: Neocallimastix patriciarum

<400> SEQUENCE: 23

```
Gly Ser Thr Lys Asn Phe Phe Asp Asn Gln Ile Tyr Ala Asn Pro Lys
 1               5                  10                  15
```

-continued

```
Phe Ile Glu Glu Val Asn Ser Ser Ile Pro Arg Leu Ser Tyr Asp Leu
                20                  25                  30

Gln Gln Lys Ala Gln Lys Val Lys Asn Val Pro Thr Ala Val Trp Leu
             35                  40                  45

Ala Trp Asp Gly Ala Thr Gly Glu Val Ala Gln His Leu Lys Ala Ala
         50                  55                  60

Gly Ser Lys Thr Val Val Phe Ile Met Tyr Met Ile Pro Thr Arg Asp
 65                  70                  75                  80

Cys Asn Ala Asn Ala Ser Ala Gly Gly Ala Gly Asn Leu Asn Thr Tyr
                 85                  90                  95

Lys Gly Tyr Val Asp Asn Ile Ala Arg Thr Ile Arg Ser Tyr Pro Asn
            100                 105                 110

Ser Lys Val Val Met Ile Leu Glu Pro Asp Thr Leu Gly Asn Leu Val
        115                 120                 125

Thr Ala Asn Ser Ala Asn Cys Gln Asn Val Arg Asn Leu His Lys Asn
    130                 135                 140

Ala Leu Ser Tyr Gly Val Asn Val Phe Gly Ser Met Ser Asn Val Ser
145                 150                 155                 160

Val Tyr Leu Asp Ala Ala His Gly Ala Trp Leu Gly Ser Ser Thr Asp
                165                 170                 175

Lys Val Ala Ser Val Val Lys Glu Ile Leu Asn Asn Ala Pro Asn Gly
            180                 185                 190

Lys Ile Arg Gly Leu Ser Thr Asn Ile Ser Asn Tyr Gln Ser Ile Ser
        195                 200                 205

Ser Glu Tyr Gln Tyr His Gln Lys Leu Ala Ser Ala Leu Ala Ala Val
    210                 215                 220

Gly Val Pro Asn Met His Phe Ile Val Asp Thr Gly Arg Asn Gly Val
225                 230                 235                 240

Thr Ile Asn Ser Gly Thr Trp Cys Asn Leu Val Gly Thr Gly Leu Gly
                245                 250                 255

Glu Arg Pro Arg Gly Asn Pro Asn Ala Gly Met Pro Leu Leu Asp Ala
            260                 265                 270

Tyr Met Trp Leu Lys Thr Pro Gly Glu Ser Asp Gly Ser Ser Ser Gly
        275                 280                 285

Ser Arg Ala Asp Pro Asn Cys Ser Ser Asn Asp Ser Leu Arg Gly Ala
    290                 295                 300

Pro Asp Ala Gly Gln Trp Phe His Asp Tyr Phe Ala Gln Leu Val Arg
305                 310                 315                 320

Asn Ala Arg Pro Ser Phe
                325

<210> SEQ ID NO 24
<211> LENGTH: 360
<212> TYPE: PRT
<213> ORGANISM: Trichoderma reesei

<400> SEQUENCE: 24

Tyr Ser Gly Asn Pro Phe Val Gly Val Thr Pro Trp Ala Asn Ala Tyr
 1               5                  10                  15

Tyr Ala Ser Glu Val Ser Ser Leu Ala Ile Pro Ser Leu Thr Gly Ala
             20                  25                  30

Met Ala Thr Ala Ala Ala Val Ala Lys Val Pro Ser Phe Met Trp
         35                  40                  45

Leu Asp Thr Leu Asp Lys Thr Pro Leu Met Glu Gln Thr Leu Ala Asp
```

```
            50                  55                  60
Ile Arg Thr Ala Asn Lys Asn Gly Gly Asn Tyr Ala Gly Gln Phe Val
 65                  70                  75                  80

Val Tyr Asp Leu Pro Asp Arg Asp Cys Ala Ala Leu Ala Ser Asn Gly
                 85                  90                  95

Glu Tyr Ser Ile Ala Asp Gly Gly Val Ala Lys Tyr Lys Asn Tyr Ile
            100                 105                 110

Asp Thr Ile Arg Gln Ile Val Val Glu Tyr Ser Asp Ile Arg Thr Leu
        115                 120                 125

Leu Val Ile Glu Pro Asp Ser Leu Ala Asn Leu Val Thr Asn Leu Gly
    130                 135                 140

Thr Pro Lys Cys Ala Asn Ala Gln Ser Ala Tyr Leu Glu Cys Ile Asn
145                 150                 155                 160

Tyr Ala Val Thr Gln Leu Asn Leu Pro Asn Val Ala Met Tyr Leu Asp
                165                 170                 175

Ala Gly His Ala Gly Trp Leu Gly Trp Pro Ala Asn Gln Asp Pro Ala
            180                 185                 190

Ala Gln Leu Phe Ala Asn Val Tyr Lys Asn Ala Ser Ser Pro Arg Ala
        195                 200                 205

Leu Arg Gly Leu Ala Thr Asn Val Ala Asn Tyr Asn Gly Trp Asn Ile
    210                 215                 220

Thr Ser Pro Pro Ser Tyr Thr Gln Gly Asn Ala Val Tyr Asn Glu Lys
225                 230                 235                 240

Leu Tyr Ile His Ala Ile Gly Pro Leu Leu Ala Asn His Gly Trp Ser
                245                 250                 255

Asn Ala Phe Phe Ile Thr Asp Gln Gly Arg Ser Gly Lys Gln Pro Thr
            260                 265                 270

Gly Gln Gln Gln Trp Gly Asp Trp Cys Asn Val Ile Gly Thr Gly Phe
        275                 280                 285

Gly Ile Arg Pro Ser Ala Asn Thr Gly Asp Ser Leu Leu Asp Ser Phe
    290                 295                 300

Val Trp Val Lys Pro Gly Gly Glu Cys Asp Gly Thr Ser Asp Ser Ser
305                 310                 315                 320

Ala Pro Arg Phe Asp Ser His Cys Ala Leu Pro Asp Ala Leu Gln Pro
                325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
        355                 360

<210> SEQ ID NO 25
<211> LENGTH: 360
<212> TYPE: PRT
<213> ORGANISM: Fusarium oxysporum

<400> SEQUENCE: 25

Ala Ser Asp Asn Pro Tyr Ala Gly Val Asp Leu Trp Ala Asn Asn Tyr
  1               5                  10                  15

Tyr Arg Ser Glu Val Met Asn Leu Ala Val Pro Lys Leu Ser Gly Ala
             20                  25                  30

Lys Ala Thr Ala Ala Ala Lys Val Ala Asp Val Pro Ser Phe Gln Trp
         35                  40                  45

Met Asp Thr Tyr Asp His Ile Ser Leu Met Glu Asp Thr Leu Ala Asp
     50                  55                  60
```

```
Ile Arg Lys Ala Asn Lys Ala Gly Gly Lys Tyr Ala Gly Gln Phe Val
 65                  70                  75                  80

Val Tyr Asp Leu Pro Asn Arg Asp Cys Ala Ala Ala Ser Asn Gly
                 85                  90                  95

Glu Tyr Ser Leu Asp Lys Asp Gly Ala Asn Lys Tyr Lys Ala Tyr Ile
                100                 105                 110

Ala Lys Ile Lys Gly Ile Leu Gln Asn Tyr Ser Asp Thr Lys Val Ile
                115                 120                 125

Leu Val Ile Glu Pro Asp Ser Leu Ala Asn Leu Val Thr Asn Leu Asn
            130                 135                 140

Val Asp Lys Cys Ala Lys Ala Glu Ser Ala Tyr Lys Glu Leu Thr Val
145                 150                 155                 160

Tyr Ala Ile Lys Glu Leu Asn Leu Pro Asn Val Ser Met Tyr Leu Asp
                165                 170                 175

Ala Gly His Gly Gly Trp Leu Gly Trp Pro Ala Asn Ile Gly Pro Ala
            180                 185                 190

Ala Lys Leu Tyr Ala Gln Ile Tyr Lys Asp Ala Gly Lys Pro Ser Arg
            195                 200                 205

Val Arg Gly Leu Val Thr Asn Val Ser Asn Tyr Asn Gly Trp Lys Leu
            210                 215                 220

Ser Thr Lys Pro Asp Tyr Thr Glu Ser Asn Pro Asn Tyr Asp Glu Gln
225                 230                 235                 240

Arg Tyr Ile Asn Ala Phe Ala Pro Leu Leu Ala Gln Glu Gly Trp Ser
                245                 250                 255

Asn Val Lys Phe Ile Val Asp Gln Gly Arg Ser Gly Lys Gln Pro Thr
                260                 265                 270

Gly Gln Lys Ala Gln Gly Asp Trp Cys Asn Ala Lys Gly Thr Gly Phe
            275                 280                 285

Gly Leu Arg Pro Ser Thr Asn Thr Gly Asp Ala Leu Ala Asp Ala Phe
            290                 295                 300

Val Trp Val Lys Pro Gly Gly Glu Ser Asp Gly Thr Ser Asp Thr Ser
305                 310                 315                 320

Ala Ala Arg Tyr Asp Tyr His Cys Gly Leu Asp Asp Ala Leu Lys Pro
                325                 330                 335

Ala Pro Glu Ala Gly Thr Trp Phe Gln Ala Tyr Phe Lys Gln Leu Leu
            340                 345                 350

Asp Asn Ala Asn Pro Ser Phe Leu
            355                 360

<210> SEQ ID NO 26
<211> LENGTH: 352
<212> TYPE: PRT
<213> ORGANISM: Agaricus bisporus

<400> SEQUENCE: 26

Gly Ala Gly Asn Pro Tyr Thr Gly Lys Thr Val Trp Leu Ser Pro Phe
  1               5                  10                  15

Tyr Ala Asp Glu Val Ala Gln Ala Ala Asp Ile Ser Asn Pro Ser
                 20                  25                  30

Leu Ala Thr Lys Ala Ala Ser Val Ala Lys Ile Pro Thr Phe Val Trp
             35                  40                  45

Phe Asp Thr Val Ala Lys Val Pro Asp Leu Gly Gly Tyr Leu Ala Asp
         50                  55                  60

Ala Arg Ser Lys Asn Gln Leu Val Gln Ile Val Val Tyr Asp Leu Pro
 65                  70                  75                  80
```

-continued

```
Asp Arg Asp Cys Ala Ala Leu Ala Ser Asn Gly Glu Phe Ser Leu Ala
                85                  90                  95

Asn Asp Gly Leu Asn Lys Tyr Lys Asn Tyr Val Asp Gln Ile Ala Ala
            100                 105                 110

Gln Ile Lys Gln Phe Pro Asp Val Ser Val Ala Val Ile Glu Pro
        115                 120                 125

Asp Ser Leu Ala Asn Leu Val Thr Asn Leu Asn Val Gln Lys Cys Ala
    130                 135                 140

Asn Ala Gln Ser Ala Tyr Lys Glu Gly Val Ile Tyr Ala Val Gln Lys
145                 150                 155                 160

Leu Asn Ala Val Gly Val Thr Met Tyr Ile Asp Ala Gly His Ala Gly
                165                 170                 175

Trp Leu Gly Trp Pro Ala Asn Leu Ser Pro Ala Gln Leu Phe Ala
            180                 185                 190

Gln Ile Tyr Arg Asp Ala Gly Ser Pro Arg Asn Leu Arg Gly Ile Ala
        195                 200                 205

Thr Asn Val Ala Asn Phe Asn Ala Leu Arg Ala Ser Ser Pro Asp Pro
    210                 215                 220

Ile Thr Gln Gly Asn Ser Asn Tyr Asp Glu Ile His Tyr Ile Glu Ala
225                 230                 235                 240

Leu Ala Pro Met Leu Ser Asn Ala Gly Phe Pro Ala His Phe Ile Val
                245                 250                 255

Asp Gln Gly Arg Ser Gly Val Gln Asn Ile Arg Asp Gln Trp Gly Asp
            260                 265                 270

Trp Cys Asn Val Lys Gly Ala Gly Phe Gly Gln Arg Pro Thr Thr Asn
        275                 280                 285

Thr Gly Ser Ser Leu Ile Asp Ala Ile Val Trp Val Lys Pro Gly Gly
    290                 295                 300

Glu Cys Asp Gly Thr Ser Asp Asn Ser Ser Pro Arg Phe Asp Ser His
305                 310                 315                 320

Cys Ser Leu Ser Asp Ala His Gln Pro Ala Pro Glu Ala Gly Thr Trp
                325                 330                 335

Phe Gln Ala Tyr Phe Glu Thr Leu Val Ala Asn Ala Asn Pro Ala Leu
            340                 345                 350

<210> SEQ ID NO 27
<211> LENGTH: 286
<212> TYPE: PRT
<213> ORGANISM: Cellulomonas fimi

<400> SEQUENCE: 27

Pro Thr Val Thr Pro Gln Pro Thr Ser Gly Phe Tyr Val Asp Pro Thr
  1               5                  10                  15

Thr Gln Gly Tyr Arg Ala Trp Gln Ala Ala Ser Gly Thr Asp Lys Ala
                20                  25                  30

Leu Leu Glu Lys Ile Ala Leu Thr Pro Gln Ala Tyr Trp Val Gly Asn
            35                  40                  45

Trp Ala Asp Ala Ser His Ala Gln Ala Lys Val Ala Asp Tyr Thr Gly
    50                  55                  60

Arg Ala Val Ala Ala Gly Lys Thr Pro Met Leu Val Val Tyr Ala Ile
65                  70                  75                  80

Pro Gly Arg Asp Cys Gly Ser His Ser Gly Gly Gly Val Ser Glu Ser
                85                  90                  95

Glu Tyr Ala Arg Trp Val Asp Thr Val Ala Gln Gly Ile Lys Gly Met
```

```
                100                 105                 110
Pro Ile Val Ile Leu Glu Pro Asp Ala Leu Ala Gln Leu Gly Asp Cys
            115                 120                 125

Ser Gly Gln Gly Asp Arg Val Gly Phe Leu Lys Tyr Ala Ala Lys Ser
130                 135                 140

Leu Thr Leu Lys Gly Ala Arg Val Tyr Ile Asp Ala Gly His Ala Lys
145                 150                 155                 160

Trp Leu Ser Val Asp Thr Pro Val Asn Arg Leu Asn Gln Val Gly Phe
                165                 170                 175

Glu Tyr Ala Val Gly Phe Ala Leu Asn Thr Ser Asn Tyr Gln Thr Thr
                180                 185                 190

Ala Asp Ser Lys Ala Tyr Gly Gln Gln Ile Ser Gln Arg Leu Gly Gly
            195                 200                 205

Lys Lys Phe Val Ile Asp Thr Ser Arg Asn Gly Asn Gly Ser Asn Gly
            210                 215                 220

Glu Trp Cys Asn Pro Arg Gly Arg Ala Leu Gly Glu Arg Pro Val Ala
225                 230                 235                 240

Val Asn Asp Gly Ser Gly Leu Asp Ala Leu Leu Trp Val Lys Leu Pro
                245                 250                 255

Gly Glu Ser Asp Gly Ala Cys Asn Gly Gly Pro Ala Ala Gly Gln Trp
                260                 265                 270

Trp Gln Lys Ile Ala Leu Glu Met Ala Arg Asn Ala Arg Trp
            275                 280                 285

<210> SEQ ID NO 28
<211> LENGTH: 291
<212> TYPE: PRT
<213> ORGANISM: Thermomonospora fusca

<400> SEQUENCE: 28

Ala Asn Asp Ser Pro Phe Tyr Val Asn Pro Asn Met Ser Ser Ala Lys
  1               5                  10                  15

Trp Val Arg Asn Asn Pro Asn Asp Pro Arg Thr Pro Val Ile Arg Asp
                20                  25                  30

Arg Ile Ala Ser Val Pro Gln Gly Thr Trp Phe Ala His His Asn Pro
            35                  40                  45

Gly Gln Ile Thr Gly Gln Val Asp Ala Leu Met Ser Ala Ala Gln Ala
      50                  55                  60

Ala Gly Lys Ile Pro Ile Leu Val Val Tyr Asn Ala Pro Gly Arg Asp
65                  70                  75                  80

Cys Gly Asn His Ser Ser Gly Gly Ala Pro Ser His Ser Ala Tyr Arg
                85                  90                  95

Ser Trp Ile Asp Glu Phe Ala Ala Gly Leu Lys Asn Arg Pro Ala Tyr
              100                 105                 110

Ile Ile Val Glu Pro Asp Leu Ile Ser Leu Met Ser Ser Cys Met Gln
            115                 120                 125

His Val Gln Gln Glu Val Leu Glu Thr Met Ala Tyr Ala Gly Lys Ala
        130                 135                 140

Leu Lys Ala Gly Ser Ser Gln Ala Arg Ile Tyr Phe Asp Ala Gly His
145                 150                 155                 160

Ser Ala Ser Asp Ser Pro Gln Met Ala Ser Trp Leu Gln Gln Ala
                165                 170                 175

Asp Ile Ser Asn Ser Ala His Gly Ile Ala Thr Asn Thr Ser Asn Tyr
                180                 185                 190
```

```
Arg Trp Thr Ala Asp Glu Val Ala Tyr Ala Lys Ala Val Leu Ser Ala
            195                 200                 205

Ile Gly Asn Pro Ser Leu Arg Ala Val Ile Asp Thr Ser Arg Asn Gly
            210                 215                 220

Asn Gly Pro Ala Gly Asn Lys Trp Cys Asp Pro Ser Gly Arg Ala Ile
225                 230                 235                 240

Gly Thr Pro Ser Thr Thr Asn Thr Gly Asp Pro Met Ile Asp Ala Phe
            245                 250                 255

Leu Trp Ile Lys Leu Pro Gly Glu Ala Asp Gly Cys Ile Ala Gly Ala
            260                 265                 270

Gly Gln Phe Val Pro Gln Ala Ala Tyr Glu Met Ala Ile Ala Ala Gly
            275                 280                 285

Gly His Gln
            290

<210> SEQ ID NO 29
<211> LENGTH: 290
<212> TYPE: PRT
<213> ORGANISM: Streptomyces Ksm-9

<400> SEQUENCE: 29

Ala Gly Thr Thr Ala Leu Pro Ser Met Glu Leu Tyr Arg Ala Glu Ala
1               5                   10                  15

Gly Val His Ala Trp Leu Asp Ala Asn Pro Gly Asp His Arg Ala Pro
            20                  25                  30

Leu Ile Ala Glu Arg Ile Gly Ser Gln Pro Gln Ala Val Trp Phe Ala
            35                  40                  45

Gly Ala Tyr Asn Pro Gly Thr Ile Thr Gln Gln Val Ala Glu Val Thr
    50                  55                  60

Ser Ala Ala Ala Ala Gly Gln Leu Pro Val Val Pro Tyr Met
65                  70                  75                  80

Ile Pro Phe Arg Asp Cys Gly Asn His Ser Gly Gly Gly Ala Pro Ser
            85                  90                  95

Phe Ala Ala Tyr Ala Glu Trp Ser Gly Leu Phe Ala Ala Gly Leu Gly
            100                 105                 110

Ser Glu Pro Val Val Val Leu Glu Pro Asp Ala Ile Pro Leu Ile
            115                 120                 125

Asp Cys Leu Asp Asn Gln Gln Arg Ala Glu Arg Leu Ala Ala Leu Ala
130                 135                 140

Gly Leu Ala Glu Ala Val Thr Asp Ala Asn Pro Glu Ala Arg Val Tyr
145                 150                 155                 160

Tyr Asp Val Gly His Ser Ala Trp His Ala Pro Ala Ala Ile Ala Pro
            165                 170                 175

Thr Leu Val Glu Ala Gly Ile Leu Glu His Gly Ala Gly Ile Ala Thr
            180                 185                 190

Asn Ile Ser Asn Tyr Arg Thr Thr Asp Glu Thr Ala Tyr Ala Ser
            195                 200                 205

Ala Val Ile Ala Glu Leu Gly Gly Leu Gly Ala Val Val Asp Thr
            210                 215                 220

Ser Arg Asn Gly Asn Gly Pro Leu Gly Ser Glu Trp Cys Asp Pro Pro
225                 230                 235                 240

Gly Arg Leu Val Gly Asn Asn Pro Thr Val Asn Pro Gly Val Pro Gly
            245                 250                 255

Val Asp Ala Phe Leu Trp Ile Lys Leu Pro Gly Glu Leu Asp Gly Cys
            260                 265                 270
```

```
Asp Gly Pro Val Gly Ser Phe Ser Pro Ala Lys Ala Tyr Glu Leu Ala
        275                 280                 285
Gly Gly
    290
```